US012616800B2

(12) United States Patent (10) Patent No.: US 12,616,800 B2
Calderwood et al. (45) Date of Patent: May 5, 2026

(54) MEDICAMENT DELIVERY MEMBER GUARD LOCK ASSEMBLY

(71) Applicant: SHL MEDICAL AG, Zug (CH)

(72) Inventors: Gary Calderwood, Stockholm (SE); Björn Krohn, Arsta (SE); Joakim Lindholm, Saltsjö-Boo (SE); Tilde Rolder, Stockholm (SE)

( * ) Notice: Subject to any disclaimer, the term of this patent is extended or adjusted under 35 U.S.C. 154(b) by 627 days.

(21) Appl. No.: 18/025,713

(22) PCT Filed: Oct. 12, 2021

(86) PCT No.: PCT/EP2021/078113
§ 371 (c)(1),
(2) Date: Mar. 10, 2023

(87) PCT Pub. No.: WO2022/078986
PCT Pub. Date: Apr. 21, 2022

(65) Prior Publication Data
US 2023/0355892 A1     Nov. 9, 2023

(30) Foreign Application Priority Data

Oct. 14, 2020    (EP) ..................................... 20201659
May 7, 2021    (EP) ..................................... 21172824

(51) Int. Cl.
    *A61M 5/32*        (2006.01)
    *A61M 5/20*        (2006.01)
    *A61M 5/315*       (2006.01)
(52) U.S. Cl.
    CPC ............ *A61M 5/3243* (2013.01); *A61M 5/20*
        (2013.01); *A61M 5/2033* (2013.01);
        (Continued)

(58) Field of Classification Search
    CPC .... A61M 5/3243; A61M 5/20; A61M 5/2033;
                A61M 5/31566; A61M 5/31571;
    (Continued)

(56) References Cited

U.S. PATENT DOCUMENTS 7,449,012 B2    11/2008  Young et al.
8,409,149 B2    4/2013   Hommann et al.
        (Continued)

FOREIGN PATENT DOCUMENTS

EP        2637718 B1      2/2018
JP        2008536597 A    6/2013
        (Continued)

OTHER PUBLICATIONS

International Search Report and Written Opinion for Int. App. No. PCT/EP2021/078113, mailed Jan. 13, 2022.

*Primary Examiner* — Tasnim Mehjabin Ahmed
(74) *Attorney, Agent, or Firm* — McDonnell Boehnen Hulbert & Berghoff LLP

(57)        ABSTRACT

The application describes a medicament delivery member guard lock assembly for a medicament delivery device, the medicament delivery member guard lock assembly includes a housing having a recess or a slit; a medicament delivery member guard slidably arranged in the housing, the medicament delivery member guard extending from a proximal end to a distal end; a lock activation sleeve slidably arranged in the housing at the distal end of the medicament delivery member guard; and a medicament delivery member guard lock arranged in the housing adjacent to the lock activation sleeve, wherein the medicament delivery member guard lock has a flexible arm pivotally attached to a base, wherein the flexible arm has a proximal part, a distal part and is attached to the base between the proximal part and the distal (Continued)

part, and wherein the proximal part of the flexible arm is arranged adjacent to the recess or slit in the housing.

20 Claims, 57 Drawing Sheets

(52) U.S. Cl.
CPC .... *A61M 5/31566* (2013.01); *A61M 5/31571* (2013.01); *A61M 5/3202* (2013.01); *A61M 5/3245* (2013.01); *A61M 2005/2073* (2013.01); *A61M 5/3204* (2013.01)

(58) Field of Classification Search
CPC .............. A61M 5/3202; A61M 5/3245; A61M 5/3204; A61M 2005/2073
See application file for complete search history.

(56) References Cited

U.S. PATENT DOCUMENTS

| | | | |
|---|---|---|---|
| 8,900,202 B2 | 12/2014 | Helmer et al. | |
| 9,132,236 B2 | 9/2015 | Karlsson et al. | |
| 9,381,307 B2 | 7/2016 | Eaton et al. | |
| 9,861,755 B2 | 1/2018 | Beek et al. | |
| 10,201,662 B2 | 2/2019 | Morris et al. | |
| 10,449,301 B2 | 10/2019 | Plumptre et al. | |
| 10,471,217 B2 | 11/2019 | Plumptre et al. | |
| 2008/0051715 A1* | 2/2008 | Young | A61M 5/3245 604/135 |
| 2017/0258998 A1 | 9/2017 | Stamp | |
| 2018/0001030 A1 | 1/2018 | Pedersen et al. | |
| 2018/0214640 A1 | 8/2018 | Kemp et al. | |
| 2018/0304026 A1 | 10/2018 | Morris et al. | |
| 2019/0134315 A1 | 5/2019 | Moser et al. | |
| 2019/0336698 A1 | 11/2019 | Klitmose | |
| 2019/0381251 A1* | 12/2019 | Mosebach | A61M 5/2033 |
| 2021/0402102 A1* | 12/2021 | Timmis | A61M 5/3202 |

FOREIGN PATENT DOCUMENTS

| | | | |
|---|---|---|---|
| JP | 2014079375 A | 5/2014 | |
| JP | 2012504009 A | 7/2014 | |
| JP | 2021512735 A | 5/2021 | |
| WO | 2010/147552 A1 | 12/2010 | |
| WO | 2012/138285 A1 | 10/2012 | |
| WO | 2014/139914 A1 | 9/2014 | |
| WO | 2014/139916 A1 | 9/2014 | |
| WO | 2014/154490 A2 | 10/2014 | |
| WO | 2018/011417 A1 | 1/2018 | |
| WO | 2019097076 A1 | 5/2019 | |
| WO | 2020/037256 A1 | 2/2020 | |
| WO | 2022117684 A1 | 6/2022 | |

* cited by examiner

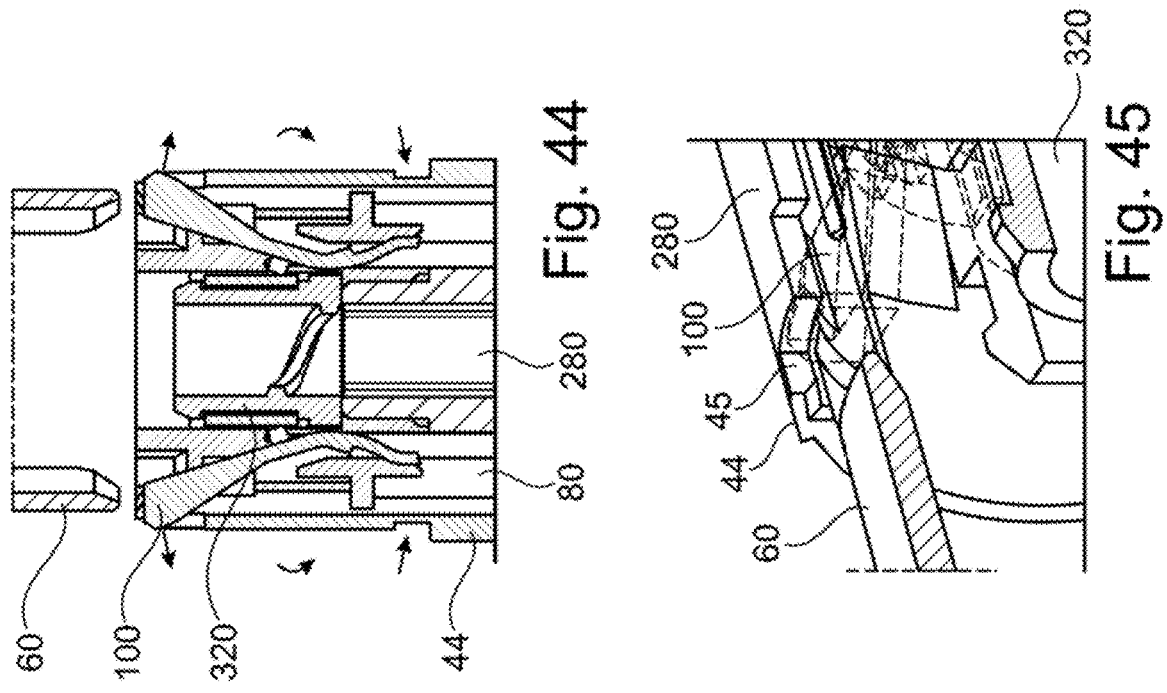
Fig. 44
Fig. 45
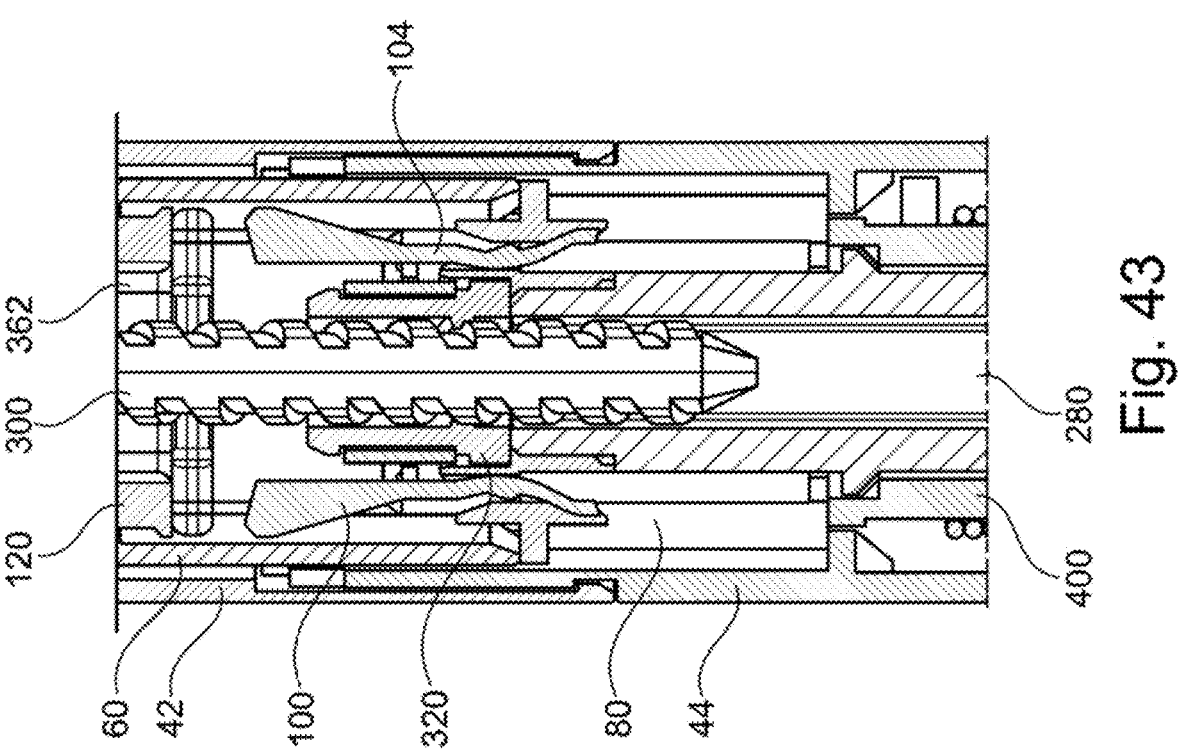
Fig. 43

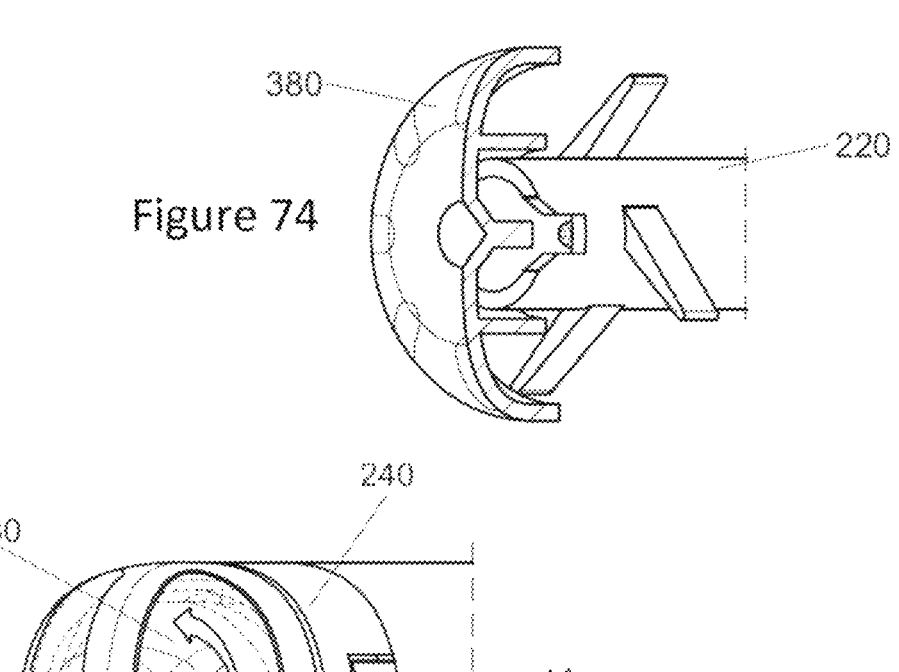
Figure 74
Figure 75
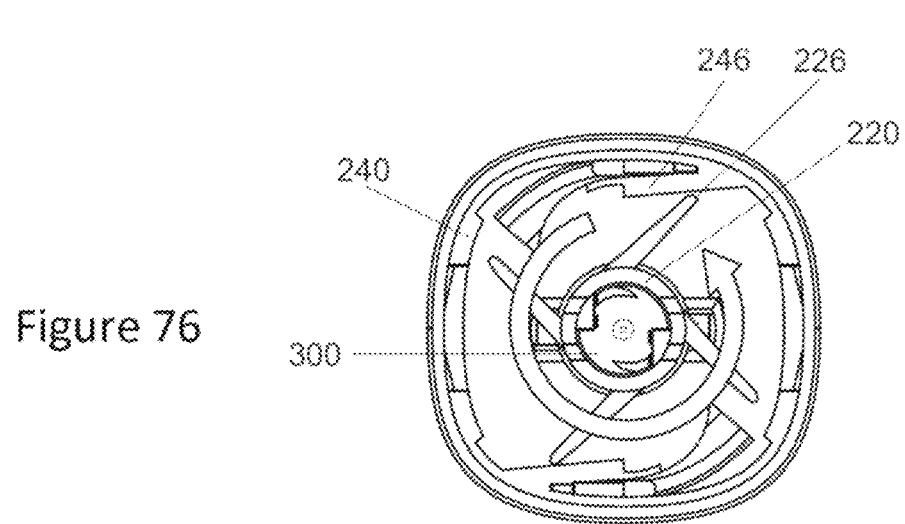
Figure 76

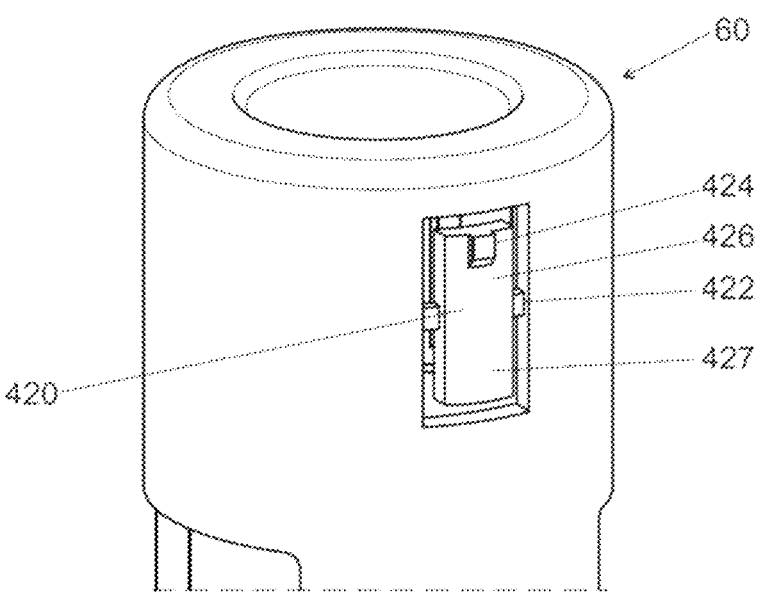
Fig. 88
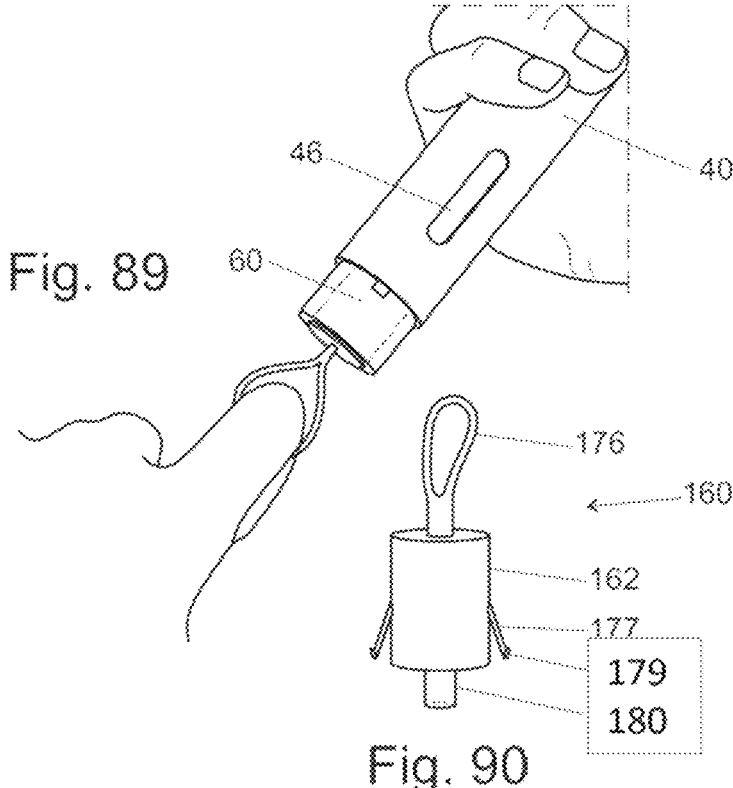
Fig. 89
Fig. 90

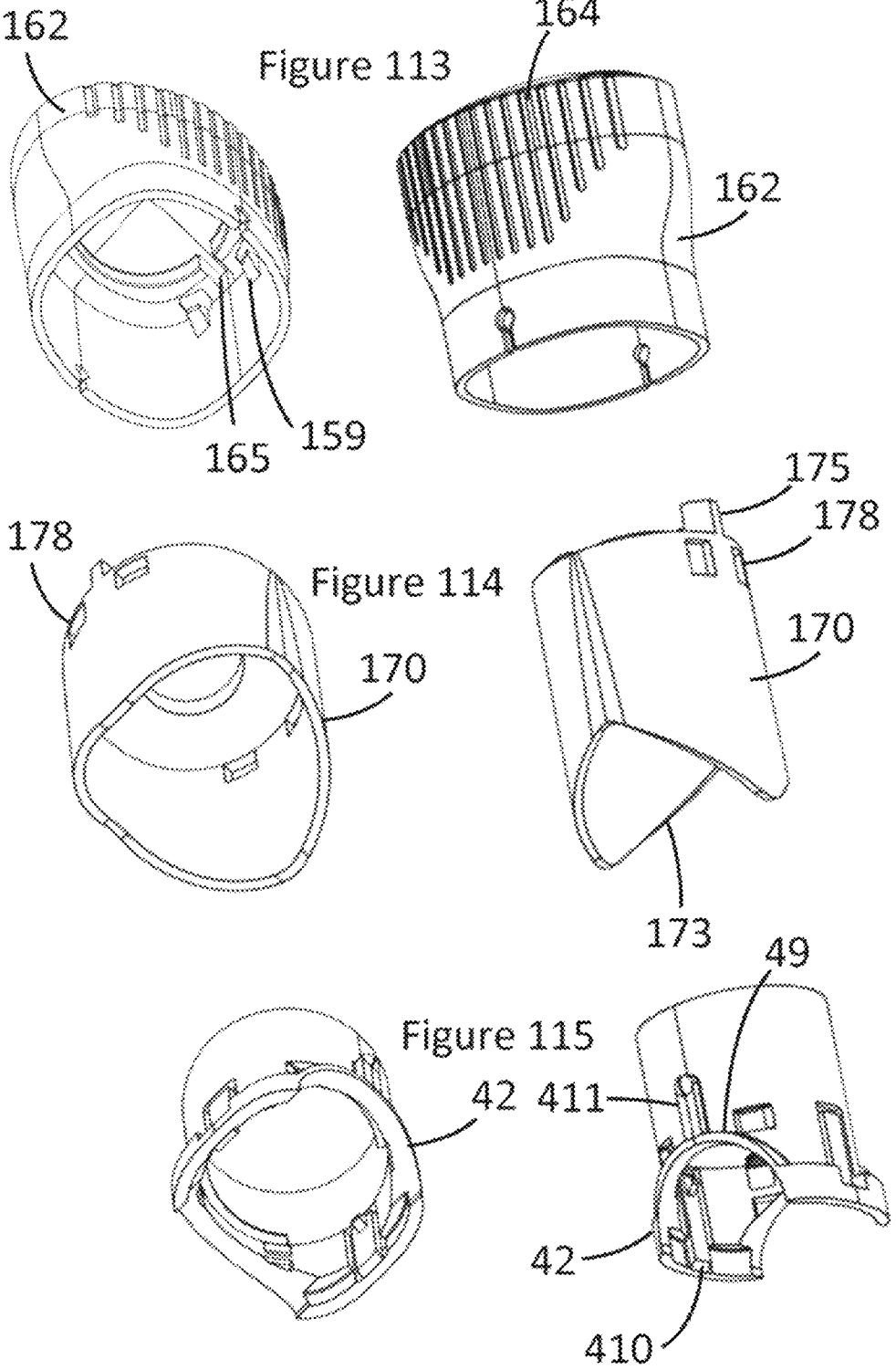

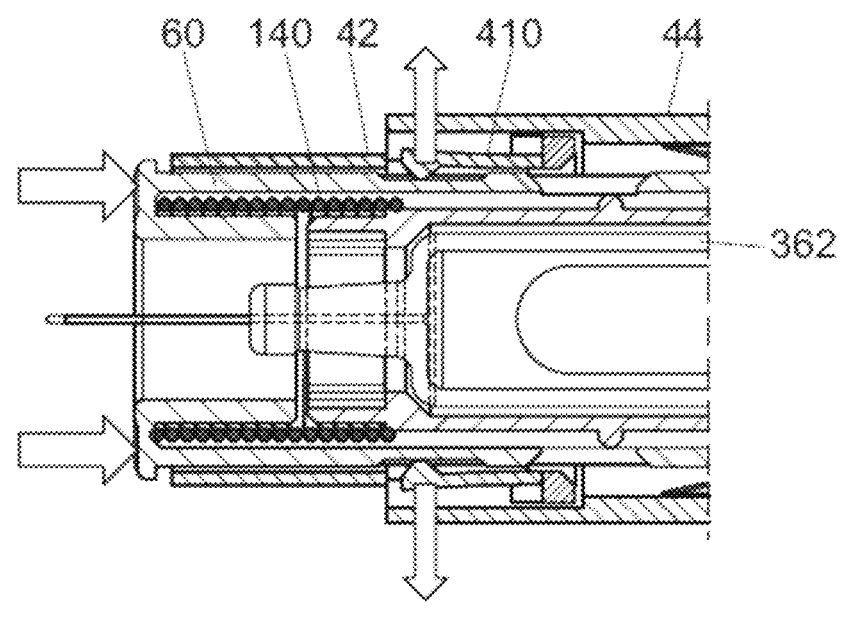
Fig. 118
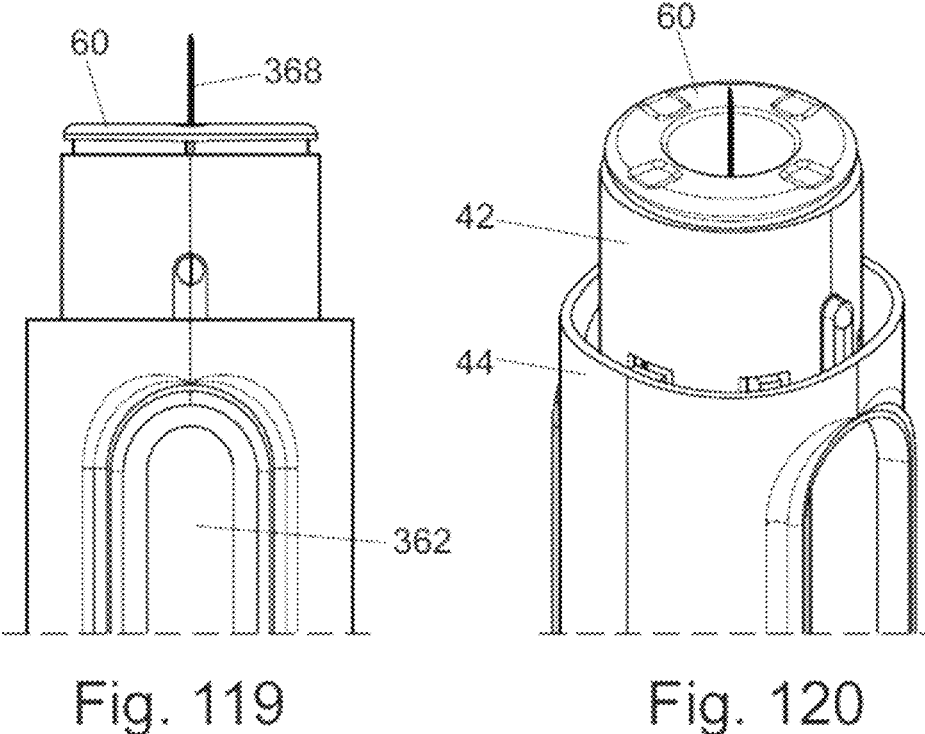
Fig. 119                    Fig. 120

384

386

384

380

390

394

229

388

380

220

500

504

MEDICAMENT DELIVERY MEMBER GUARD LOCK ASSEMBLY

CROSS REFERENCE TO RELATED APPLICATIONS

The present application is a U.S. National Phase application pursuant to 35 U.S.C. § 371 of International Application No. PCT/EP2021/078113 filed Oct. 12, 2021, which claims priority to European Patent Application No. 20201659.8 filed Oct. 14, 2020 and European Patent Application No. 21172824.1, filed May 7, 2021. The entire disclosure contents of these applications are herewith incorporated by reference into the present application.

TECHNICAL FIELD

The present disclosure concerns medicament delivery member guard lock assemblies, and particularly medicament delivery member guard lock assemblies comprising a housing, a medicament delivery member guard, a lock activation sleeve and a medicament delivery member guard lock.

BACKGROUND

Medicament delivery devices such as autoinjectors can include a needle guard lock which stops the needle guard from being retracted again after use of the autoinjector, so as to reduce needle stick injuries. However, the needle guard lock can be relatively flimsy, in which case the lock could potentially be broken if the needle guard is pushed hard. Considering this, the applicant has appreciated that development of more robust needle guard locks would be beneficial.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the axial direction (longitudinal direction).

A first aspect of the present disclosure concerns a medicament delivery member guard lock assembly for a medicament delivery device, the medicament delivery member guard lock assembly comprising: a housing extending along an axis in an axial direction from a proximal end to a distal end, the housing comprising a recess or a slit; a medicament delivery member guard slidably arranged in the housing, the medicament delivery member guard extending from a proximal end to a distal end; a lock activation sleeve slidably arranged in the housing at the distal end of the medicament delivery member guard; and a medicament delivery member guard lock arranged in the housing adjacent to the lock activation sleeve. The medicament delivery member guard lock comprises a base and a flexible arm pivotally attached to the base, wherein the arm comprises a proximal part and a distal part, wherein the arm is attached to the base between the proximal part and the distal part, and wherein the proximal part of the arm is arranged adjacent to the recess or slit in the housing. By being slidably arranged in the housing, the medicament delivery member guard can be attached to the housing and moveable relative to the housing in the axial direction. Similarly, the lock activation sleeve can be moveable relative to the housing in the axial direction by being slidably arranged in the housing.

A medicament delivery member guard lock assembly structured in this way can provide a robust needle guard lock, for example for a single-use disposable autoinjector. This can be useful for any drug viscosity, but can be particularly useful in devices for injecting high viscosity liquids, for example liquids above 30 cP, liquids above 50 cP, liquids between 30 and 150 cP, liquids between 30 and 100 cP, or liquids between 30 and 50 cP.

The medicament delivery member guard lock assembly can avoid the need for a compromise between activation force (i.e. force needed to push the medicament delivery member guard back) and the strength of the lockout mechanism.

Optionally, the medicament delivery member guard comprises a distally facing surface and the lock activation sleeve comprises a corresponding proximally facing surface with which the distally facing surface of the medicament delivery member guard engages so as to push the lock activation sleeve in the distal direction when the medicament delivery member guard is pushed in the distal direction.

Optionally, the lock activation sleeve comprises a radially facing surface relative to the axis, with which radially facing surface the distal part of the flexible arm of the medicament delivery member guard lock is pushed in the radial direction to bias the flexible arm of the medicament delivery member guard lock against the medicament delivery member guard lock when the lock activation sleeve is pushed in the distal direction.

Optionally, when the medicament delivery member guard is subsequently moved back in the proximal direction, the proximal part of the flexible arm of the medicament delivery member guard lock moves towards or into the recess or slit in the housing.

Optionally, the medicament delivery member guard is configured to push the lock activation sleeve in the distal direction when the medicament delivery member guard is pushed in the distal direction. Optionally, the lock activation sleeve is configured to push the distal part of the flexible arm of the medicament delivery member guard lock in the radial direction relative to the axis to bias the flexible arm when the lock activation sleeve is pushed in the distal direction. Optionally, when the medicament delivery member guard is subsequently moved back in the proximal direction, the proximal part of the arm of the medicament delivery member guard lock moves towards or into the recess or slit in the housing.

Optionally, the proximal part of the flexible arm of the medicament delivery member guard lock comprises a protrusion extending in the radial direction. This can help the medicament delivery member guard lock engage with the recess or slit in the housing. Optionally, the protrusion extends away from the axis.

Optionally, the base of the medicament delivery member guard lock is tubular. Optionally, the lock activation sleeve is tubular. Optionally, at least part of the arm of the medicament delivery member guard lock is further from the axis than the base. Optionally, a pivot extends between the base of the lock activation sleeve and the lock activation sleeve arm.

Optionally, the medicament delivery member guard lock comprises a concertina section, the concertina section having a variable length in the axial direction, and the concertina section extending in the axial direction from the proximal end of the medicament delivery member guard lock. Optionally, the concertina section comprises a support portion spaced apart from the base of the medicament delivery member guard lock and at least one arm, the arm extending from the base of the medicament delivery member guard lock to the support portion.

Optionally, the medicament delivery member guard lock (typically the base of the medicament delivery member guard lock) is directly or indirectly fixed to the housing, and can be immovable relative to the housing. Optionally, the distal end 113 of the distal part 108 of the arm is further from the axis 20 than the proximal end 109 of the distal part 108 of the arm. Optionally, the distal part 108 of the arm comprises a protrusion 111. The protrusion 111 can help hold the lock activation sleeve, and therefore also the arm, in position before injection.

Optionally, the medicament delivery member guard comprises a proximal portion and a distal portion, wherein the proximal portion is tubular and the distal portion comprises an arm. Optionally, the arm of the medicament delivery member guard comprises a recess or slit extending in the axial direction. This recess or slit can receive the arm of the medicament delivery member guard lock during injection, and can reduce the strain on the arm. It can also potentially allow for a stronger arm, as the arm may need to flex less.

Optionally, the radially facing surface of the lock activation sleeve faces towards the axis 20. Optionally, the distally facing surface of the medicament delivery member guard and the proximally facing surface of the lock activation sleeve are spaced apart in the axial direction. This can help avoid activation of a medicament delivery device if the medicament delivery device is dropped.

In a second aspect of the present disclosure, a medicament delivery device comprising any medicament delivery member guard lock assembly described above is provided. Optionally, the medicament delivery member guard lock assembly comprises a medicament delivery member guard spring, which is typically arranged between the medicament delivery member guard and the housing or a syringe holder. Optionally, the medicament delivery device comprises a medicament delivery member. Optionally, the medicament delivery member is a needle or a jet injector. Optionally, the medicament delivery device comprises a plunger rod extending through the medicament delivery member guard lock and the lock activation sleeve. Optionally, the medicament delivery device comprises a driver nut with a screw thread, wherein the plunger rod is threaded to engage the screw thread on the driver nut. Optionally, the medicament delivery device comprises a driver to drive the plunger rod. Optionally, the medicament delivery device is an autoinjector or a pen injector.

A third aspect of the present disclosure concerns a method of using a medicament delivery member guard lock assembly, the medicament delivery member guard lock assembly comprising a tubular housing with a recess or a slit, the tubular housing extending from a proximal end to a distal end along an axis, a medicament delivery member guard slidably arranged in the tubular housing, a lock activation sleeve slidably arranged in the tubular housing, and a medicament delivery member guard lock arranged in the tubular housing, the medicament delivery member guard lock comprising a base and a flexible arm pivotably attached to the base, wherein the flexible arm is pivotably attached to the base between a proximal part of the flexible arm and a distal part of the flexible arm, the method comprising the steps of: pushing the medicament delivery member guard in the distal direction relative to the tubular housing and thereby pushing the lock activation sleeve in the distal direction relative to the tubular housing so that the lock activation sleeve pushes the distal part of the flexible arm of the medicament delivery member guard lock towards the axis and biases the proximal part of the flexible arm of the medicament delivery member guard lock away from the axis; and releasing the medicament delivery member guard so that the medicament delivery member guard moves in the proximal direction, thereby allowing the biased proximal part of the medicament delivery member guard lock to move away from the axis and towards the recess or slit in the tubular housing. The advantages of this method are similar to the advantages described for the medicament delivery member guard lock assembly described above.

Optionally, when the biased proximal part of the medicament delivery member guard lock moves away from the axis, a part of the proximal part of the medicament delivery member guard lock moves into the recess or slit in the housing.

A fourth aspect of the present disclosure concerns a medicament delivery member guard lock assembly configured to carry out any of the methods described above in the third aspect.

A fifth aspect of the present disclosure concerns a medicament delivery member guard lock assembly for an autoinjector, the medicament delivery member guard lock assembly comprising a housing, a medicament delivery member guard, a lock activation sleeve, and a medicament delivery member guard lock, wherein the housing, the medicament delivery member guard, the lock activation sleeve and the medicament delivery member guard lock are arranged relative to one another so that movement of the medicament delivery member guard in a distal direction pushes the lock activation sleeve in the distal direction, which in turn pushes a portion of the medicament delivery member guard lock in a direction perpendicular to the axial direction, and wherein when the medicament delivery member guard is subsequently moved in the proximal direction, a portion of the medicament delivery member guard lock moves perpendicular to the axial direction to restrict the medicament delivery member guard from moving in the distal direction.

A sixth aspect of the present disclosure concerns a medicament delivery member guard lock assembly for an autoinjector, the medicament delivery member guard lock assembly comprising: a housing extending in an axial direction from a proximal end to a distal end; a medicament delivery member guard moveable in the axial direction relative to the housing from a first position to a second position to a third position; a lock activation sleeve moveable in the axial direction relative to the housing from a first position to a second position; and a medicament delivery member guard lock with an arm moveable relative to the housing from a first position to a second position to a third position, wherein in an initial state prior to use of the medicament delivery member guard lock assembly, the medicament delivery member guard is in the first position, the lock activation sleeve is in the first position, and the medicament delivery member guard lock arm is in the first position, wherein in an intermediate state, the medicament delivery member guard is in the second position, the lock activation sleeve is in the second position, and the medicament delivery member guard lock arm is in the second position, and wherein in a final state, the medicament delivery member guard is in the third position, the lock activation sleeve is in the second position, and the medicament delivery member guard lock arm is in the third position. All the positions listed above are typically different from one another, but this is not essential; for example, the first and third positions for the medicament delivery member guard may be the same.

A seventh aspect of the present disclosure concerns a medicament delivery member guard lock assembly for a medicament delivery device, the medicament delivery member guard lock assembly comprising: a tubular housing extending along an axis in an axial direction from a proximal end to a distal end; a medicament delivery member guard slidably arranged in the proximal end of the housing, the medicament delivery member guard extending from a proximal end to a distal end, the medicament delivery member guard comprising a distally facing surface; a lock activation sleeve slidably arranged in the housing, the lock activation sleeve comprising a proximally facing surface configured to engage the distally facing surface of the medicament delivery member guard; and a medicament delivery member guard lock arranged in the housing, wherein the medicament delivery member guard lock is fixed relative to the housing, wherein the medicament delivery member guard lock comprises a base and an arm extending from a proximal end to a distal end, wherein the arm is pivotably attached to the base between the proximal end and the distal end.

A eighth aspect of the present disclosure concerns a medicament delivery member guard lock for a medicament delivery device, the medicament delivery member guard lock extending along an axis in an axial direction from a proximal end to a distal end, the medicament delivery member guard lock comprising a base and a flexible arm pivotally attached to the base, wherein the arm comprises a proximal part and a distal part, and the arm is attached to the base between the proximal part and the distal part, and wherein the distal part of the arm is configured to be biased towards the axis, and wherein the proximal part of the arm is configured to be biased away from the axis when the distal part of the arm is biased towards the axis. Any combination of the optional features of the medicament delivery member guard lock as described above for medicament delivery member guard lock assembly of the first aspect may also be included in this the medicament delivery member guard lock.

An ninth aspect of the present disclosure concerns a driver nut for a medicament delivery device, the driver nut comprising a base, an arm attached to the base, the arm being configured to engage a lock activation sleeve and to engage a driver to lock a medicament delivery device before use of said medicament delivery device, and a screw thread attached to the base, the screw thread being configured to engage a corresponding screw thread on a plunger rod to guide said plunger rod in a proximal direction during use of said medicament delivery device.

A tenth aspect of the present disclosure concerns an activation sub-assembly for a medicament delivery device, the activation sub-assembly comprising a plunger rod, a medicament delivery member guard lock according to the seventh aspect, a driver nut according to the ninth aspect, and a lock activation sleeve comprising a radially facing surface configured to engage the distal part of the arm of the medicament delivery device guard lock. Optionally, the activation sub-assembly comprises a thrust bearing attached to the proximal end of the plunger rod.

A eleventh aspect of the present disclosure concerns a powerpack sub-assembly for a medicament delivery device, the powerpack sub-assembly comprising a powerpack housing, a driver, a torsion spring attached to the powerpack housing and the driver, and a powerpack lock, wherein in a first position the powerpack lock is rotationally locked relative to the powerpack housing and the driver is free to rotate relative to the powerpack housing to tension the torsion spring, and wherein in a second position the powerpack lock is rotationally locked relative to the powerpack housing and the driver, and the torsion spring is tensioned. Optionally, in a third position the powerpack lock is rotationally locked relative to the driver and the powerpack lock is free to rotate relative to the powerpack housing.

An twelfth aspect of the present disclosure concerns a rear sub-assembly for a medicament delivery device, the rear sub-assembly comprising a powerpack sub-assembly according to the eleventh aspect and an activation sub-assembly according to the tenth aspect.

A thirteenth aspect of the present disclosure concerns a medicament delivery device sub-assembly comprising a driver to drive a plunger rod and a driver nut, wherein the driver comprises teeth and the driver nut comprises corresponding teeth, so that an indication such as an audible or tactile indication is given when the driver rotates relative to the driver nut during medicament delivery.

A fourteenth aspect of the present disclosure concerns a medicament delivery device sub-assembly comprising a driver to drive a plunger rod and a powerpack lock, wherein the driver and the powerpack lock comprise corresponding protrusions that engage each other so that an indication, for example an audible or tactile indication, is given when the driver rotates relative to the powerpack lock during medicament delivery.

A fifteenth aspect of the present disclosure concerns a medicament delivery device sub-assembly comprising a spinner, wherein the spinner is attached to a component that is configured to rotate during medicament delivery, so that the spinner rotates when the component rotates during medicament delivery to provide an indication of medicament delivery, for example a visual, audible or tactile indication. Optionally, the component rotates relative to a housing. Optionally, the component that is designed to rotate during medicament delivery is a plunger rod or a driver for driving a plunger rod.

A sixteenth aspect of the present disclosure concerns a medicament delivery device, for example an autoinjector or a pen injector, comprising the contents of one or more of the fourth to fifteenth aspects.

Another aspect concerns a lock mechanism for a medicament delivery device, the lock mechanism extending from a proximal end to a distal end in an axial direction relative to a longitudinal axis, the lock mechanism comprising a housing, a medicament delivery member guard and a cap, wherein one of the medicament delivery member guard and the housing comprises a flexible arm, the flexible arm comprising a protrusion extending in a radial direction relative to the longitudinal axis, wherein the other of the medicament delivery member guard and the housing comprises a recess or cut-out, wherein part of the flexible arm is in the recess or cut-out, wherein the flexible arm is between the cap and the other of the medicament delivery member guard and the housing, and wherein the cap is adjacent to the flexible arm in a radial direction relative to the longitudinal axis. This can lock a medicament delivery device from activation prior to removal of the cap. This can allow for a needle spring, which might otherwise need to be stronger to stop a device from activating upon being dropped, to be weaker, potentially allowing for a lower activation force and thereby making medicament delivery easier for an end user. This can be particularly relevant in some user groups where grip strength is low, for example.

Optionally, the housing extends around the medicament delivery member guard. Optionally, the housing comprises the flexible arm and the medicament delivery member guard comprises the recess or cut-out. Optionally, the proximal end of the cut-out or recess is spaced apart in the longitudinal direction from the protrusion. This can help by reducing the force required to start movement of the medicament delivery guard. Optionally, the recess or cut-out is a first recess or cut-out, and the other of the medicament delivery member guard and the housing comprises a second recess or cut-out that is closer to the proximal end than the first recess or cut-out. This can reduce friction. Optionally, the second recess or cut-out is aligned with the first recess or cut-out in the direction of the longitudinal axis. Optionally, the cap, the housing and the medicament delivery member guard are arranged so that prior to removal of the cap, the housing is blocked from moving in the radial direction and the medicament delivery member guard is thereby blocked from moving in the distal direction, and so that after removal of the cap, the housing can move in the radial direction and the medicament delivery member guard can therefore push the housing in the radial direction to move past the housing in the distal direction. Optionally, the part of the arm that is in the recess or cut-out is the protrusion.

Another aspect concerns a lock mechanism for a medicament delivery device, the lock mechanism extending from a proximal end to a distal end in an axial direction relative to a longitudinal axis, the lock mechanism comprising a housing, a medicament delivery member guard and a cap, wherein one of the medicament delivery member guard and the cap comprises a protrusion extending in a radial direction relative to the longitudinal axis, wherein the other of the medicament delivery member guard and the cap comprises a recess or cut-out, wherein the protrusion is in the recess or cut-out, wherein the medicament delivery member guard is moveable in the direction of a longitudinal axis relative to the housing from a locked position to an unlocked position, wherein in the locked position, movement of the protrusion relative to the recess or cut-out is restricted by a wall of the housing, and in the unlocked position, the movement of the protrusion relative to the recess or cut-out is no longer restricted by the wall of the housing, thereby allowing the protrusion to be moved out of the recess or cut-out and the cap to be removed from the medicament delivery member guard. This can lock a medicament delivery device from activation prior to removal of the cap. This can allow for a needle spring, which might otherwise need to be stronger to stop a device from activating upon being dropped, to be weaker, potentially allowing for a lower activation force and thereby making medicament delivery easier for a user. This can be particularly relevant in some user groups where grip strength is low, for example.

Optionally, at least one of the cap and the medicament delivery member guard comprises a flexible portion. Optionally, the flexible portion is a flexible arm of the cap. Optionally, the recess or cut-out is in the flexible arm. Optionally, the cap comprises a cap housing and a cap insert, and the cap insert is rotatable relative to the cap body. Optionally, the cap insert is attached to the cap body by a snap fit that restricts movement of the cap insert relative to the cap body in the axial direction. Optionally, the rotational movement of the cap insert relative to the cap body is limited by a rib extending from the cap body. Optionally, the cap comprises a distally facing surface abutting a proximally facing surface of the housing. Optionally, the distally facing surface of the cap and the proximally facing surface of the housing each describe a sinusoidal pattern in a circumferential direction relative to the longitudinal axis. Optionally, the wall of the housing faces in the radial direction. Optionally, the wall of the housing faces towards the axis.

Optionally, the cap comprises a medicament delivery member guard remover, preferably a rigid medicament delivery member guard remover.

Another aspect concerns a medicament delivery device comprising a lock mechanism as described above. Optionally, the medicament delivery device is an autoinjector. Optionally, the medicament delivery device comprises a powerpack inside the housing and a primary package inside the housing. Optionally, the medicament delivery device comprises a housing, and the protrusion and/or the flexible arm is inside the housing. Optionally, a proximal end of the protrusion and/or a proximal end of the flexible arm is distal to the proximal end of the housing.

Another aspect concerns a lock mechanism for a medicament delivery device, the lock mechanism extending from a proximal end to a distal end in an axial direction relative to a longitudinal axis, the lock mechanism comprising a housing, a needle guard (or more generally a medicament delivery member guard) and a cap, wherein preferably at least one of the housing, the needle guard and the cap body have a flexible arm, wherein interaction between the housing, the needle guard and the cap limits distal movement of the needle guard before the cap is removed, and wherein the needle guard is free to move in the distal direction after the cap is removed. Optionally, the flexible arm is a seesaw. Optionally, the cap comprises a cap body and a needle guard remover. Optionally, a proximal end of the seesaw comprises a protrusion and the cap comprises a corresponding protrusion, so that when the needle guard is moved in the distal direction relative to the cap, the protrusion of the cap engages the protrusion of the needle guard and pivots the seesaw, wherein pivoting the seesaw results in a distal end of the seesaw moving in the radial direction relative to the axis, aligning a proximally facing surface of the distal end of the seesaw with a distally facing surface of the housing. Optionally, the distally facing surface of the housing is further from the longitudinal axis than the proximally facing surface of the seesaw is from the longitudinal axis.

Another aspect concerns a lock mechanism for a medicament delivery device, the lock mechanism comprising a housing, a needle guard (or more generally a medicament delivery member guard) and a cap, wherein the lock mechanism comprises a recess or a cut-out, wherein the lock mechanism comprises a protrusion that extends into the recess or cut-out, wherein the lock mechanism comprises a flexible portion, wherein the lock mechanism can move between a locked position and an unlocked position, wherein in the locked position, the protrusion is restricted from leaving the recess or cut-out as movement of the flexible portion is restricted, and wherein in the unlocked position, the protrusion is able to leave the recess or cut-out by movement of the flexible portion. Optionally, the cap comprises a cap housing and a needle guard remover.

Another aspect of the present disclosure concerns a lock mechanism for a medicament delivery device, the lock mechanism comprising a housing, a needle guard and a cap. The lock mechanism extends from a proximal end to a distal end in an axial direction relative to a longitudinal axis. This can lock a medicament delivery device from activation prior to removal of the cap. This can allow for a needle spring, which might otherwise need to be stronger to stop a device from activating upon being dropped, to be weaker, potentially allowing for a lower activation force and thereby making medicament delivery easier for a user. This can be particularly relevant in some user groups where grip strength is low, for example.

Optionally, at least one of the housing, the needle guard and the cap body have a flexible arm, wherein interaction between the housing, the needle guard and the cap limits distal movement of the needle guard before the cap is removed, and wherein the needle guard is free to move in the distal direction after the cap is removed.

Optionally, one of the needle guard and the cap comprises a protrusion extending in a radial direction relative to the longitudinal axis, wherein the other of the needle guard and the cap comprises a recess or cut-out, wherein part of the arm (for example the protrusion) is in the recess or cut-out, wherein the needle guard is moveable in the direction of a longitudinal axis relative to the housing from a locked position to an unlocked position, wherein in the locked position, movement of the protrusion relative to the recess or cut-out is restricted by a wall of the housing, and in the unlocked position, the movement of the protrusion relative to the recess or cut-out is no longer restricted by the wall of the housing, thereby allowing the protrusion to be moved out of the recess or cut-out and the cap to be removed from the needle guard.

Optionally, one of the needle guard and the housing comprises a flexible arm, the flexible arm comprising a protrusion extending in a radial direction relative to the longitudinal axis, wherein the other of the needle guard and the housing comprises a recess or cut-out, wherein the arm (for example a protrusion of the arm) extends into the recess or cut-out, wherein the flexible arm is between the cap and the other of the needle guard and the housing, and wherein the cap is adjacent to the protrusion in a radial direction relative to the longitudinal axis.

Optionally, the lock mechanism comprises a recess or a cut-out, wherein the lock mechanism comprises a protrusion that extends into the recess or cut-out, the lock mechanism comprises a flexible portion, and the lock mechanism can move between a locked position and an unlocked position, wherein in the locked position, the protrusion is restricted from leaving the recess or cut-out as movement of the flexible portion is restricted, and wherein in the unlocked position, the protrusion is able to leave the recess or cut-out by movement of the flexible portion.

Another aspect of the present disclosure concerns a tool for medicament delivery device assembly, the tool comprising a distal end tool and a proximal end tool, wherein the distal end tool can rotate relative to the proximal end tool, wherein the distal end tool is configured to receive and rotationally lock to a portion of a powerpack of said medicament delivery device such as a powerpack lock and/or a powerpack housing, and wherein the proximal end tool is configured to receive and rotationally lock to another portion of said medicament delivery device such as a lock activation sleeve.

Another aspect of the present disclosure concerns a method for assembling a medicament delivery device, the method comprising the steps of inserting a first powerpack sub-assembly into a distal end tool of a tool for medicament delivery device assembly, inserting a torsion spring on to the first powerpack sub-assembly, inserting a second powerpack sub-assembly on to the torsion spring, inserting a proximal end tool of said tool for medicament delivery device assembly on to the second powerpack sub-assembly, and rotating the first powerpack sub-assembly relative to the second powerpack sub-assembly to wind the torsion spring.

Another aspect of the present disclosure concerns a cap for a medicament delivery device, the cap comprising a cap housing, a pull strap attached to the cap housing and an arm extending from the cap housing.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings as listed below.

FIG. 43 shows a cross-sectional view of part of the autoinjector of FIG. 29 during injection.

FIG. 44 shows a cross-sectional view of some components of the autoinjector of FIG. 29 after use.

FIG. 45 shows a perspective and partially cross-sectional view of some components of the autoinjector of FIG. 29 after use.

FIG. 74 shows a perspective and partially cross-section view of part of the powerpack lock and the spinner of FIG. 71.

FIG. 75 shows a perspective view of a distal portion of the autoinjector of FIG. 70.

FIG. 76 shows a cross-section view of the autoinjector of FIG. 70.

FIG. 88 shows a perspective view of the needle guard of FIG. 86.

FIG. 89 shows a perspective view of part of another example autoinjector.

FIG. 90 shows a side view of the cap of the autoinjector of FIG. 89.

FIGS. 113, 114 and 115 each show two different perspective views of components from FIG. 100, namely the cap housing, cap insert and proximal housing respectively.

FIGS. 118, 119 and 120 show different views of the front sub-assembly of the autoinjector of FIG. 99 after the cap has been removed and after the needle guard has been pushed in the distal direction relative to the housing.

FIG. 127 shows a perspective view of the spinner of FIG. 121.

FIG. 128 shows a perspective view of part of the spinner cap of FIG. 121.

FIGS. 129 and 130 show perspective views of another feedback mechanism.

DETAILED DESCRIPTION

Figures 1, 2:
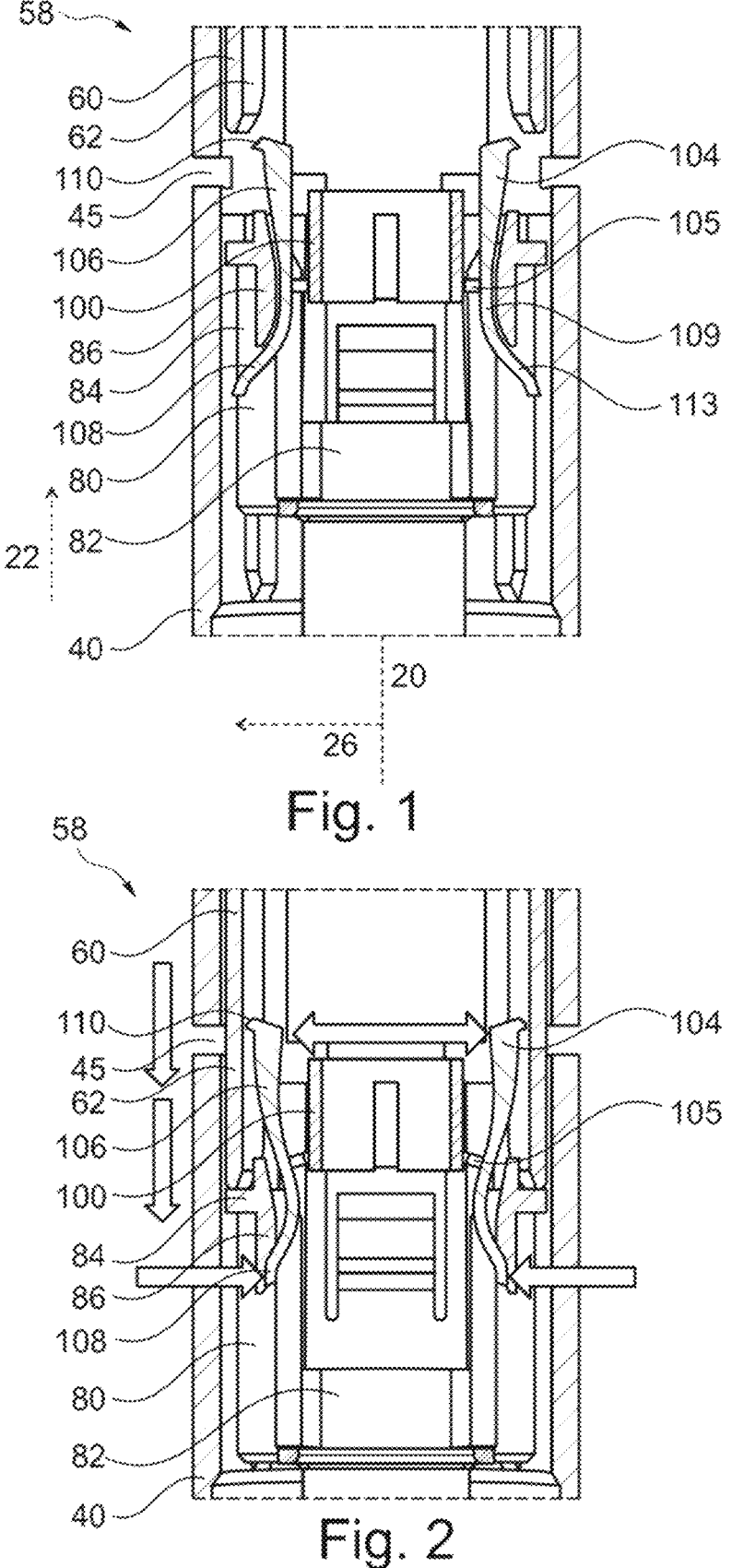
FIG. 1 shows a cross-section of part of an autoinjector showing a needle guard lock assembly before use of the autoinjector.
FIG. 2 shows the components in FIG. 1 during injection.

This application describes various concepts, as summarised in the summary of the present disclosure above. Initially, a needle guard lock assembly will be described. Example autoinjectors will then be described. These autoinjectors can include concepts such as the described needle guard lock assembly and can therefore help put the various concepts, such as the needle guard lock assembly in context.

In one aspect, a medicament delivery member guard lock assembly (58) for a medicament delivery device (10) is described, the medicament delivery member guard lock assembly (58) comprising: a housing (40) extending along an axis (20) in an axial direction (22) from a proximal end (14) to a distal end (16), the housing (40) comprising a recess or a slit (45); a medicament delivery member guard (60) slidably arranged in the housing (40), the medicament delivery member guard (60) extending from a proximal end (14) to a distal end (16); a lock activation sleeve (80) slidably arranged in the housing (40) at the distal end (16) of the medicament delivery member guard (60); and a medicament delivery member guard lock (100) arranged in the housing (40) adjacent to the lock activation sleeve (80), wherein the medicament delivery member guard lock (100) comprises a base (102) and a flexible arm (104) pivotally attached to the base (102), wherein the flexible arm (104)

comprises a proximal part (106) and a distal part (108), wherein the flexible arm (104) is attached to the base (102) between the proximal part (106) and the distal part (108), and wherein the proximal part (106) of the flexible arm (104) is arranged adjacent to the recess or slit (45) in the housing (40).

FIG. 1 shows part of an autoinjector 10, the autoinjector comprising a housing 40, a needle guard (needle cover) 60, a lock activation sleeve 80 and a needle guard lock 100.

The housing 40 includes two slits 45 opposite one another relative to the axis (central axis) 20. The slits 45 extend through the housing 40 in the radial direction 26. The needle guard 60, the lock activation sleeve 80 and the needle guard lock 100 are all inside the housing 40.

The needle guard 60 comprises two arms 62 extending inside the housing.

The lock activation sleeve 80 comprises a tubular section 82 and two arms 84. Each arm comprises a radially facing surface, in this case a pad 86 facing towards the axis 20.

The needle guard lock 100 comprises a base (tubular section 102 in this example) and two arms 104. The arms are flexible, and are attached to the tubular section 102 between a proximal part 106 and a distal part 108 of the arm 104. A proximal portion of the proximal part 106 of the arm, which in this case is also the most proximal portion of the arm, is shaped to engage with the slit in the housing, in this case with protrusion 110.

With reference to FIGS. 1 to 4, the relative movement of the different parts during use will now be described. FIG. 1 shows the initial position before use (and before activation) of the autoinjector. This is the position in which the autoinjector would typically be kept in between final assembly and use, for example during shipment and storage. FIG. 2 shows the autoinjector 10 after the needle guard 60 has been moved in the distal direction (normally by initiation of an injection). The distal movement of the needle guard 60 also pushes the lock activation sleeve 80 in the distal direction as well. Moving the lock activation sleeve 80 in the distal direction results in the pad 86 of the lock activation sleeve engaging with the distal part 108 of the arm 104 of the needle guard lock and pushing the distal part 108 of the arm 104 towards the axis 20. The proximal part 106 of the arm 104 would pivot accordingly and move away from the axis 20, but the needle guard 60 stops this. As a result, the arm 104 is biased and is pushing (away from the axis) on the needle guard 60.

Figure 3:
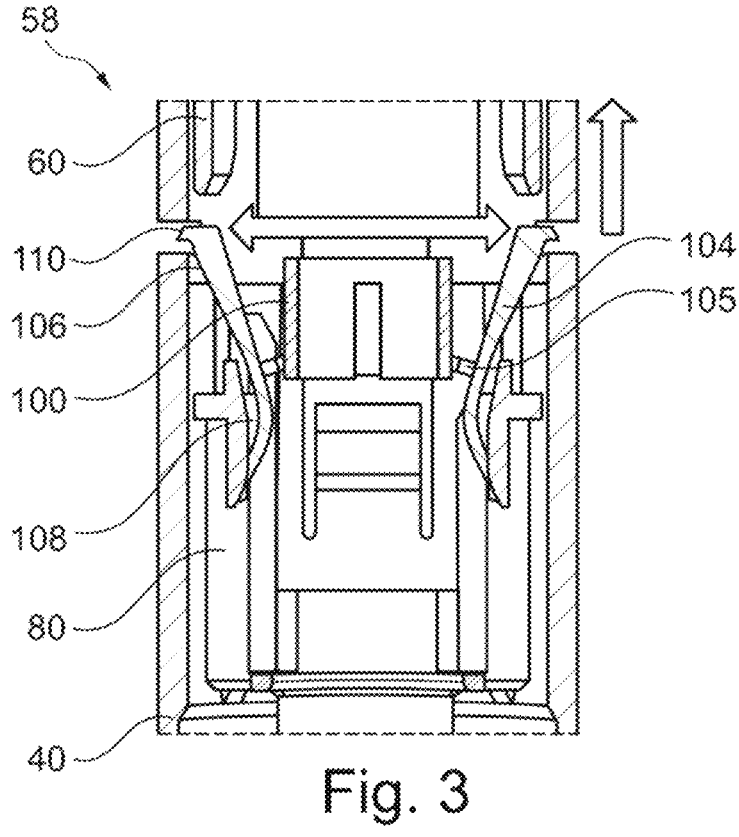
FIG. 3 shows the components in FIG. 1 after injection.

Once the needle guard is allowed to move in the distal direction again (typically once the injection is finished, though this could also be earlier in the case of a premature lifting of the needle guard from an injection site), the needle guard moves back in the proximal direction to a position as shown in FIG. 3 (in this case, the final position after injection is the same as the initial position before injection, though this is optional). The lock activation sleeve, however, does not move back to its original position and therefore the pad 86 is still pushing the distal part 108 of the arm 104 towards the axis 20. To release the resulting tension in the arm 104 as mentioned above, the proximal part 106 of the arm 104 moves away from the axis 20 once the needle guard 60 is no longer impeding it. The proximal part 106 of the arm 104 (or specifically in this example the protrusion 110 on the proximal part of the arm 104) ends up in (or adjacent to) the slit 45 in the housing 40. The arm may remain in tension after injection so that it holds the lock activation sleeve 80 in place by friction, although another feature or features elsewhere on the device could additionally or alternatively hold the lock activation sleeve in place.

Figure 4:
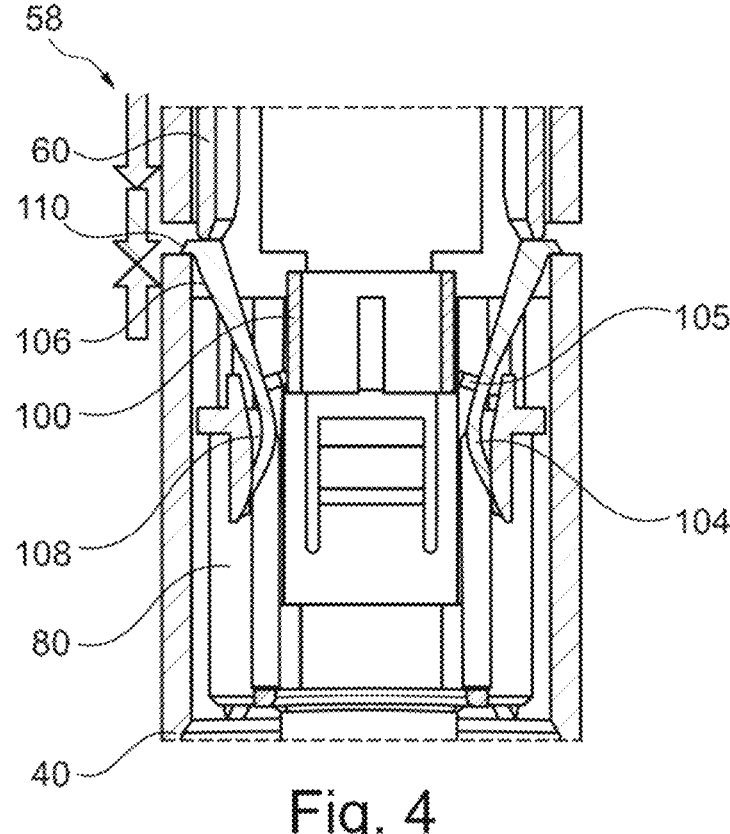
FIG. 4 shows the components in FIG. 1 when an attempt is made to retract the needle guard again after injection.

FIG. 4 shows what happens if an attempt is made to push the needle guard 60 back in the distal direction after the lock created by the needle guard lock 100 has been set. In this example, the needle guard 60 can move back in the distal direction a short way (this gap between the arm 104 and the needle guard 60 as shown in FIG. 3 is optional but preferable, as it allows for greater manufacturing tolerance during component manufacture and assembly), but is then stopped from moving further in the distal direction by the arm 104 of the needle guard lock 100. The arm 104 is supported in the slit 45 by the protrusion 110.

Figure 5:
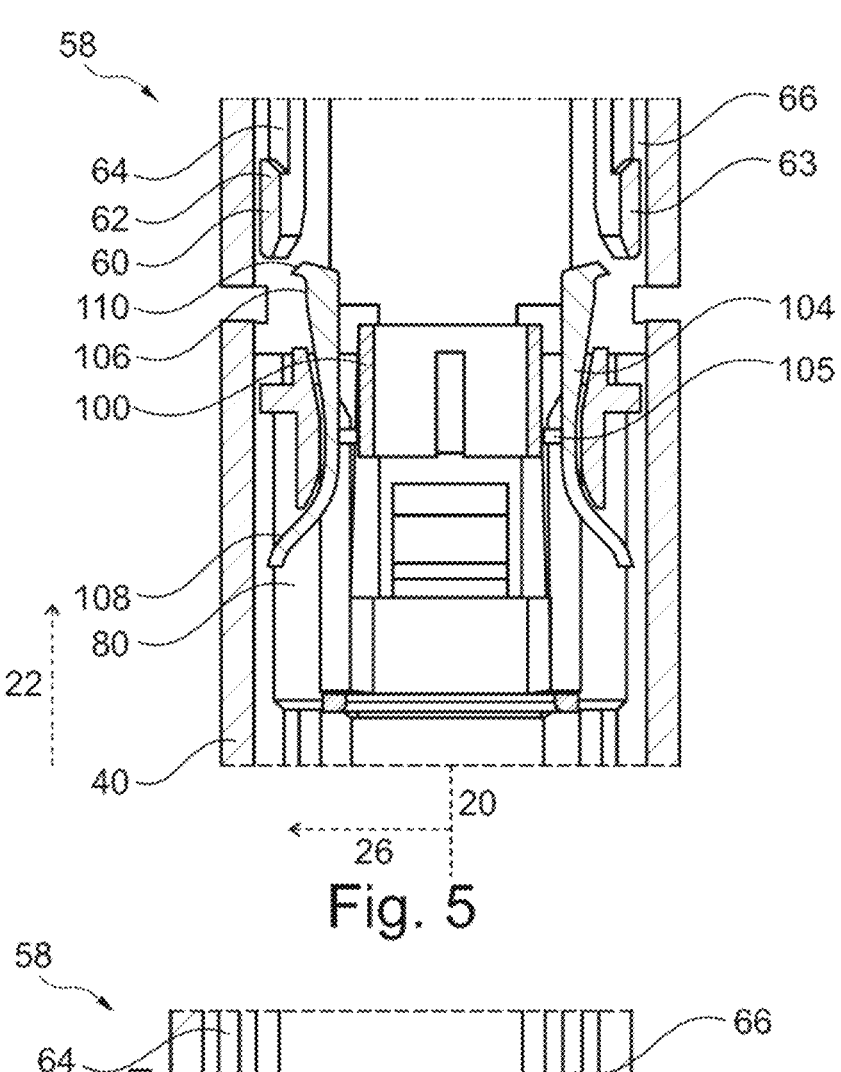
FIG. 5 shows a cross-section of part of an autoinjector showing a needle guard lock assembly before use of the autoinjector.
Figure 6:
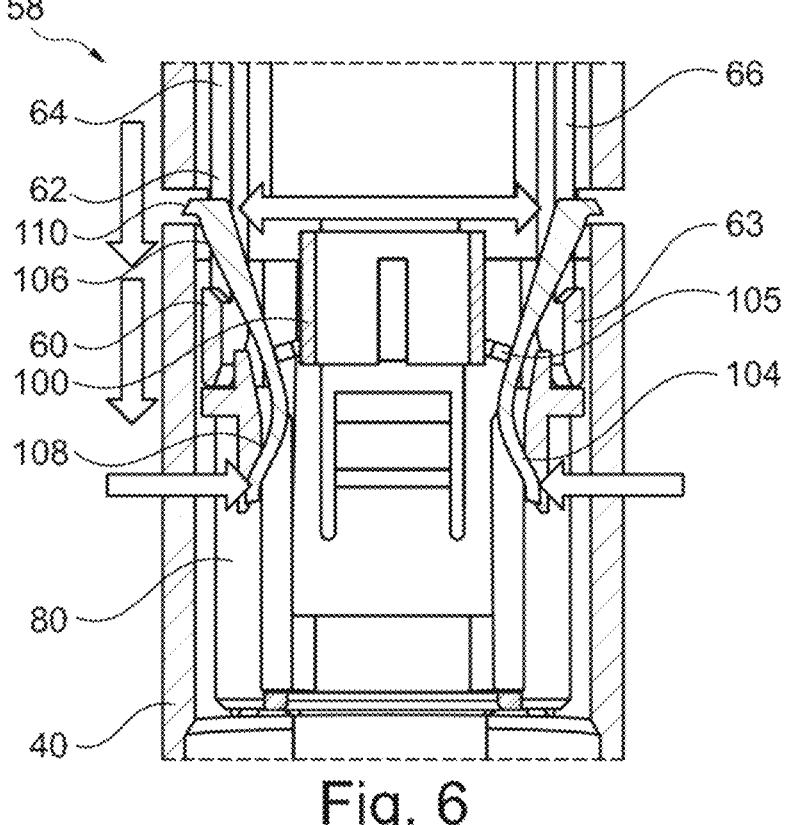
FIG. 6 shows the components in FIG. 5 during injection.
Figure 7:
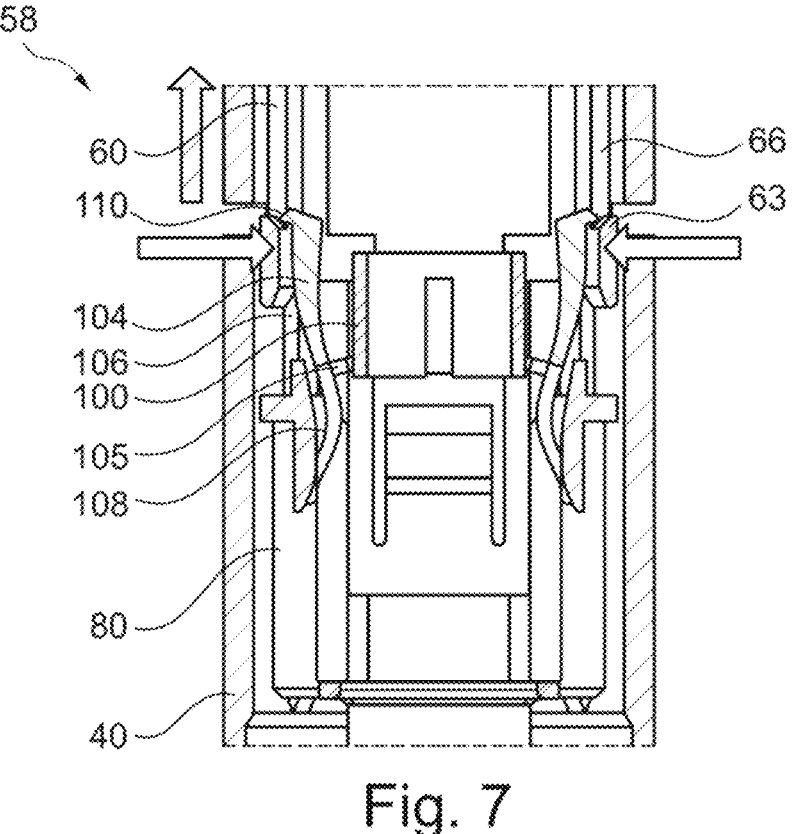
FIG. 7 shows the components in FIG. 5 during needle guard return after the injection.
Figure 8:
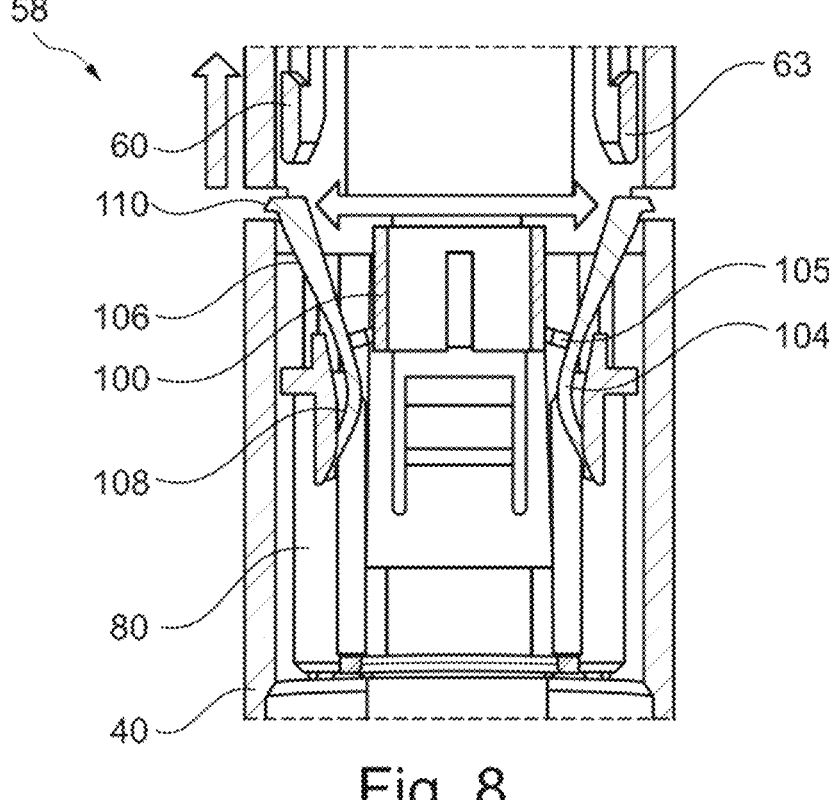
FIG. 8 shows the components in FIG. 5 after injection.
Figure 9:
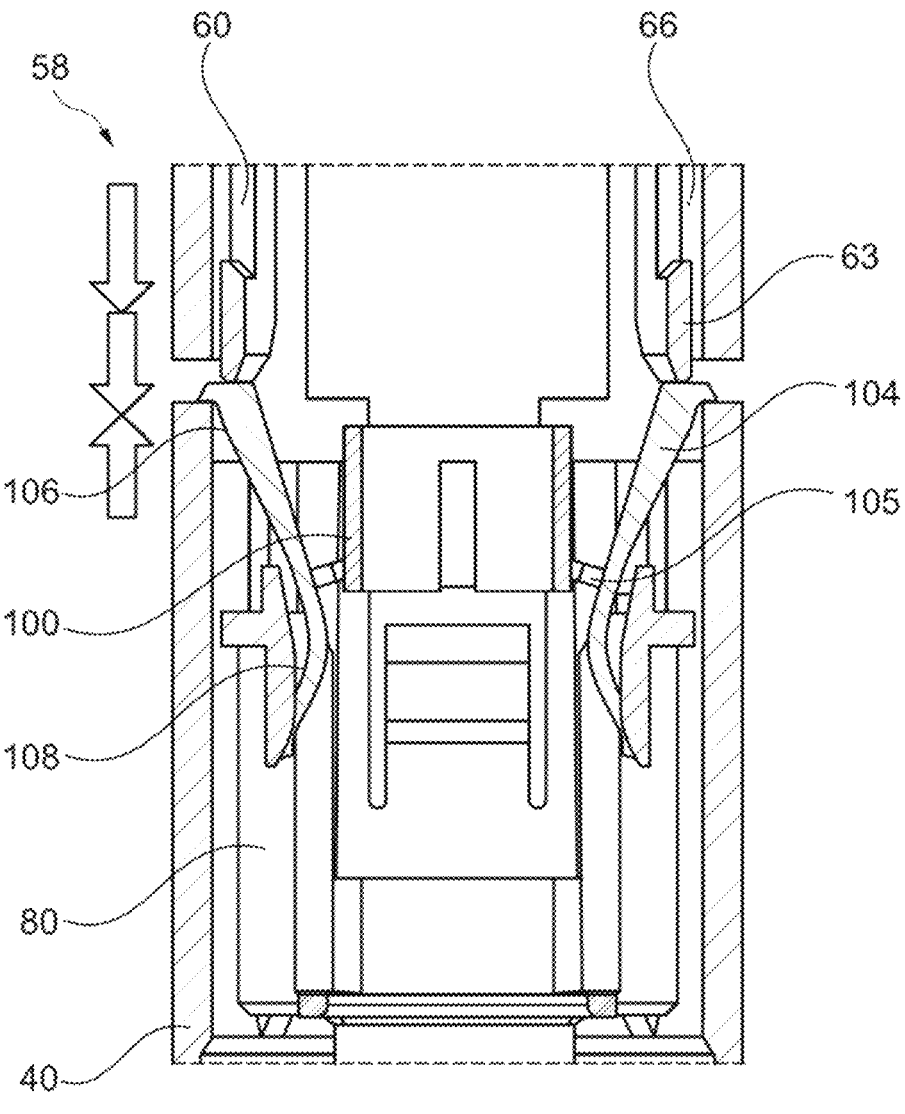
FIG. 9 shows the components in FIG. 5 when an attempt is made to retract the needle guard again after injection.

FIG. 5 shows a similar autoinjector to the autoinjector described in FIG. 1, but with different shaped arms 62 on the needle guard 60. In this example, the arms 62 each comprise a slit 66 (also visible in the example in FIG. 13). FIGS. 5 to 9 show the relative movement of the different parts during use, with FIG. 5 corresponding to FIG. 1, FIG. 6 corresponding to FIG. 2, FIG. 8 corresponding to FIG. 3 and FIG. 9 corresponding to FIG. 4. The difference from FIGS. 1 to 4 can be seen in FIGS. 6 and 7. In FIG. 6, instead of the arm 104 of the needle guard lock being tensioned and remaining adjacent to (and pushing on) the arm 62 of the needle guard, the arm 104 is free to move further from the axis 20 by protruding into (or through in this case) the slit 66 of the needle guard. Once the needle guard moves in the proximal direction again after the injection, the arm 104 is again pushed towards the axis 20 by the distal end 63 of the needle guard arm, as shown in FIG. 7. Once the needle guard is past the arm 104 of the needle guard lock (relative to the axial direction), the arm 104 of the needle guard lock can move away from the axis 20 again as shown in FIG. 8.

Figures 10, 11:
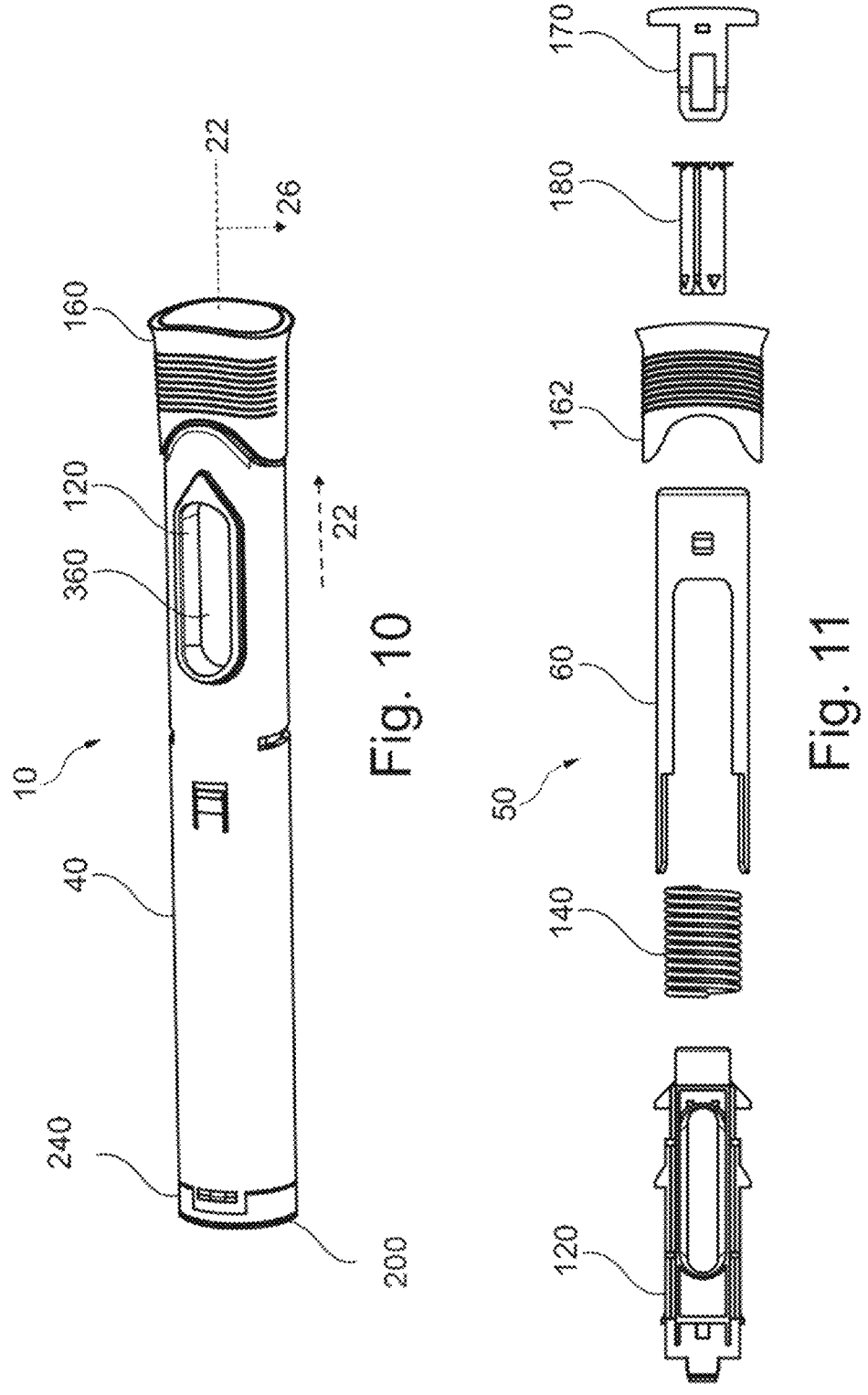
FIG. 10 shows a perspective view of another autoinjector comprising a needle guard lock assembly.
FIG. 11 shows an exploded side view of the front sub-assembly of the autoinjector of FIG. 10.
Figure 12:
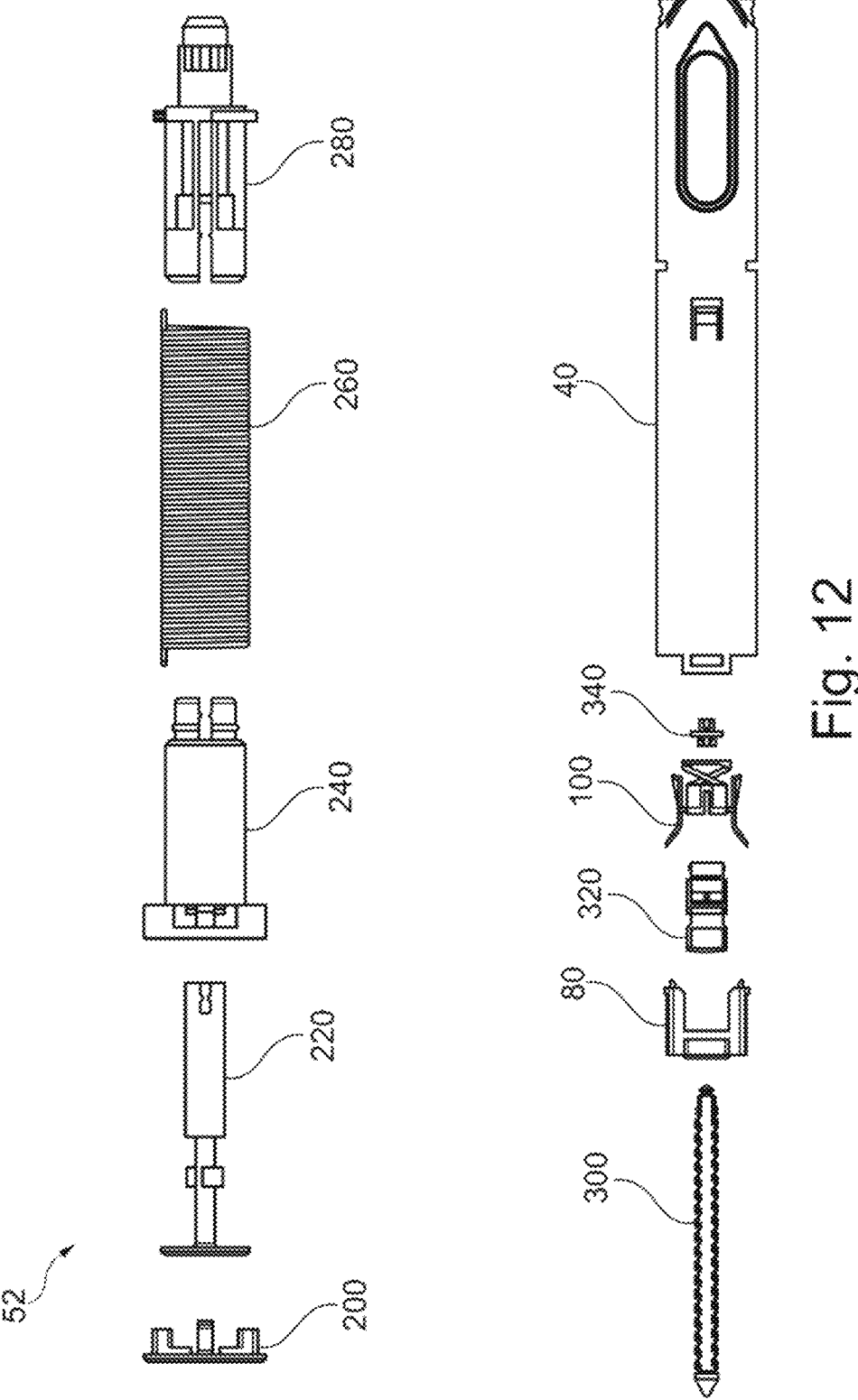
FIG. 12 shows an exploded side view of the rear sub-assembly of the autoinjector of FIG. 10.

FIG. 10 shows another autoinjector 10 including a needle guard lock assembly similar to that shown in FIGS. 5 to 9. In FIG. 10, a housing 40, a cap 160, an optional end cap 200 (rear cap) and a primary package 360 can be seen. A small portion of a powerpack housing 240 can also be seen. FIG. 11 shows the parts of the front sub-assembly (proximal sub-assembly) 50, namely a syringe holder 120, a needle guard spring 140, a needle guard 60 and also the three parts of the cap 160, namely a cap housing 162, a rigid needle shield remover 180 and a cap insert 170. FIG. 12 shows the parts of the rear sub-assembly (distal sub-assembly) 52, namely the end cap 200, an optional powerpack lock 220, a powerpack housing 240, a torsion spring 260, a driver 280, a plunger rod 300, a lock activation sleeve 80, a driver nut 320, a thrust bearing 340 and the housing 40. The parts described above in FIGS. 1 to 9 are not necessarily identical to the corresponding parts described below, but the parts are similar and the functionality is generally the same.

The parts shown in FIGS. 11 and 12 will now be described in more detail. To this end, FIGS. 13 to 28 also show various combinations of parts of the autoinjector 10.

Figures 13, 14:
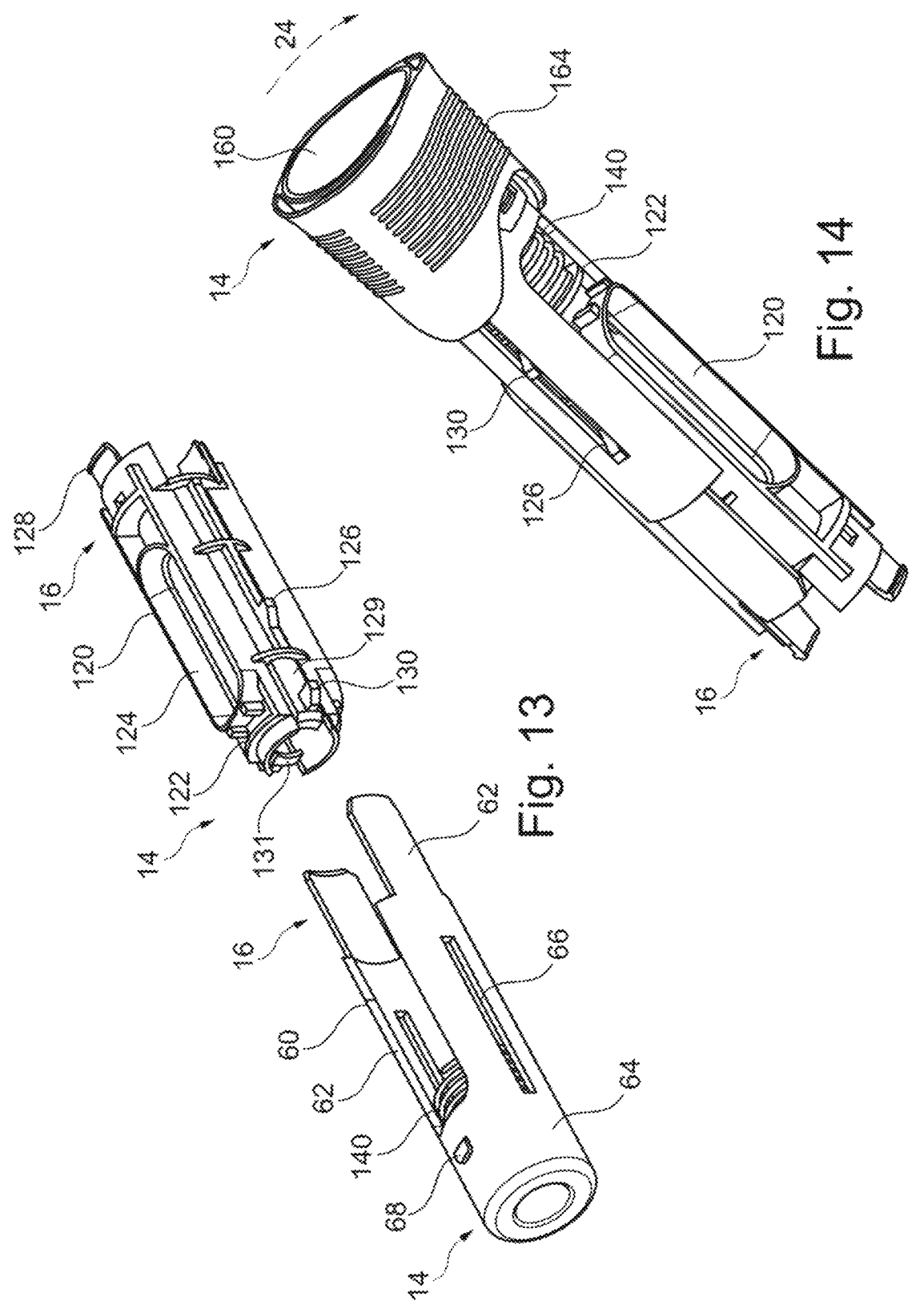
FIG. 13 shows a perspective view of the syringe holder and the needle guard of FIG. 10.
FIG. 14 shows a perspective view of the front sub-assembly of the autoinjector of FIG. 10.

FIG. 13 shows a perspective view of some of the components of the rear sub-assembly, namely the syringe holder 120, the needle guard spring 140 and the needle guard 60. As described elsewhere in the description, each component (and more generally each sub-assembly and each device as well) extends from a proximal end 14 to a distal end 16. FIG. 14 shows the assembled rear sub assembly, with the components in FIG. 13 and the cap 160.

The needle guard can be thought of as a proximal portion and a distal portion, with the proximal portion comprising a guard portion 64 and the distal portion comprising two needle guard arms 62. A needle guard slit 66 extends in the axial direction on each side of the needle guard. The guard portion is tubular, with the axis of the guard portion being parallel to the axis 20 in the assembled autoinjector. The needle guard can also comprise a protrusion 68 to engage a corresponding recess or cut out (not shown) on the cap, which can help keep the cap attached to the rest of the autoinjector, although the cap could alternatively or additionally be attached to the housing, particularly in examples such as the example shown in FIGS. 5 to 9 where removal of the cap allows the needle guard to move in the proximal direction.

The needle guard spring 140 fits inside the needle guard 60, and the proximal end of the needle guard spring engages an engagement feature such as a protrusion or a distally facing ledge (not visible in FIG. 13) of the needle guard. The distal end of the needle guard spring engages a proximally facing ledge 122 on the syringe holder (see FIG. 14).

The syringe holder 120 has a tubular shape, and comprises various features, including the ledge 122, a window 124 and a protrusion 126. The window 124 of the syringe holder is arranged to align with the window 46 when the autoinjector 10 is assembled. The syringe holder comprises a protrusion 126 on each side to engage with the corresponding slits 66 on the needle guard arms 62, thereby keeping the needle guard slidably attached to the syringe holder. The distal side of the protrusions 126 is a distally facing ledge to engage the distal end of the slits 66 as shown in FIG. 14. The proximal side of the protrusions 126 is sloped (angled relative to both the axis 20 and the radial direction 26) to allow the portion of the needle guard arms 62 distal from the slit 66 to slide past the protrusions 126 during assembly. To this end, the needle guard arms 62 are typically flexible in the radial direction 26 to aid assembly, though alternative structures could avoid the need for this flexibility (for example a flexible syringe holder instead).

In FIG. 14, the cap 160 is shown attached to the needle guard 60. The cap is made up of the cap housing 162, the cap insert 170 and the rigid needle shield remover 180, as shown in FIG. 11. An optional grip 164 can be seen on the cap 160.

The composition of the example rear sub-assembly shown in FIG. 12 will now be described in more detail. The rear sub-assembly comprises two separate sub-assemblies, namely a powerpack sub-assembly 54 and an activation sub-assembly 56 (activation mechanism sub-assembly). The powerpack sub-assembly comprises a powerpack housing, a torsion spring, a driver, and optionally a powerpack lock. The mechanism sub-assembly comprises a lock activation sleeve, a needle guard lock, a plunger rod, a driver nut, and optionally a thrust bearing.

Figures 15, 16, 17:
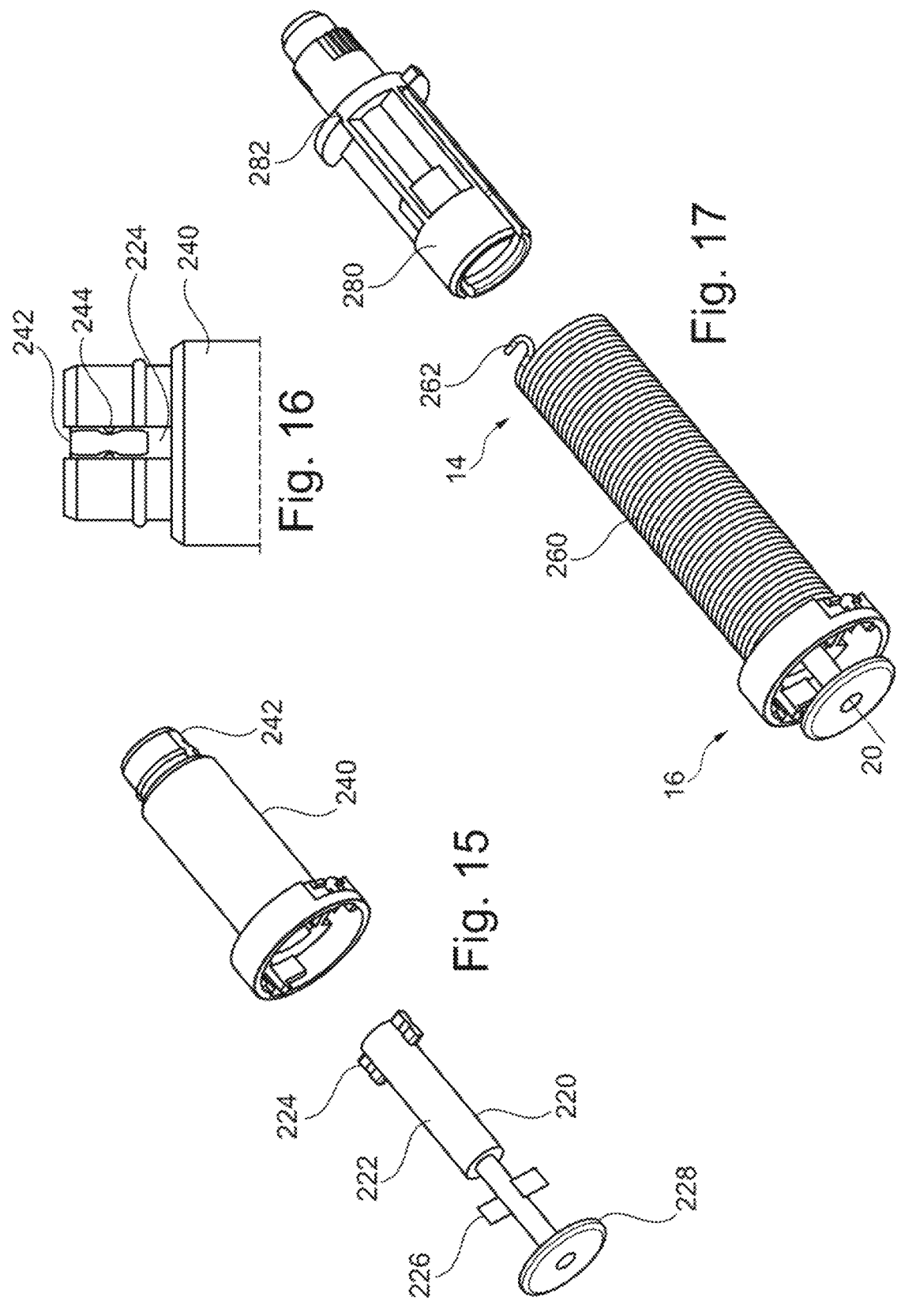
FIG. 15 shows a perspective view of the powerpack lock and the powerpack housing of the powerpack sub-assembly of the autoinjector of FIG. 10.
FIG. 16 shows a close-up side view of part of the powerpack lock and the powerpack housing after initial attachment to one another (first position of the powerpack lock) of the autoinjector of FIG. 10.
FIG. 17 shows a perspective view of the powerpack lock and the powerpack housing of the autoinjector of FIG. 10, along with the torsion spring and the driver before the driver is attached.

FIG. 15 shows the optional powerpack lock 220 and the powerpack housing 240. FIG. 16 shows a view of how the powerpack lock 220 and powerpack housing 240 are initially attached to one another. FIG. 17 shows the powerpack lock 220 and the powerpack housing 240, along with the torsion spring 260 and the driver 280; the driver 280 is shown before being attached.

The powerpack lock 220 comprises a body 222, in this case a tubular body, and two protrusions 224 that extend away from (the proximal end) of the body 222 relative to the axis 20. The protrusions are configured to fit into corresponding slits 242 of the powerpack housing 240 (see in particular FIG. 16). To help with attaching the powerpack lock 220 and the powerpack housing 240 together, two protrusions 244 extend in the circumferential direction into each of the slits 242. The protrusions 224 of the powerpack lock 220 have corresponding recesses to engage the protrusions 244, as can be seen most clearly in FIG. 16.

Figures 18, 19, 20:
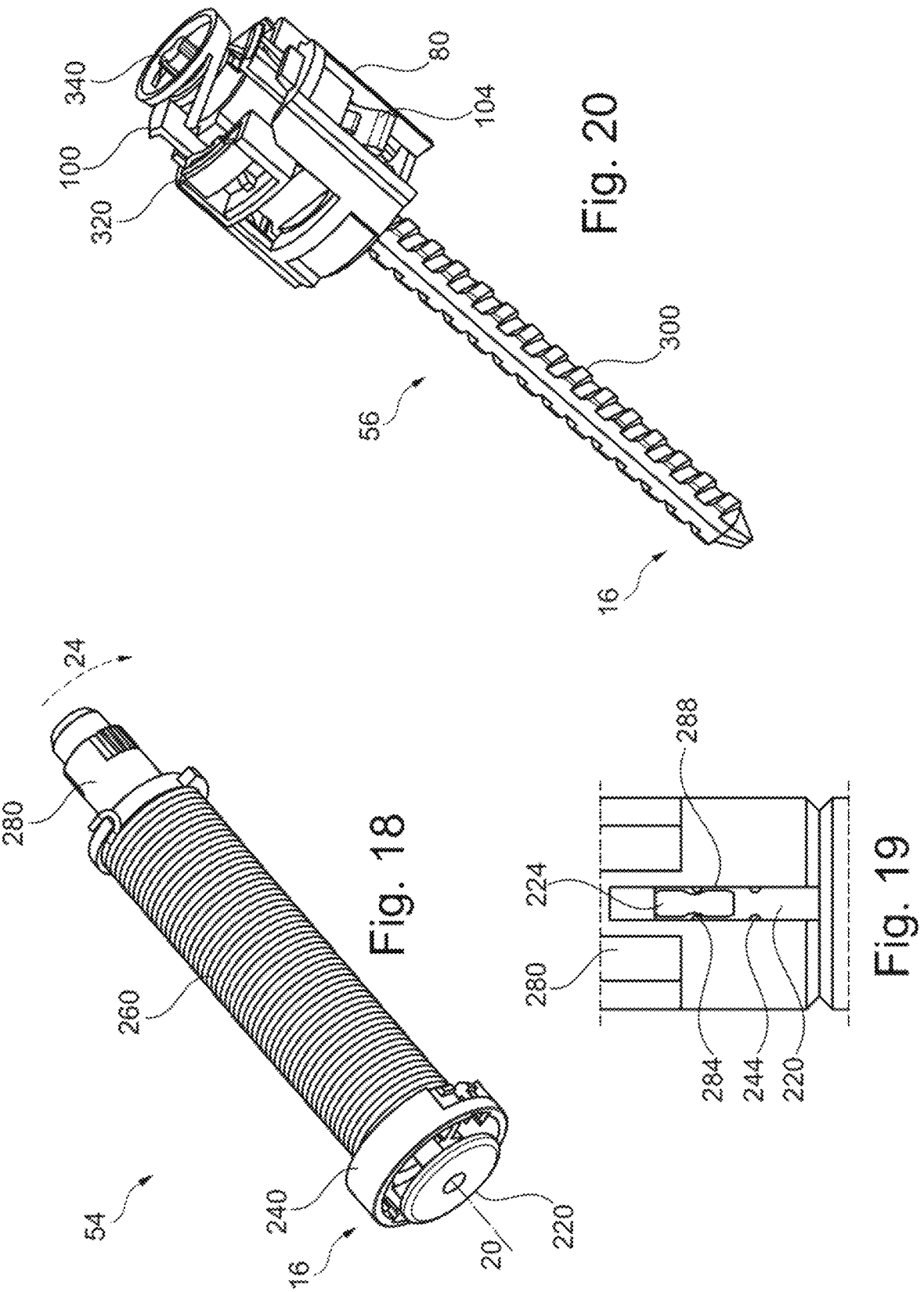
FIG. 18 shows a perspective view of the powerpack sub-assembly of the autoinjector of FIG. 10.
FIG. 19 shows a close-up side view of part of the powerpack lock with the powerpack lock in the second position.
FIG. 20 shows a perspective view of the activation sub-assembly of the autoinjector of FIG. 10.

In FIG. 17, the interaction between the torsion spring 260 and the powerpack housing can be seen. In this particular example, the torsion spring 260 comprises a hook at either end of the spring, namely a proximal hook 262 to attach to the driver 280 and a distal hook (not shown) to attach to the powerpack housing, for example by a cut-out in the powerpack housing (not shown). The proximal hook 262 engages with the driver by engaging with a circumferentially facing ledge 282 on the driver. The position once the driver is in position is shown in FIG. 18. In this position, with the powerpack lock 220 in the first position, as described in more detail below, the driver can be rotated in the circumferential direction to tension the spring.

The powerpack lock 220 is designed to take three different positions during assembly of the autoinjector. The first position of the powerpack lock can be seen in FIGS. 16 and 17. In this position, the powerpack lock is rotationally restricted relative to the powerpack housing.

To reach the second position, the powerpack lock is moved in the proximal direction relative to the powerpack housing from the first position. The powerpack lock is shown in the second position in FIG. 19. In the second position, the powerpack lock is rotationally restricted relative to both the powerpack housing and the driver.

To reach the third position, the powerpack lock is moved in the proximal direction relative to the powerpack housing from the second position. In the third position, the powerpack lock is typically still rotationally restricted relative to the driver (for example, this allows the powerpack lock to provide an optional clicking sound during injection as will be described below), but is no longer rotationally restricted relative to the powerpack housing. The powerpack lock is typically only moved to the third position after the driver has been rotationally locked to the housing, for example by a driver nut (this rotational lock between the driver and driver nut is described in more detail in a later example, particularly with reference to FIGS. 46 to 49, and works the same way in the present example). The powerpack lock therefore provides a lock to keep the spring tensioned during a portion of the assembly process. In some examples, the powerpack lock can additionally or alternatively provide an optional clicking sound during injection, for example with the protrusions 226 engaging corresponding protrusions or ribs (not directly shown in this example, but see FIG. 52 for an illustrated example) on the inside of the powerpack housing. In a completed device, the powerpack lock will be in the third position. Instead of being a different position, the third position could be the same as the first position. Alternatively, instead of being moved to the third position, the powerpack lock could be removed from the device once the driver is locked from rotating by another part of the device (e.g. the driver nut as shown in FIGS. 46 to 49), and therefore the powerpack lock may not be present in the final device. The plunger rod may fit inside the body 222 of the powerpack lock, particularly in examples where the powerpack lock remains in the fully assembled device.

In another alternative, a tool is used that provides the functionality of the powerpack lock during assembly, rather than having a powerpack lock component. The various features of the powerpack lock, such as the body 222, the protrusions 224, 226 and the handle 228 can vary in shape—for example, in an embodiment where the third position and first position are the same and the powerpack lock remains in the device after assembly, the length of the body would need shortening and the handle would need to be arranged differently compared to the powerpack lock 220 shown in FIG. 15.

FIG. 18 shows the same parts as FIG. 17, but with the driver 280 now attached. Once the driver is attached, the driver can be rotated in the circumferential direction 24 to tension the spring. Once the spring is tensioned, the powerpack lock 220 is moved in the proximal direction from the first position (as shown in FIGS. 16 and 17) to the second position (as shown in FIGS. 18 and 19) to hold the driver, and therefore also the tensioned spring, in place relative to the powerpack housing 240. This engagement to hold the spring tensioned is achieved by two different interactions. Firstly, as shown in FIG. 19, once the powerpack lock 220 is moved in the proximal direction, the protrusion 224 of the powerpack lock is moved from not engaging the driver to engaging with a slot 288 on the inside of the driver. In a similar manner to the use of protrusions 244 to help attach the powerpack lock 220 and the powerpack housing 240 together, the driver 280 comprises two protrusions 284 that engage the same recesses in the protrusion 224 of the powerpack lock.

The second interaction that enables the spring to stay tensioned is provided by the protrusion 224 of the powerpack lock 220 as shown in FIG. 16, which partly still remains in the slit 242 of the powerpack housing in the second position, thereby rotationally locking both the powerpack housing 240 and the driver 280 relative to the powerpack lock 220, thereby stopping the spring 260 from releasing the tension.

An optional safety pin or safety guard could also be provided that locks the powerpack lock in the second position, for example a clip holding a handle 228 of the powerpack lock 220 in place relative to the distal end of the powerpack housing 240.

Figures 21, 22, 23:
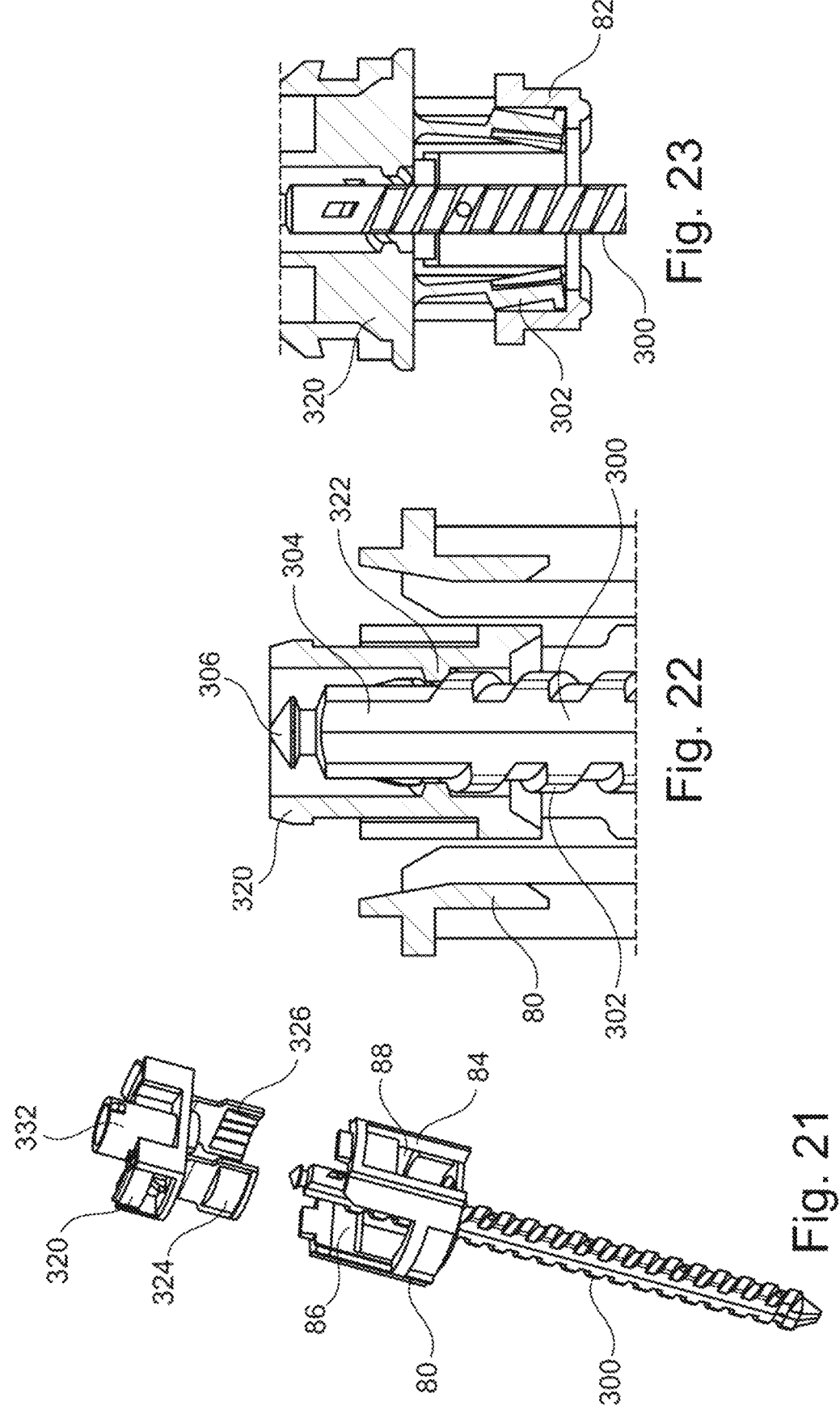
FIG. 21 shows a perspective view of the plunger rod, the lock activation sleeve and the driver nut of the activation sub-assembly of FIG. 20.
FIG. 22 shows a side cross-sectional view of a close-up of part of the lock activation sleeve and the driver nut, along with a side view of the plunger rod.
FIG. 23 shows a side cross-sectional view of a close-up of part of the lock activation sleeve and the driver nut, along with a side view of the plunger rod of FIG. 20, at an angle of 90 degrees to the view in FIG. 22.

The activation sub-assembly of the rear sub-assembly will now be described in more detail. FIG. 20 shows the assembled activation sub-assembly, comprising the plunger rod 300, the lock activation sleeve 80, the needle guard lock 100, the driver nut 320, and the thrust bearing 340. FIG. 21 shows part of the activation sub-assembly, namely the plunger rod 300, the lock activation sleeve 80 and the driver nut 320 before they have been fully assembled. FIGS. 22 and 23 show how the plunger rod 300, the lock activation sleeve 80 and the driver nut 320 are attached to one another by means of cross-section close ups. The plunger rod 300 comprises a screw thread 302 that engages with the corresponding screw thread 322 on the driver nut 320. As can be seen in FIGS. 21 to 23 in particular, the plunger rod 300 has a screw thread 302 only around part of its circumference, with two flattened sides as well; the flattened sides allow the plunger rod to engage the driver 280 (see also FIG. 37).

The driver nut 320 comprises a screw thread 322 as mentioned above, and also comprises two arms 324. Typically, the arms 324 predominantly extend in the axial direction. The arms 324 comprise teeth 326 on a surface facing towards the axis 20 which can engage a driver 280 as will be described in more detail later (see for example FIG. 49). The arms 324 also comprise a surface facing away from the axis 20 which engages the lock activation sleeve 80 as shown in FIG. 23. As can be seen in FIG. 23, once the driver nut 320 and lock activation sleeve 80 have been assembled together, the arms 324 of the driver nut 320 are biased inwards (this bias is released when the lock activation sleeve 80 is pushed in the distal direction by the needle guard 60). In this example, the driver nut 320 comprises a base 332 (for example a tubular base) to which the screw thread 322 and the arms 324 are attached.

The lock activation sleeve 80 comprises a tubular section 82 and two arms 84, with each arm comprising a pad 86. A cut-out 88 is provided in each arm 84 to accommodate the distal part 108 of the arm of the needle guard lock 100 (see FIG. 27 for example).

Figures 24, 25, 26:
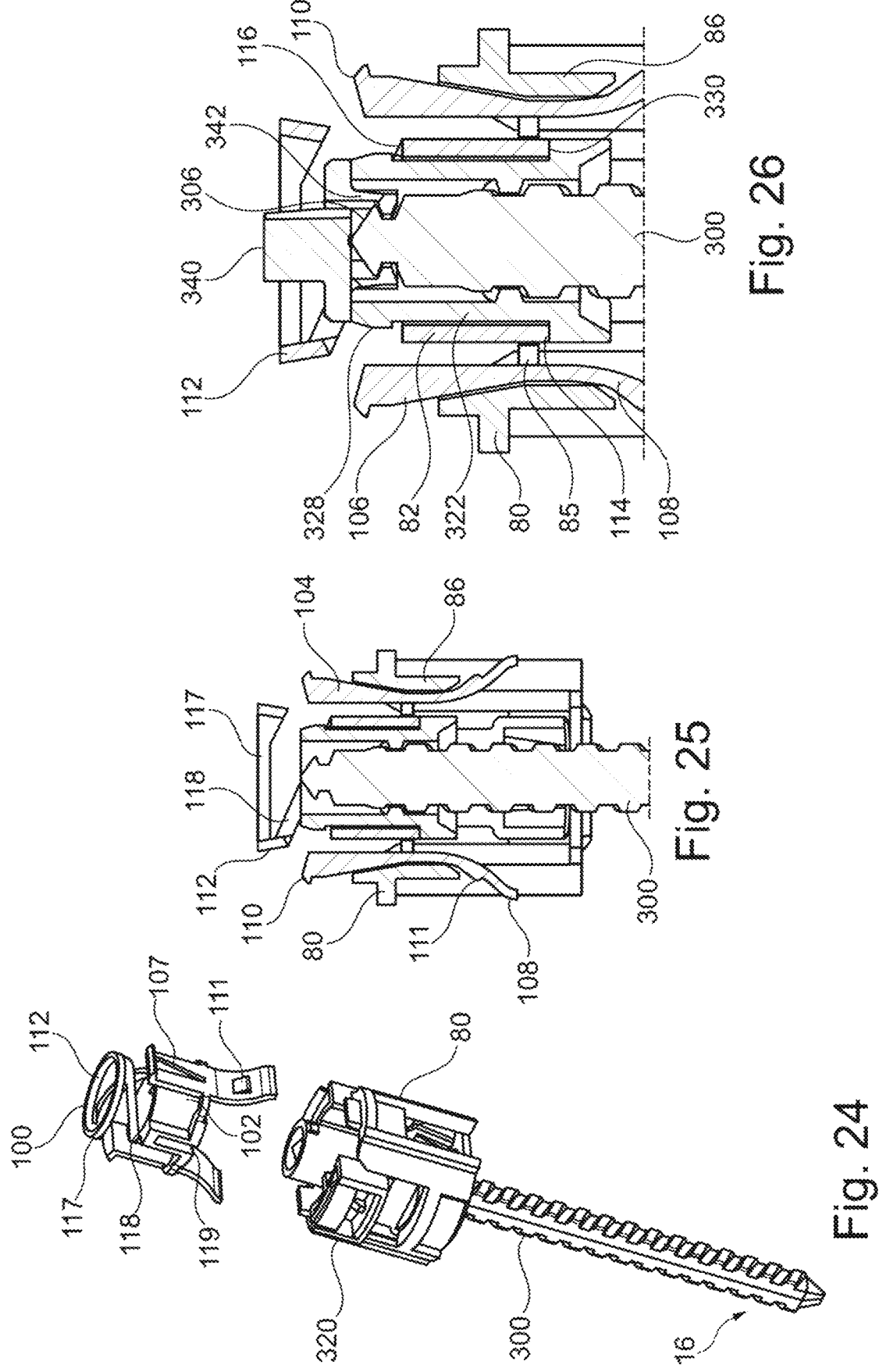
FIG. 24 shows a perspective view of the plunger rod, the lock activation sleeve, the needle guard lock and the driver nut of the activation sub-assembly of FIG. 20.
FIG. 25 shows a side cross-sectional view of the parts shown in FIG. 24 when assembled.
FIG. 26 shows a side cross-sectional view of part of the activation sub-assembly of FIG. 20.

FIG. 24 shows the plunger rod 300, the lock activation sleeve 80, the needle guard lock 100 and the driver nut 320, with the needle guard lock 100 not yet assembled. FIG. 25 shows a close-up side view of the parts in FIG. 24 when assembled together. Similarly, FIG. 26 shows another close-up side view of the parts in FIG. 24, this time also with the thrust bearing 340. Various features of and interactions between these parts will now be described, in particular with reference to FIG. 26. The driver nut 320 comprises a base 332, and the tubular section 102 of the needle guard lock 100 extends around the base 332. An optional feature to hold the needle guard lock 100 in place relative to the driver nut 320 (although some axial movement may be allowed, as is the case in this example) is a distally facing ledge 114 of the needle guard lock 100 provided adjacent to a proximally facing ledge 330 of the driver nut 320, along with a proximally facing ledge 116 of the needle guard lock 100 adjacent to a snap-fit protrusion 329 of the driver nut 320. The tubular section 102 of the needle guard lock 100 can pass the snap-fit protrusion for assembly, but cannot easily get back past it, holding it in place relative to the driver nut 320.

The thrust bearing 340 comprises snap fit arms 342 that engage a corresponding snap fit ledge 306 of the plunger rod 300. The thrust bearing 340 can rotate around the axis 20 relative to the plunger rod 300, but is held in the axial direction relative to the plunger rod 300 (in practice in this particular example, the plunger rod will rotate relative to the housing during use and the thrust bearing will not rotate relative to the housing).

Figures 27, 28:
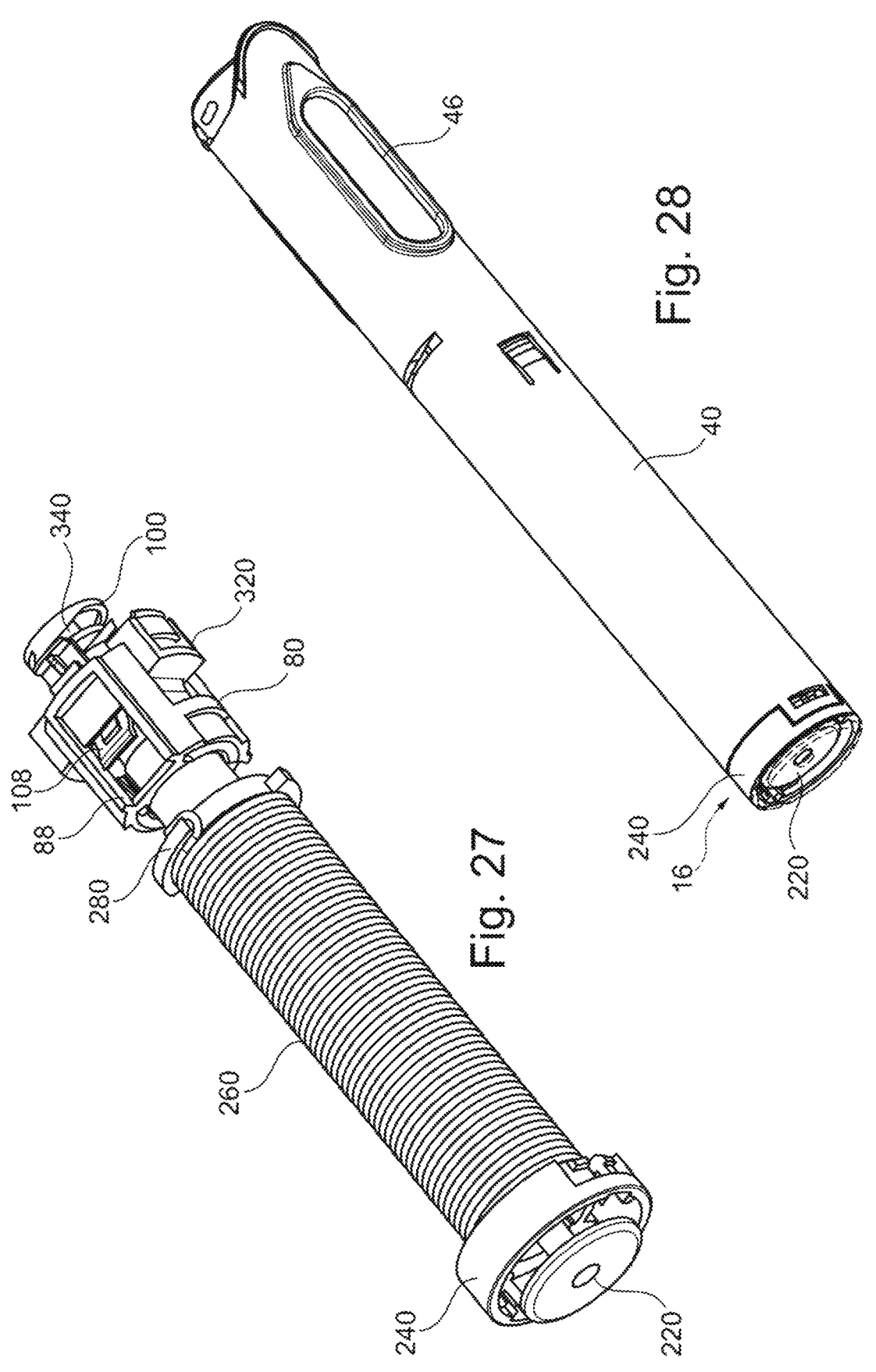
FIG. 27 shows a perspective view of the powerpack sub-assembly and the activation sub-assembly of the autoinjector of FIG. 10 attached together.
FIG. 28 shows a perspective view of the powerpack sub-assembly and the activation sub-assembly of the autoinjector of FIG. 10 attached together and inside the housing 40.

FIG. 27 shows the powerpack sub-assembly and the activation sub-assembly attached together. These two sub-assemblies then fit inside a housing 40 as shown in FIG. 28—in this case a single outer housing, though the housing could instead be made up of multiple parts. This combination of a powerpack sub-assembly, an activation sub-assembly and a housing makes up a complete rear sub-assembly. An end cap (not shown) would typically also be included at the distal end of the housing as part of the rear sub-assembly.

Figure 29:
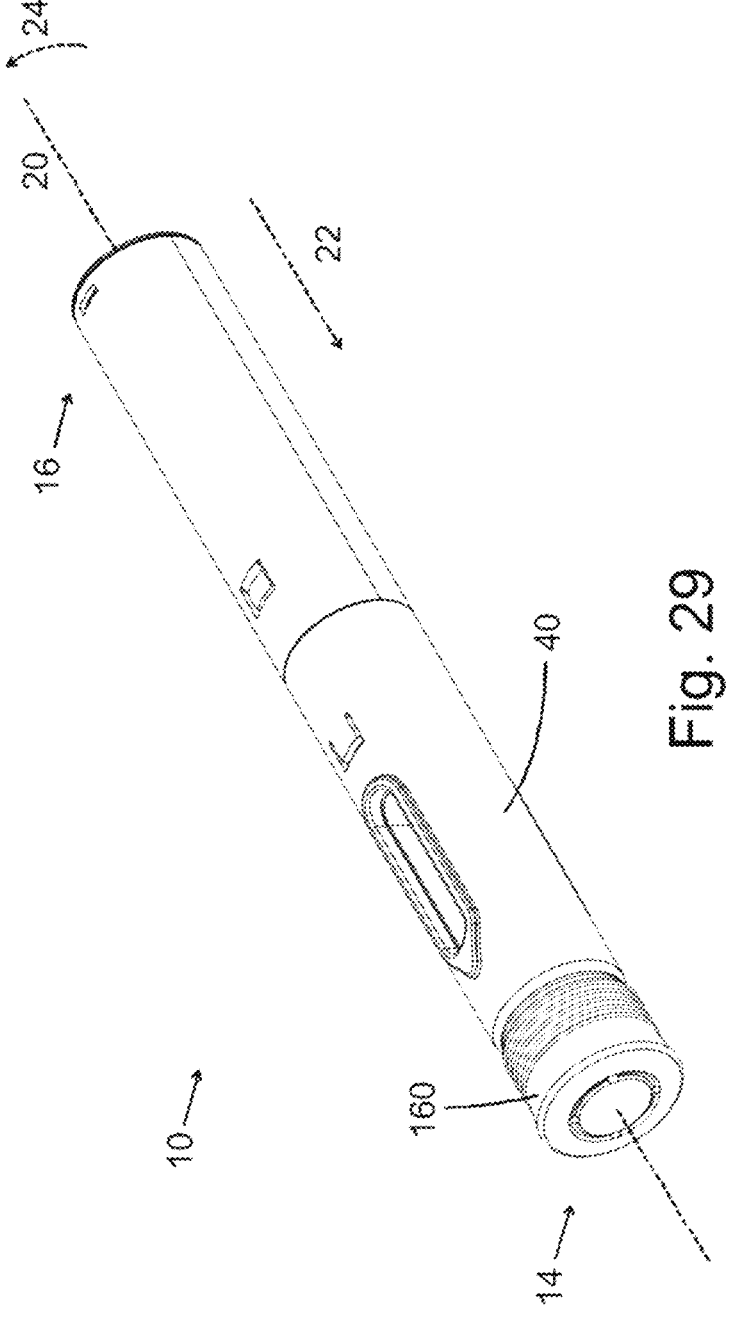
FIG. 29 shows a perspective view of another example autoinjector.

Another example autoinjector is shown in FIG. 29, and will be described in detail with reference to the subsequent figures. Both the autoinjector and the needle guard lock assembly inside the autoinjector are somewhat different from those described in the example above. Nevertheless, the autoinjector in the example described below could be used with the needle guard lock assembly from the example of FIG. 1, 5 or 10, and the autoinjector in the examples of FIG. 1, 5 or 10 could be used with the needle guard lock assembly described below.

Figure 30:
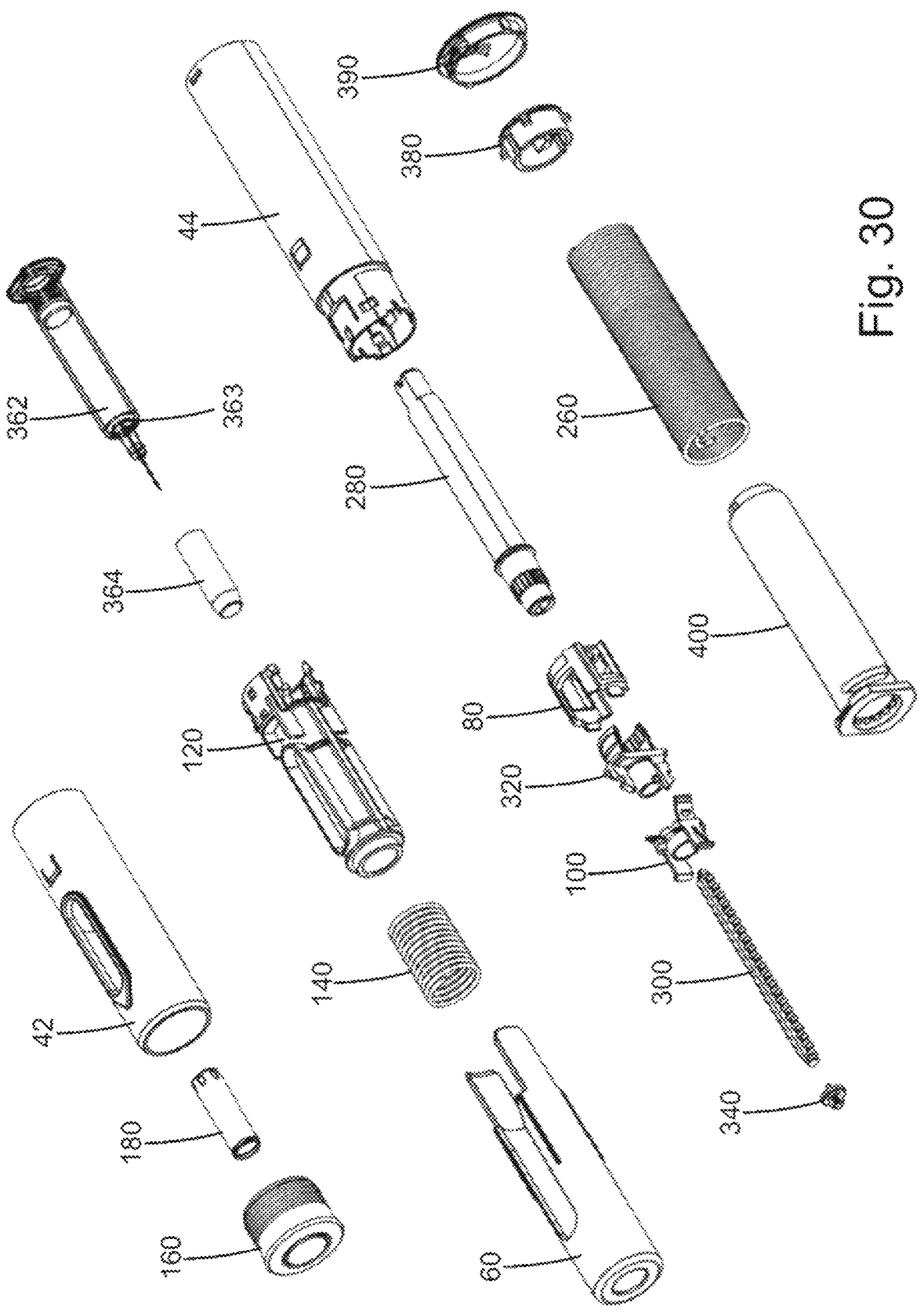
FIG. 30 shows a perspective exploded view of the components of the autoinjector of FIG. 29.
Figure 31:
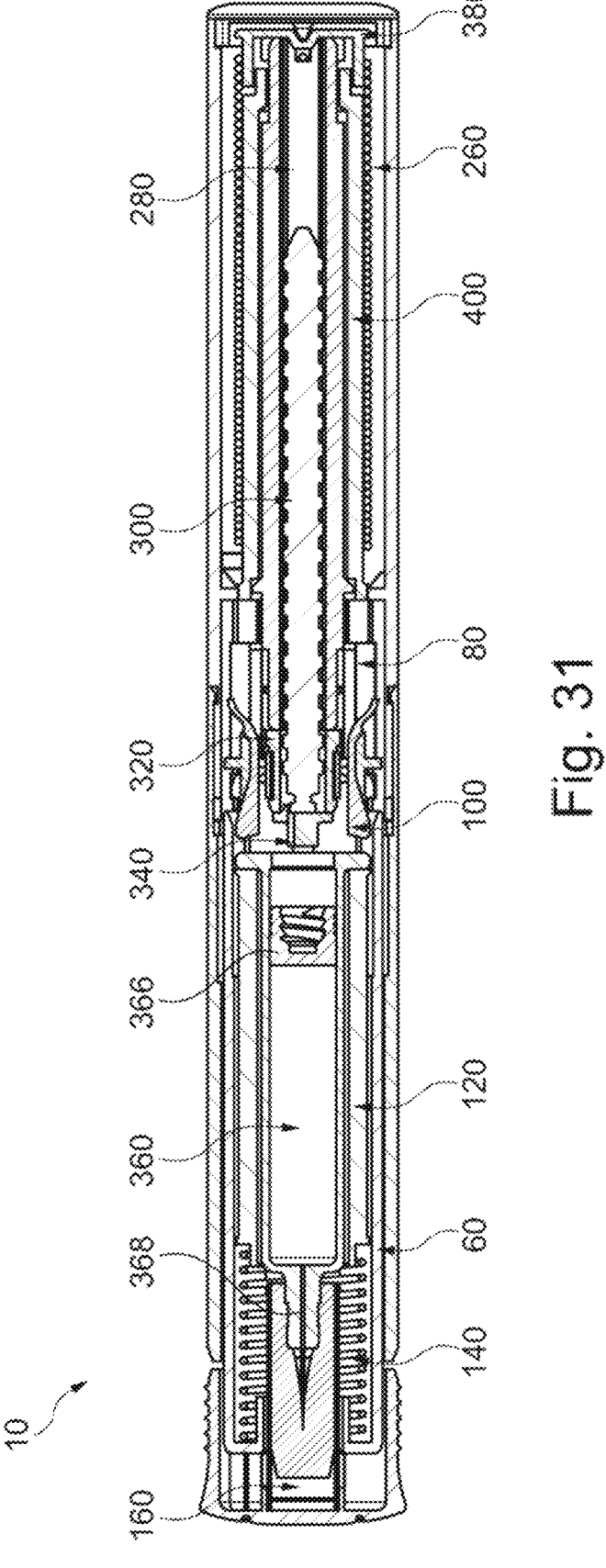
FIG. 31 shows a cross-sectional view of the autoinjector of FIG. 29 before use.

As shown in FIG. 29, the autoinjector extends from a proximal end 14 to a distal end 16, and comprises a housing 40 and a cap 160. The autoinjector extends along an axis 20 in an axial direction 22 and around the axis in a circumferential direction 24. FIGS. 30 and 31 show the autoinjector components, namely a cap 160, a rigid needle shield remover 180, a proximal housing 42, a needle guard 60, a needle guard spring 140, a syringe holder 120, a primary package comprising a syringe 362 and a rigid needle shield 364, a thrust bearing 340, a plunger rod 300, a needle guard lock 100, a driver nut 320, a lock activation sleeve 80, a driver 280, a distal housing 44 (rear housing), a spring holder 400, a torsion spring 260, an optional spinner 380 and an end cap (in this case a spinner cap 390). Broadly speaking, the functionality of these parts is the same as the functionality for the equivalent parts described above unless described otherwise below, and the parts are interchangeable between the example autoinjectors. The focus in the description of the example shown in FIG. 10 onwards was the shape of the parts and how they fit together; the focus in describing the FIG. 29 example is on how the autoinjector works.

Apart from some differences in component shape (for example the lack of a concertina section 112 on the needle guard lock 100 in the example of FIG. 29), the largest differences between the FIG. 10 and FIG. 29 example occur in the rear sub-assembly, for example with the provision of a spinner 380, a spinner cap 390 and a spring holder 400. The spinner 380 is attached to the driver and rotates when the driver rotates. The spinner cap 390 is attached to the distal housing 44 and can be considered as an end cap. The spring holder 400 is an example of a powerpack housing and holds the torsion spring 260 and is engaged with the driver 280.

A description of how the device fits together and how it works will now be provided, primarily with reference to the example in FIGS. 29 and 30. The same method of operation is also applicable to the other autoinjectors described herein unless otherwise stated.

Figures 32, 33:
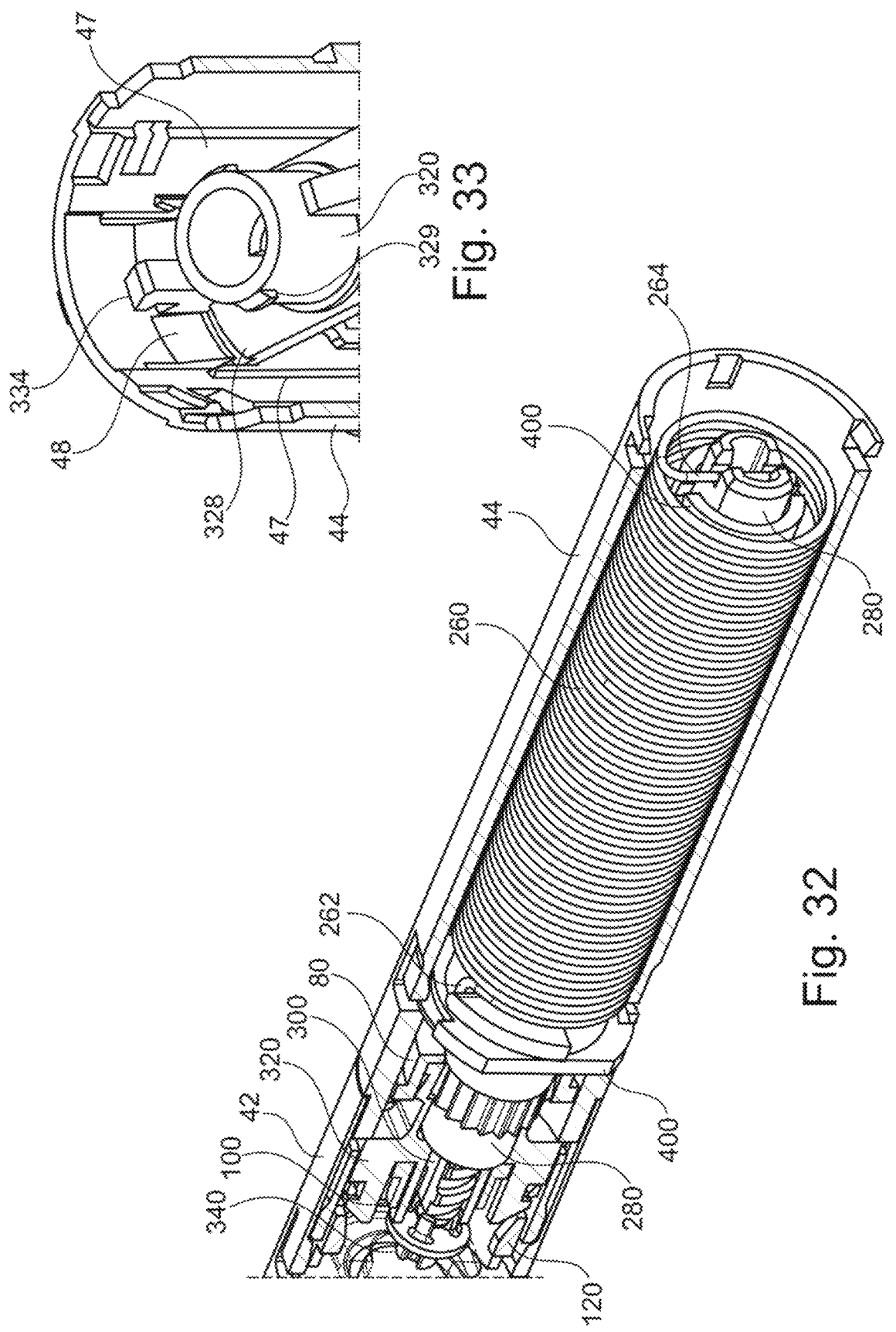
FIG. 32 shows a perspective and partially cross-sectional view of part of the autoinjector of FIG. 29 before use.
FIG. 33 shows a perspective and partially cross-sectional view of the housing and the driver nut of the autoinjector of FIG. 29.

FIG. 32 shows details of how a number of the parts of the autoinjector fit together. Torque is applied to the distal end of the driver 280 by the loaded torsion spring 260 (specifically the distal end protrusion 264 of the torsion spring 260) via the spring holder 400 and the distal housing 44. Specifically, the torsion spring is fixed to the spring holder 400 at the proximal end (specifically by the proximal end protrusion of the torsion spring 260, which is a hook in this example). The spring holder 400 is fixed to the distal housing 44, and is therefore not able to rotate relative to the housing (see FIGS. 36 and 37 in particular). The distal end protrusion 264 of the torsion spring 260 is connected to distal end of the driver 280, transmitting the torque of the torsion spring 260 to the driver 280, and therefore causing the driver to rotate once the device is activated and the driver is released to rotate (see FIGS. 34 and 35 in particular for the release of the driver).

FIG. 33 shows further detail of how the driver nut 320 is attached to the distal housing 44. Typically, the driver nut is largely or completely restricted from moving relative to the housing. In this particular example, inwardly and longitudinally extending ribs 47 on the distal housing 44 engage with a corresponding protrusion 328 on the driver nut 320 to stop the driver nut 320 from freely rotating relative to the distal housing 44; this indirectly stops the torsion spring 260 from rotating prior to device activation. The driver nut is also restricted from moving in the axial direction relative to the distal housing 44 by a snap fit 48. The driver nut is optionally connected to the syringe holder 120 as well (see FIG. 32), for example by a hook 128 (see FIGS. 13 and 34 in particular) on the syringe and a corresponding hook 334 on the driver nut (see FIG. 34—this hook is not present in the example in FIGS. 10 to 28, though it could be included).

Figure 34:
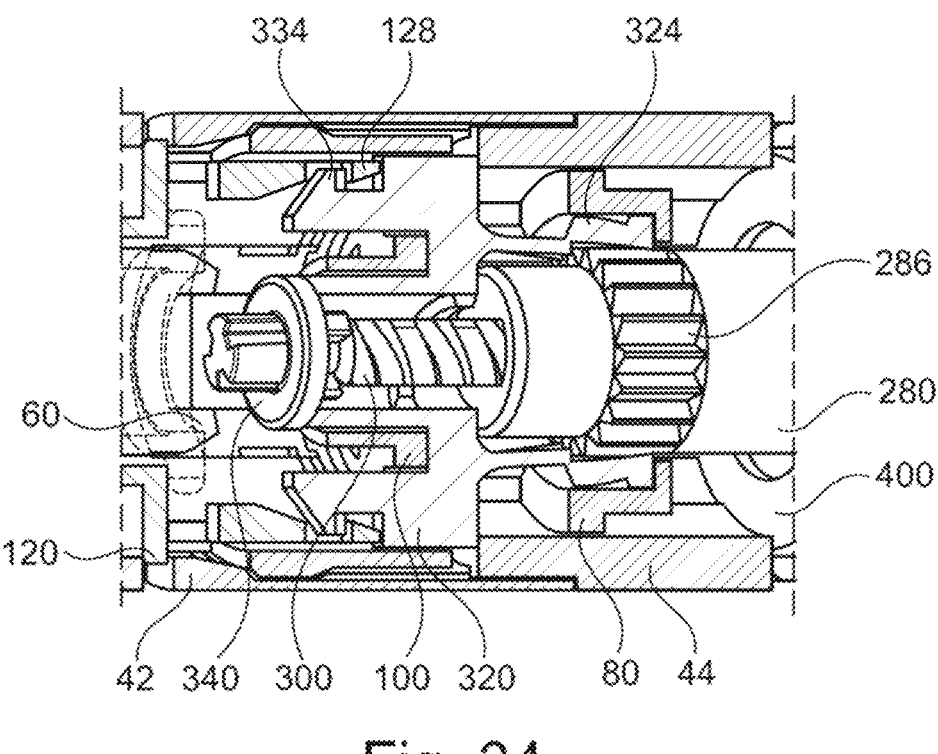
FIG. 34 shows a perspective and partially cross-sectional view of part of the autoinjector of FIG. 29 before use.

FIG. 34 focusses in on the connectivity between the parts around the driver nut 320. Prior to device use the plunger rod 300, which is threaded, is rotationally held in its start position by the driver 280 (see for example FIG. 37) and axially held by the screw thread 322 in the driver nut 320, which engages the screw thread 302 of the plunger rod 300. Prior to device use, the arms 324 of the driver nut 320 are biased inwards (towards the axis 20) by the lock activation sleeve 80. The inwardly facing driver nut teeth 326 thereby engage with the corresponding outwardly facing driver teeth 286.

Figure 35:
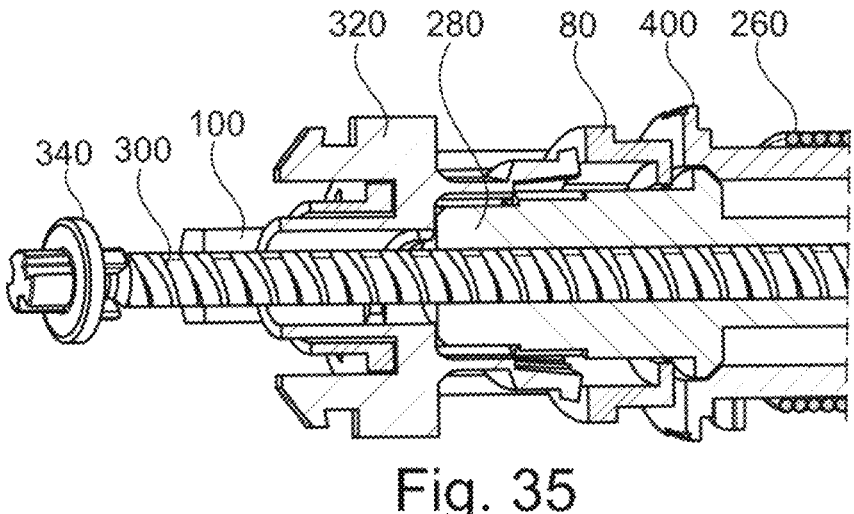
FIG. 35 shows a side and partially cross-sectional view of some of the components of the autoinjector of FIG. 29 during injection.

FIG. 35 shows most of the parts of the device as shown in FIG. 34, but this time the device is shown after the needle guard 60 has pushed back the lock activation sleeve 80, thereby releasing the arms 324 of the driver nut 320 and disengaging the lock between the teeth 286 of the driver 280 and the teeth 326 of the driver nut 320. This disengagement allows the torsion spring 260 to directly rotate the driver, and the plunger rod 300 is directly rotated by the driver 280. The rectangular cross-section of the rotating plunger rod interacts with the corresponding internal cross-section of the driver 280 (see FIG. 37 in particular), which transmits the rotation torque from the torsion spring 260 into to a linear force. At the proximal end of the plunger rod 300, a thrust bearing 340 is preferably attached. The thrust bearing is preferably free to rotate independently relative to the rotating plunger rod 300, which allows the thrust bearing to remain stationary relative to the stopper 366 during injection, thereby only transmitting the linear force to the stopper 366. Provision of a thrust bearing can also be advantageous in that the shape of the thrust bearing can help transfer force from the plunger rod to the stopper more gently—for example by engaging a larger surface area of the stopper and/or by engaging the outer rim 367 of the distal end of the stopper (see FIG. 42).

Figure 36:
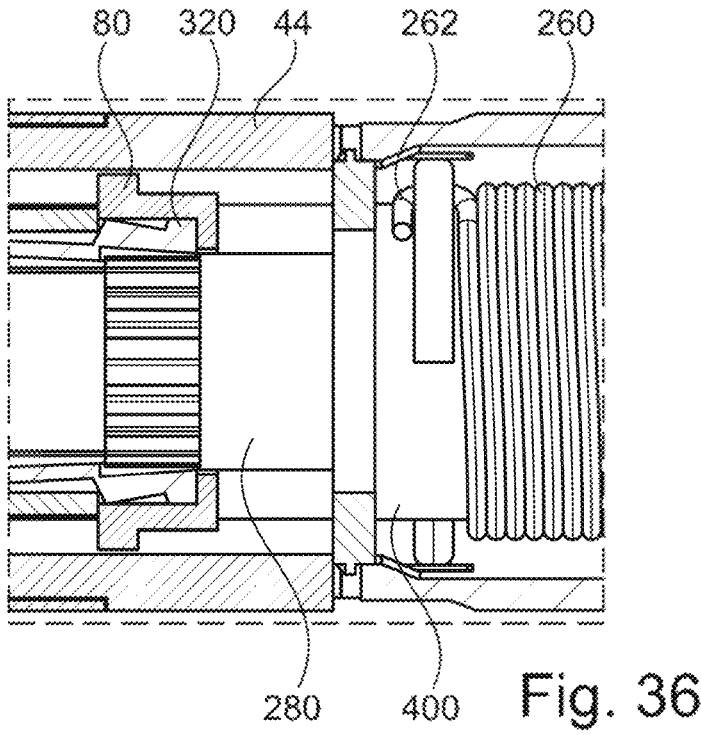
FIG. 36 shows a side and partially cross-sectional view of part of the autoinjector of FIG. 29 before use.
Figure 37:
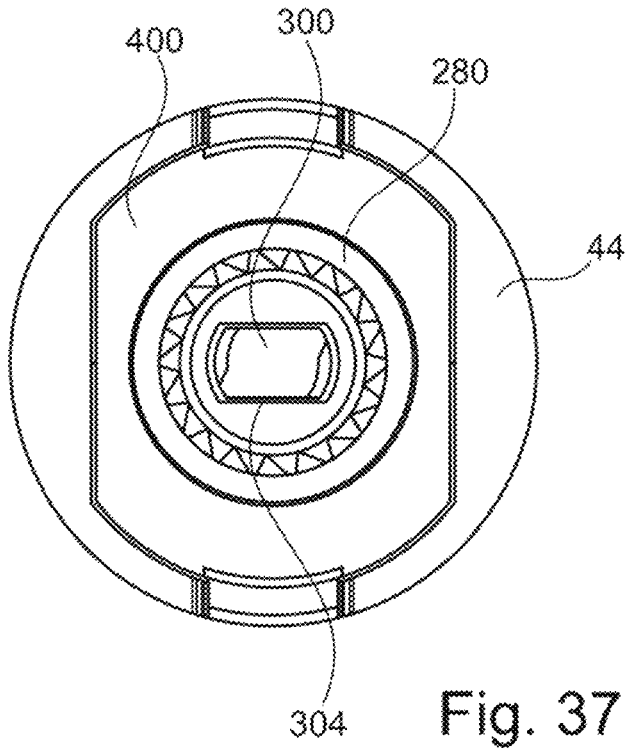
FIG. 37 shows a view looking in the axial direction of some of the components of the autoinjector of FIG. 29.

FIGS. 36 and 37 show how the spring holder 400 is rotationally fixed to the distal housing 44 and how the driver 280 is rotationally fixed to the plunger rod 300. In both cases, this is achieved by corresponding non-circular cross-sections (in other words, a keyed opening in the driver and a correspondingly shaped key in the shape of the plunger rod), which in this example are provided by corresponding straight edges (i.e. deviation from a circular cross-section), although various other shapes could be used instead. In this case, the keyed opening is in the distal housing and a correspondingly shaped flange on the proximal end of the syringe holder engages the keyed opening. Similarly, the keyed opening in the driver receives the plunger rod. The syringe holder is also preferably restricted from longitudinal movement relative to the housing, in this example by engaging with a slit in the distal housing.

Figures 38, 39, 40:
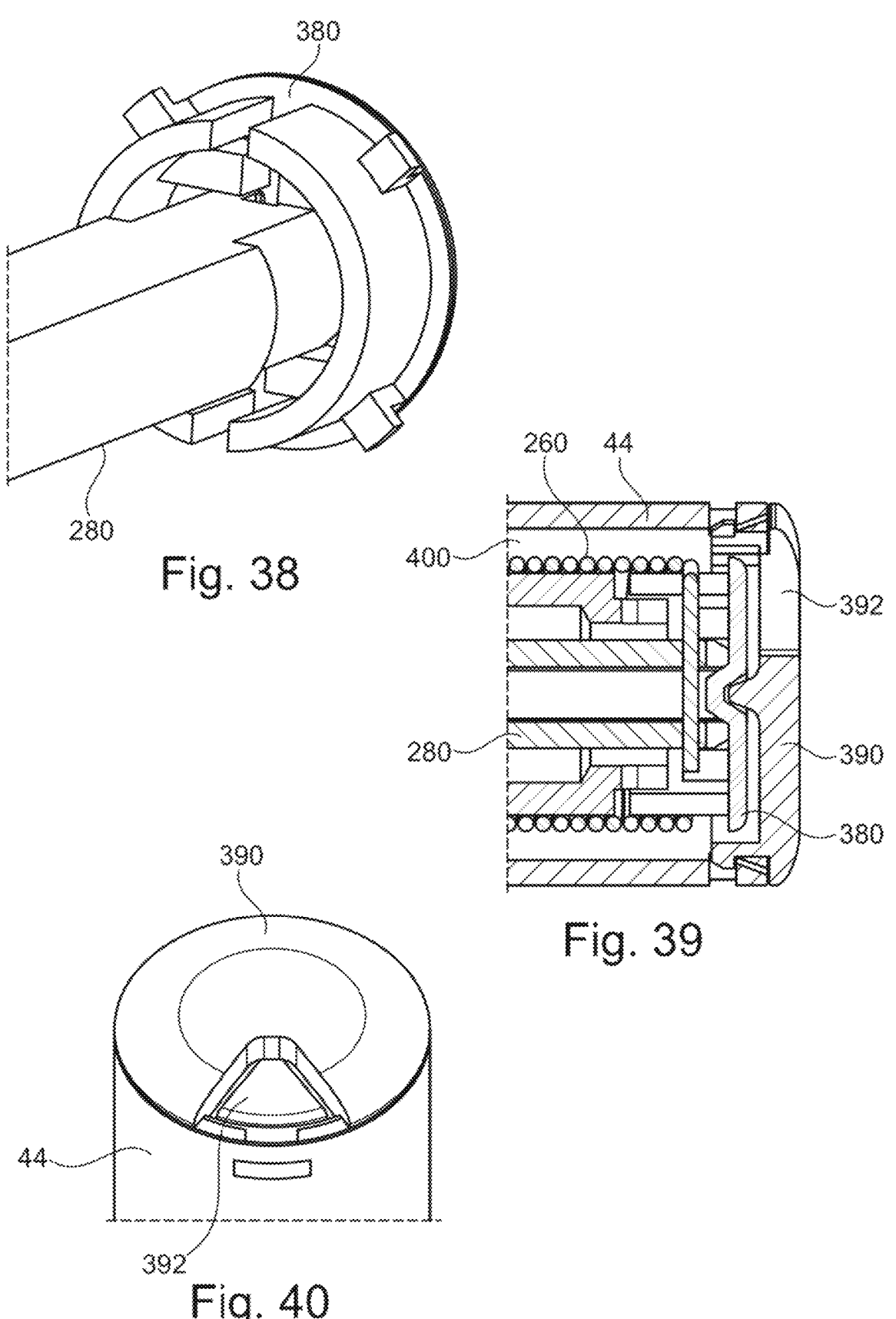
FIG. 38 shows a perspective view of the driver and the spinner of the autoinjector of FIG. 29.
FIG. 39 shows a cross-sectional view of the distal end of the autoinjector of FIG. 29.
FIG. 40 shows a perspective view of the distal end of the autoinjector of FIG. 29.

FIGS. 38 to 40 shows details of the placement of the spinner 380 and the spinner cap 390. The spinner cap 390 comprises a window 392 through which the spinner can be seen; the spinner would typically have a pattern on it so that rotational movement of the spinner can easily be seen by a user. The spinner 380 is rotationally fixed to the driver (or another part that rotates during delivery) so that the spinner rotates when the driver rotates. The spinner 380 (or in the absence of a spinner, the end cap) could support the distal end of the driver 280 to ensure that the driver 280 remains concentric within the housing.

FIGS. 41 to 45 will now be used to describe the working of the needle guard lock assembly within the example of FIG. 29. In general, the needle guard lock assembly of FIG. 30 is the same as that shown in the earlier examples, so the various parts are interchangeable between the examples and the working of the other examples is the same.

Figure 41:
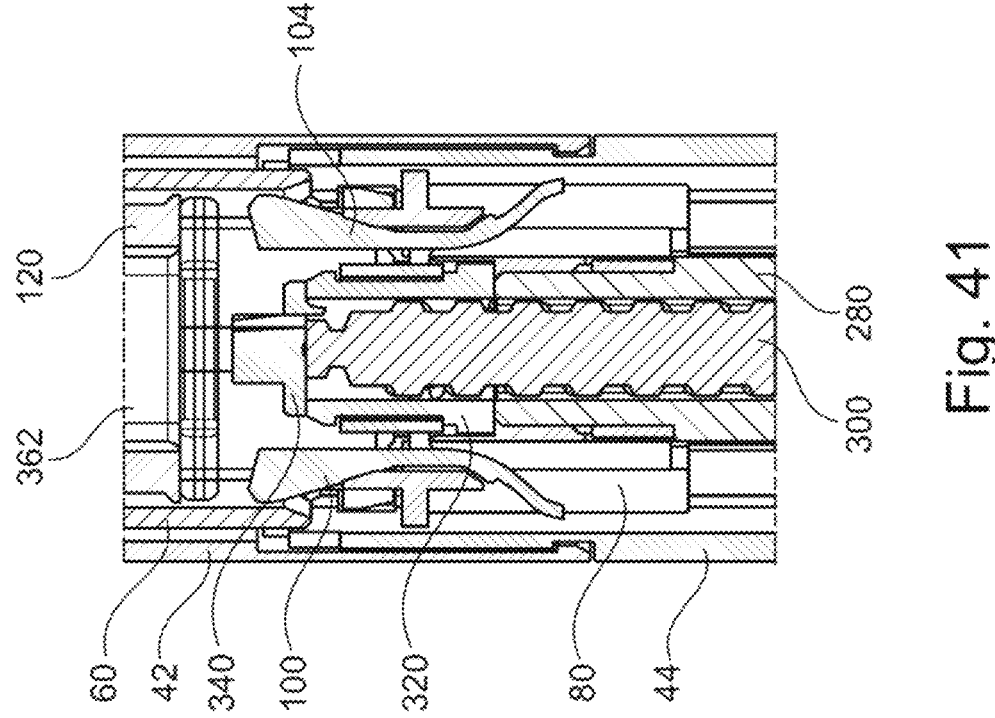
FIG. 41 shows a cross-sectional view of part of the autoinjector of FIG. 29 before use.

FIG. 41 shows an autoinjector prior to use, with all the parts in their starting positions. One notable difference in this design is that the needle guard 60 and the needle guard lock 100 overlap in the axial direction, whereas in the designs shown in FIGS. 1 and 5, for example, the needle guard 60 and the needle guard lock 100 do not overlap. This overlap is optional in all the needle guard lock assembly designs. A benefit of providing the overlap is that it makes it harder for the lock activation sleeve 80 to be pushed in the distal direction prior to use, for example if the device is dropped. This is because the proximal part 106 of the needle guard lock arm is kept from moving away from the axis 20, making it harder for the lock activation sleeve 80 to be pushed past the distal part 108 of the needle guard lock arm.

Figure 42:
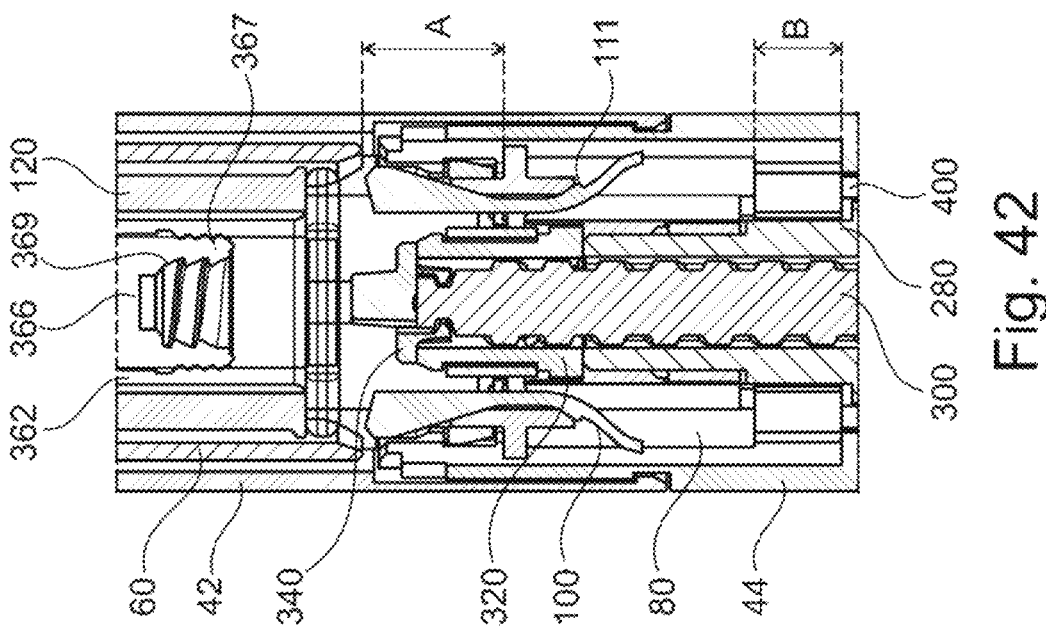
FIG. 42 shows a cross-sectional view of part of the autoinjector of FIG. 29 before use but after removal of the cap.

In FIG. 42, the cap (not shown) of the device has now been removed. This allows the needle guard to move in the proximal direction, although this feature is optional and the needle guard could also not move when the cap is removed.

In FIG. 43, the device is shown once the needle guard 60 has been moved fully in the distal direction. Compressing the needle guard in this way to activate the device puts the needle guard in a position to block the needle guard lock 100 from flexing out. When the needle guard 60 is compressed far enough (i.e. pushed far enough in the distal direction—namely the distance A as shown in FIG. 42), it will begin pushing the lock activation sleeve 80 in the distal direction. Pushing the lock activation sleeve in the distal direction flexes the distal part 108 of the needle guard lock arm inwards, subjecting it to internal bending stresses which make the needle guard lock arm 104 try to pivot. Since the proximal part 106 of the needle guard lock arm cannot flex outward until the needle guard 60 is re-extended (moves back in the proximal direction), the arm 104 remains in a biased state during the injection. The intention is that the user should push the needle guard all the way to its most distal position (in this case, this is after the needle guard has been pushed the distance A in FIG. 42 plus the distance B in FIG. 42) and thereby activate the device, thereby also pushing the lock activation sleeve 80 to its most distal position (in this case, the most distal position is when a distal-facing surface on the lock activation sleeve 80 faces a proximal-facing surface on the spring holder, although the most distal position of the lock activation sleeve 80 could be set by abutting another part, such as the housing, or could simply be limited by the limited movement of the needle guard instead). This can help define how deeply a needle penetrates the injection site, or how a jet injector interacts with the injection site.

The point at which the needle guard lock 100 is activated by the lock activation sleeve 80 can be set by the relative shape and size of the components. For example, the point at which the injection starts (which in this example is set by the point at which the lock activation sleeve 80 releases the arms 324 of the driver nut 320, thereby disengaging the teeth 286 of the driver 280 from the teeth 326 of the driver nut 320) can be at the same point where the device would lock if the needle guard is prematurely re-extended (moved back in the proximal direction, for example by premature removal of the device from the injection site). This would mean that the needle guard lock assembly would lock the needle guard if the injection had started and was then removed (either at the end of the injection or prematurely), but would not lock the needle guard if the injection had not started. Alternatively, the point at which the injection starts could be before or after the point at which the needle guard lock 100 is activated by the lock activation sleeve 80.

FIG. 44 shows the needle guard lock assembly and the driver nut after the injection has finished (or after the device has prematurely been removed from the injection site). The lock activation sleeve 80 remains in position, and the movement of the needle guard 60 back in the proximal direction allows the arms 84 of the lock activation sleeve 80 to relax their bias by movement of the proximal part 106 of the needle guard lock arm 104 away from the axis 20. In this example, the proximal part 106 of the needle guard lock arm 104 abuts the distal housing 44 in the slit 45, although a gap between the distal housing 44 and the proximal part 106 of the needle guard lock arm 104 is alternatively possible (as is shown in the example in FIG. 3).

FIG. 45 shows the detail of the needle guard lock 100 and its interaction with the slit 45 in the distal housing 44. Typically, as shown in FIGS. 44 and 45, a small gap in the axial direction is present between the needle guard 60 and the needle guard lock 100 (specifically the proximal part 106 of the needle guard lock arm 104), allowing for a small amount of travel for the needle guard after injection. This can be beneficial in terms of increasing tolerance in component dimensions.

Figures 46, 47, 48, 49, 50, 51:
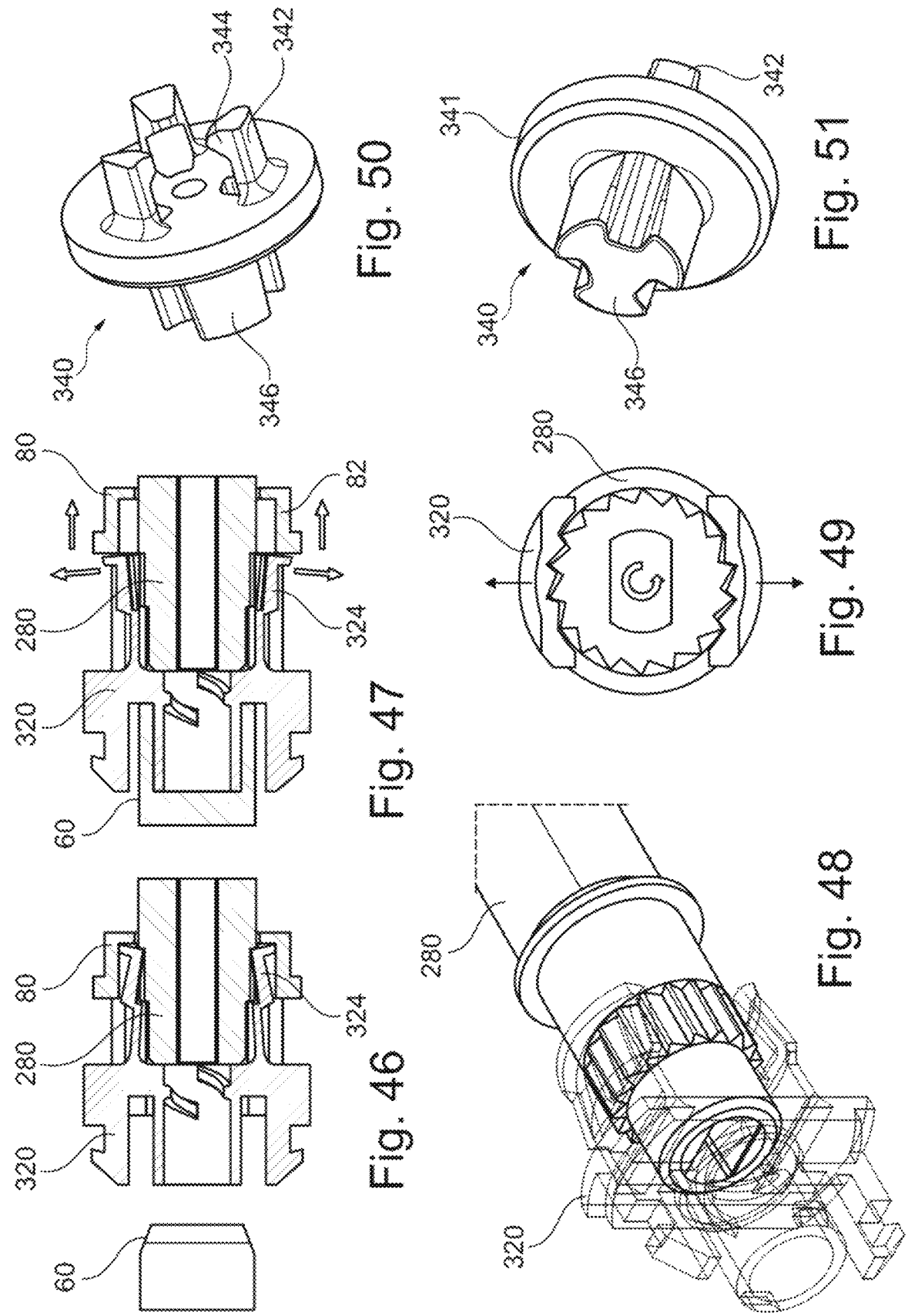
FIG. 46 shows a cross-sectional view of some components of the autoinjector of FIG. 29 before use.
FIG. 47 shows a cross-sectional view of the components of FIG. 46 after activation.
FIG. 48 shows a perspective view of the driver and the driver nut of the autoinjector of FIG. 29 before use.
FIG. 49 shows a cross-sectional view in the axial direction of the driver and the driver nut of the autoinjector of FIG. 29 before use.
FIG. 50 shows a perspective view of the thrust bearing of the autoinjector of FIG. 29.
FIG. 51 shows another perspective view of the thrust bearing of the autoinjector of FIG. 29.

FIGS. 46 and 47 show the relative positions of the needle guard 60, the lock activation sleeve 80 and the driver nut 320 before and after device activation. When the arms 324 of the driver nut 320 move radially outward (away from the axis), the driver 280 is allowed to rotate as previously described. As can be seen in FIG. 47 in particular, in this example the arms 324 move radially outward to a position where they align with the tubular section 82 of the lock activation sleeve 80, so that a distally facing surface of the arm 324 engages a proximally facing surface of the tubular section 82 of the lock activation sleeve. This alignment is optional, but can be beneficial in that it can stop the lock activation sleeve from moving back in the proximal direction after the needle guard 60 moves back in the proximal direction. Alternatively or additionally, the lock activation sleeve is prevented from moving back in the proximal direction by friction, for example friction between the pad 86 of the lock activation sleeve and the distal part 108 of the needle guard lock arm 104 once the arm 104 is biased. A protrusion such as the optional protrusion 111 (see FIG. 26 or FIG. 42) on the distal part 108 of the needle guard lock arm could alternatively or additionally be provided-such a protrusion can interact with the distal part of the pad 86 to help restrict unintentional movement in the distal direction of the lock activation sleeve prior to injection.

FIGS. 48 and 49 show details of how the driver 280 and the driver nut 320 fit together. Preferably, it is not only internal bending stresses of the arms 324 of the driver nut 320 that cause the arms to swing outward once permitted, but also the sloped interfaces of the teeth of the driver 280 and arms 324 which can contribute towards pushing the arms outwards, as shown in FIG. 49 in particular. The angle can be particularly designed such that the arms 324 are pushed outwards with as little force as possible, although always with enough force to not jam (i.e. so that the injection always commences as designed). The force of the arms pressing outward against the activation ring creates friction, friction which the user must overcome in order to activate the device, hence it is beneficial to design the force being overcome to be as low as possible. Further details of drivers that could be used in this type of device are described in EP 19211853.7, the full content of which is incorporated herein by reference.

FIGS. 50 and 51 show an example thrust bearing 340 for the autoinjector of FIG. 29, though this thrust bearing could also be used in the other autoinjectors described herein. The thrust bearing comprises an optional base 341, one or more snap fit arms 342 (in this case three arms) to engage the proximal end of the plunger rod 300 (see for example FIGS. 26 and 35), each arm including a protrusion 344 to engage the plunger rod, and a proximally facing protrusion 346 to engage the stopper during an injection. The snap fit arms would typically be flexible to help with assembly. The thrust bearing 340 in general and the proximally facing protrusion 346 in particular can beneficially be varied to correspond to different shaped stoppers, as it can be beneficial to have a large area of contact between the thrust bearing and the stopper to support the stopper, particularly where a viscous medicament is being provided and therefore a high spring force needs to be transferred from the powerpack to the stopper. With some shapes of stopper, a proximally facing protrusion may not be necessary at all. The thrust bearing should generally be free to rotate relative to the plunger rod—this ensures that when the thrust bearing comes into contact with the syringe stopper it does not rotate with the plunger rod and only transmits the linear force.

Figure 52:
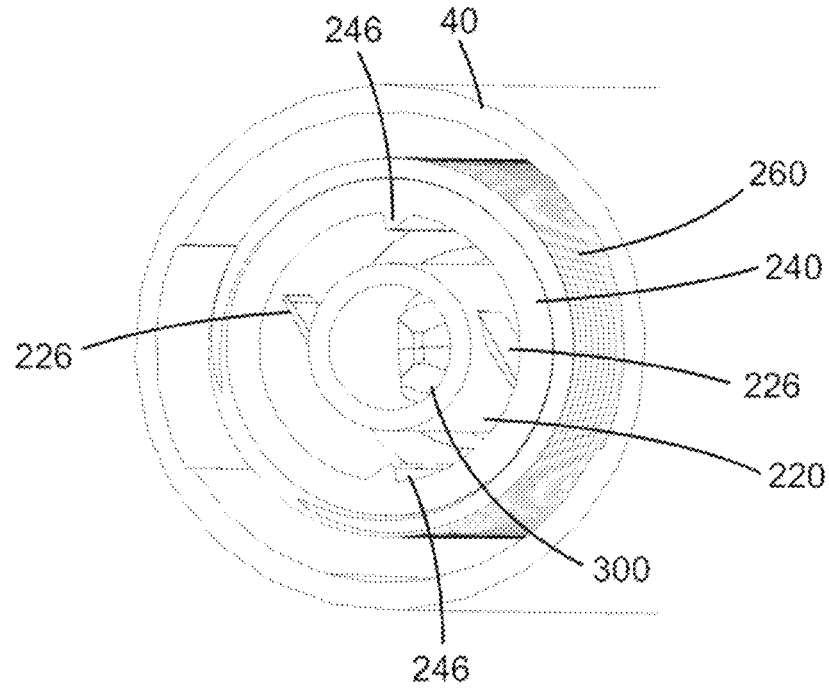
FIG. 52 shows a cross-sectional and perspective view of part of another similar example autoinjector, showing features that allow the powerpack lock and powerpack housing to interact to create clicks during injection.

FIG. 52 shows part of another example autoinjector with slightly differing features, although the features shown in this example can also be provided in the fully described examples above. In this example, the protrusions 226 of the powerpack lock 220 can be seen, along with corresponding ribs 246 on the powerpack housing 240. In general, the shape of the protrusions 226 and the ribs 246 can be varied, as can the number of protrusions 226 and ribs 246. The same number of protrusions and ribs are provided (two of each in this example), but different numbers could be provided, for example two protrusions and four ribs. The ribs can be replaced by protrusions. The number, shape and precise location of the protrusions and ribs can be varied depending on the number and pattern of clicks desired. As shown in FIG. 52, the ribs 246 can have a slanted face on one side (face extending both in the radial and circumferential directions) (specifically, this is the side that the protrusions 226 would reach first as the powerpack lock and the powerpack housing rotate relative to each other during injection) to allow the protrusions 226 to ride up the ribs 246 more gently. The other side of the ribs would typically have a steeper face (e.g. extending in the radial direction). Alternatively or additionally, as shown in FIG. 52, the protrusions can be slanted (extending both in the radial and circumferential directions, and not extending directly outwards from the axis) to allow the protrusions 226 to ride up the ribs 246 more gently. The slanted face of the ribs and the slanted protrusions can also help reduce the friction of the parts as they pass one another. In FIG. 52, the plunger rod 300 (specifically the distal end of the plunger rod 300) can be seen inside the powerpack lock 220.

In addition to the examples and alternatives described above, further examples and alternatives will now be described with reference to FIG. 53 onwards. These examples partially focus on mechanisms for stopping medicament delivery devices from activating prematurely (i.e. before the cap is taken off). This problem can arise in particular when a device is dropped, with the momentum of a needle guard causing the needle guard to move in the distal direction relative to the housing when the medicament delivery device hits the ground.

Figure 53:
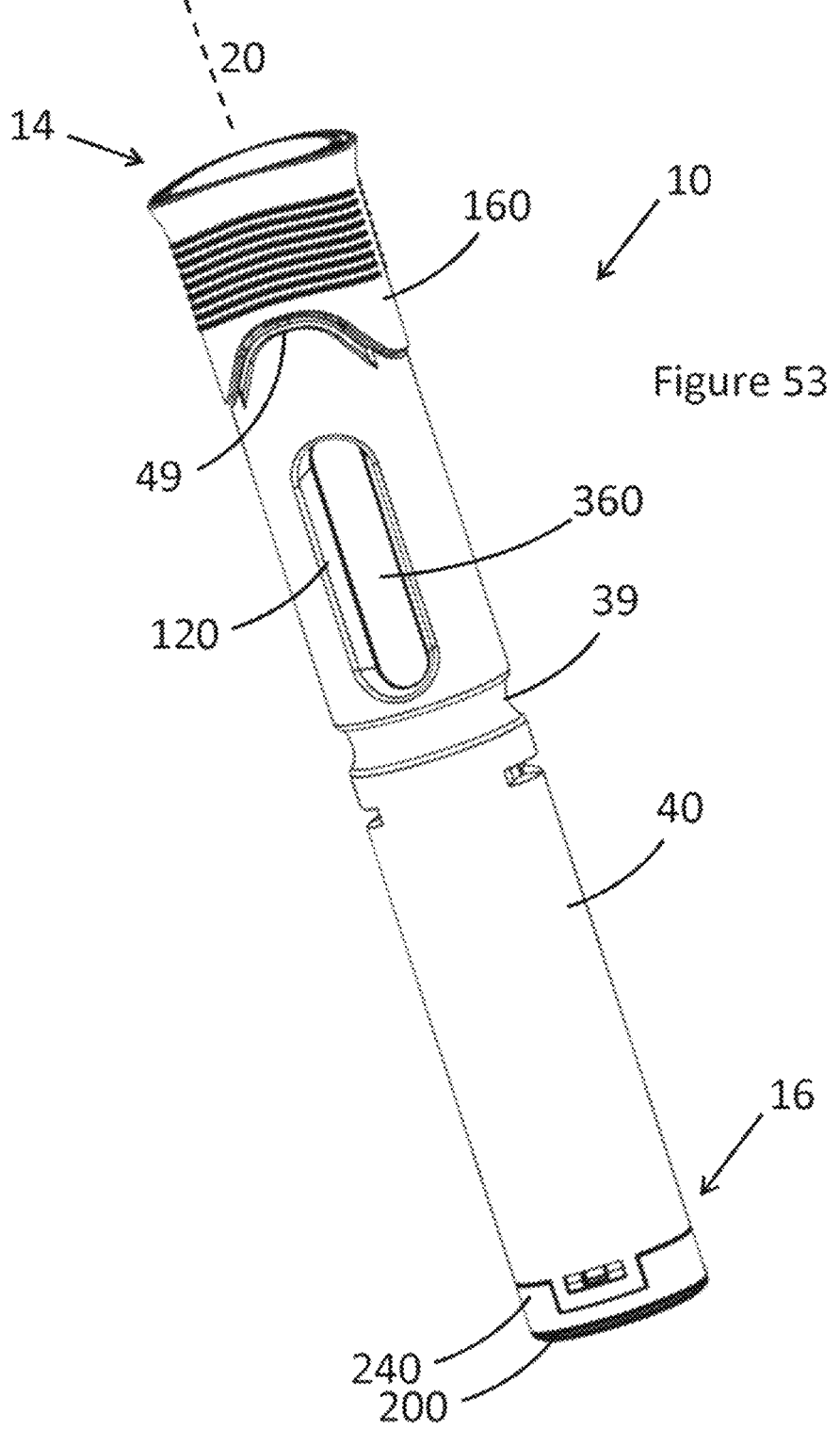
FIG. 53 shows a perspective view of an example autoinjector.

FIG. 53 shows an autoinjector 10 with a similar assembly to those described above. In FIG. 53, a housing 40, a cap 160 and an optional end cap 200 can be seen, along with small portions of a syringe holder 120, a powerpack housing 240 and a primary package 360.

Figure 54:
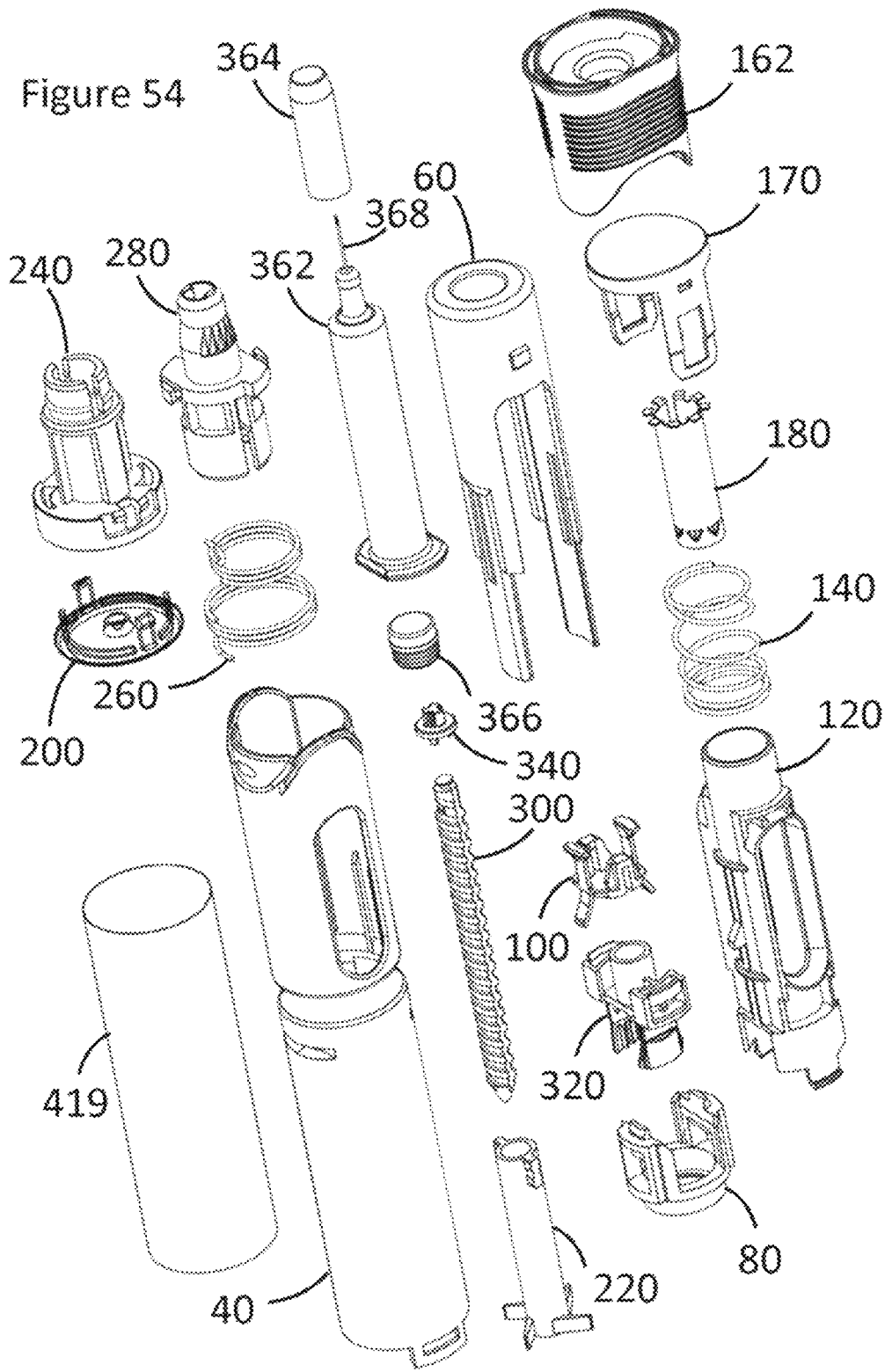
FIG. 54 shows an exploded perspective view of the autoinjector of FIG. 53.

FIG. 54 shows the parts of the autoinjector 10 of FIG. 53 disassembled, namely the housing 40, a needle guard 60, a lock activation sleeve 80, a needle guard lock 100, the syringe holder 120, a needle guard spring 140, the cap (comprising a cap housing 162, a cap insert 170, and a rigid needle shield remover 180 in this example), the optional end cap 200, a powerpack lock 220, the powerpack housing 240, a torsion spring 260 (in FIG. 54, the torsion spring is not shown fully, and just the two ends are shown—one end untensioned and the other end tensioned—to show a typical difference in diameter between the tensioned and unten-sioned state), a driver 280, a plunger rod 300, a driver nut 320, a thrust bearing 340, and the primary package (in this example comprising a syringe 362 with a needle 368, a rigid needle shield 364 and a stopper 366). An optional label 419 is also shown. The label can cover up features such as the clip between the housing and the powerpack housing. Covering up such features can be beneficial as it can help avoid end users trying to take apart the device. The label is shown extending the entire way around the housing, but could also extend only part of the way round the housing.

Figures 55, 56, 57:
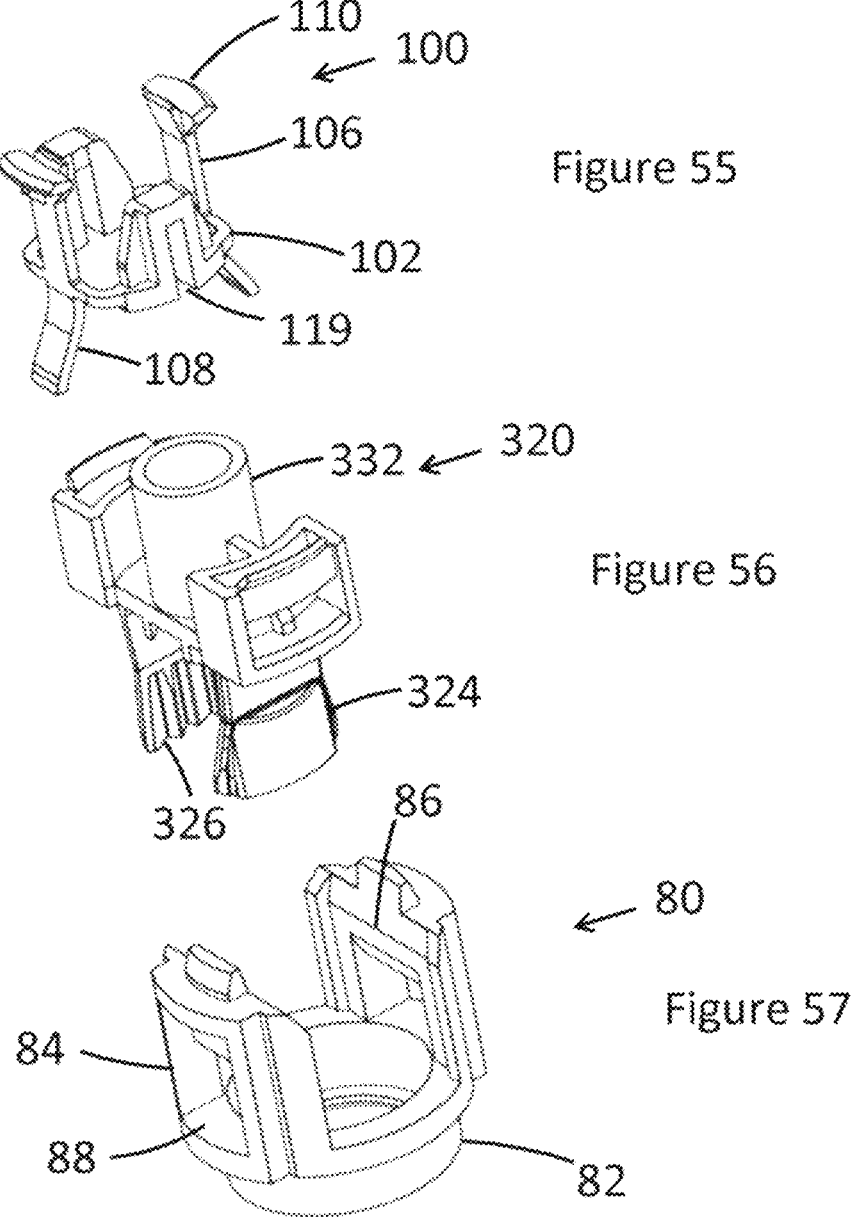
FIG. 55 shows a perspective view of the needle guard lock of FIG. 54.
FIG. 56 shows a perspective view of the driver nut of FIG. 54.
FIG. 57 shows a perspective view of the lock activation sleeve of FIG. 54.
Figures 58, 59, 60, 61:
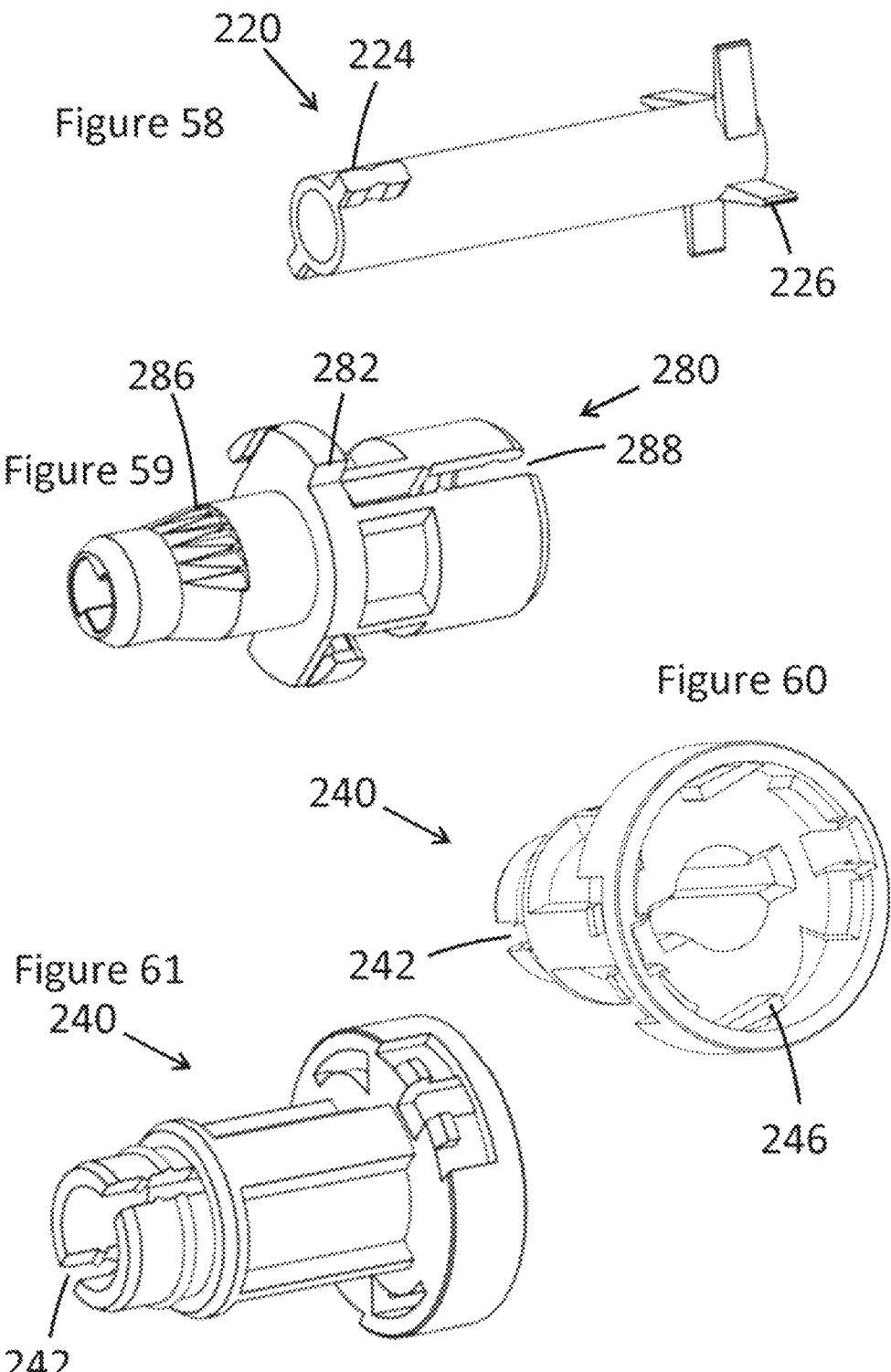
FIG. 58 shows a perspective view of the powerpack lock of FIG. 54.
FIG. 59 shows a perspective view of the driver of FIG. 54.
FIG. 60 shows a perspective view of the powerpack housing of FIG. 54.
FIG. 61 shows another perspective view of the powerpack housing of FIG. 54.
Figures 62, 63:
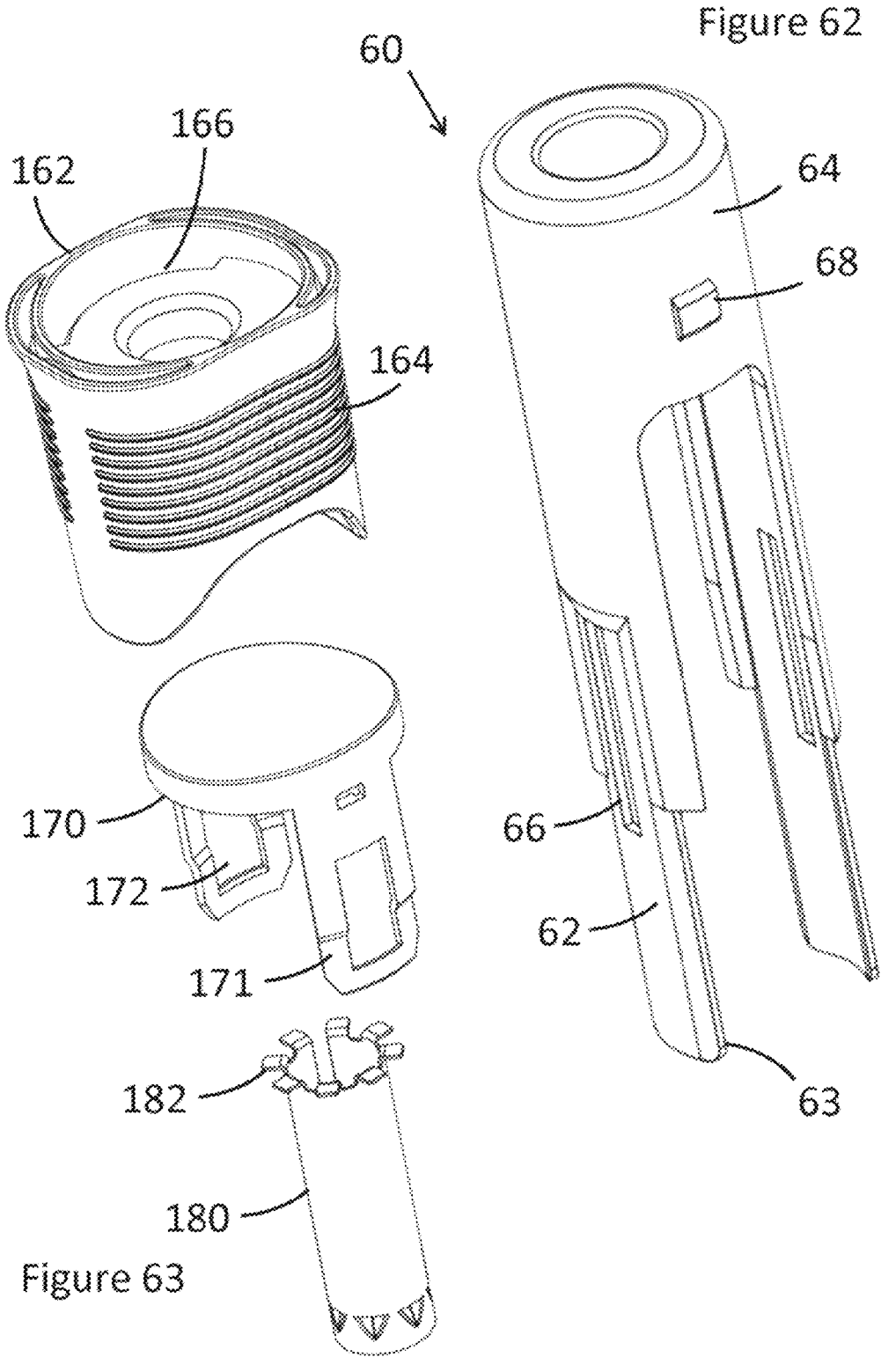
FIG. 62 shows a perspective view of the needle guard of FIG. 54.
FIG. 63 shows a perspective view of the components of the cap of FIG. 54.

The parts are generally interchangeable between the devices described herein. Nevertheless, some of the components are somewhat different in shape to those described elsewhere herein. Some of the components are shown in more detail in FIGS. 55 to 62. FIGS. 55, 56 and 57 show further detail of the needle guard lock 100, driver nut 320 and lock activation sleeve 80 respectively. FIG. 58 shows further detail of the powerpack lock; in this example, the protrusions 226 are at the distal end of the powerpack lock, rather than spaced apart from the distal end of the powerpack lock as in FIG. 15, for example. FIG. 59 shows further detail of the driver 280, and FIGS. 60 and 61 show further detail of the powerpack housing 240. FIG. 62 shows further detail of the needle guard 60.

FIG. 63 shows the three components of an example cap 160, namely the cap housing 162, the cap insert 170 and the rigid needle shield remover 180. FIGS. 64 to 69 show the cap in various positions to provide more detail.

Figure 64:
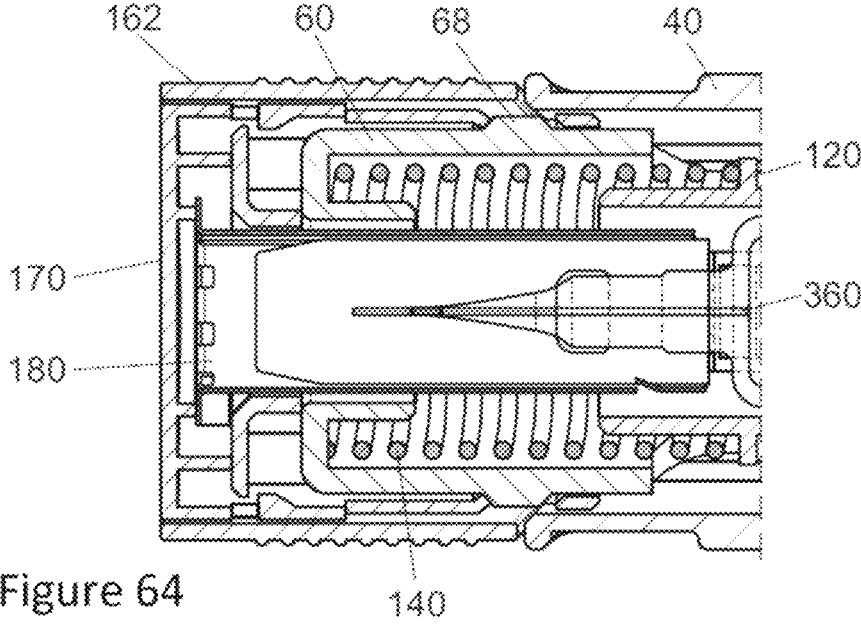
FIG. 64 shows a cross-section view of part of the autoinjector of FIG. 53 prior to cap removal.
Figures 68, 69:
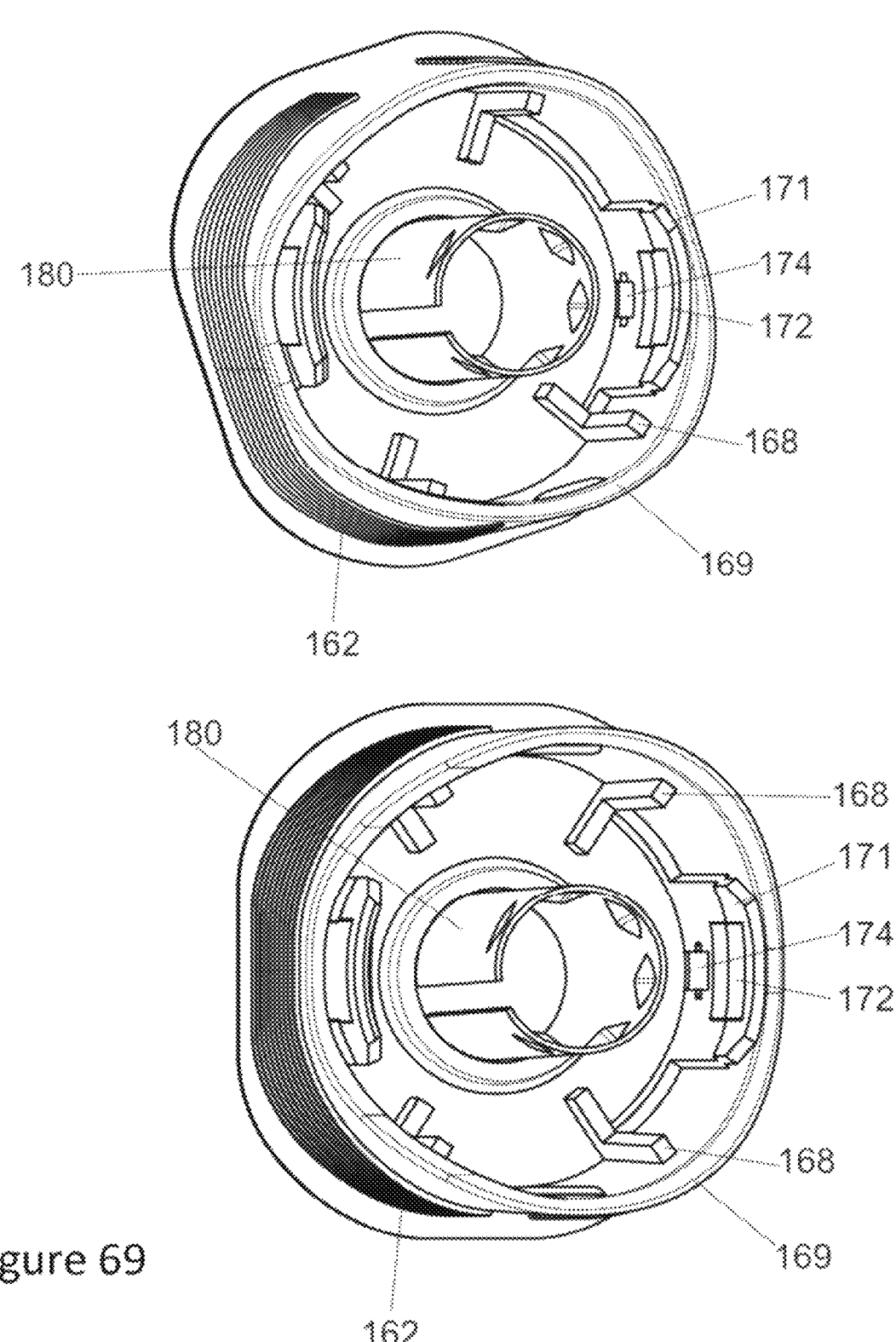
FIG. 68 shows a perspective view of the cap of FIG. 53 during cap removal by twisting.
FIG. 69 shows a perspective view of the cap of FIG. 53.

FIG. 64 shows the cap and the adjacent parts of the medicament delivery device for context. The focus here is on the lock mechanism provided by a combination of the cap 160, the needle guard 60 and the housing 40. For context, the primary package 360, the optional needle guard spring 140, and the syringe holder 120 are also visible. The cap 160 comprises a cap housing 162, a cap insert 170 and a rigid needle shield remover 180. In this case, the cap housing 162 provides the outer casing of the cap. The cap housing 162 is typically a tubular body, as can be seen in FIG. 63, and comprises an optional grip 164 and a slot 166 through which the cap insert arm 171 extends as can be seen in FIG. 69, for example. The cap insert 170 comprises a cap insert arm 171, and the cap insert arm 171 comprises a cut-out 172 (although this could alternatively be a recess). The cap insert 170 also comprises a snap fit protrusion 174 as can be seen in FIG. 69, for example. The rigid needle shield remover 180 is arranged between the cap insert 170 and the cap housing 162, with the rigid needle shield remover flange 182 extending between the cap housing 162 and the cap insert 170 to hold the rigid needle shield remover flange 182 in place.

The cap insert 170 is restricted from moving in the axial direction 22 relative to the cap housing 162 by the snap fit protrusion 174 of the cap insert 170, which abuts a proximally facing surface of the cap housing 162 as can be seen in FIG. 69, for example. The snap fit allows for rotational movement of the cap housing 162 relative to the cap insert 170; optionally, this rotational movement is limited by ribs 168 of the cap housing 162 (see FIG. 69 for example), which can engage a circumferentially facing surface of the cap insert arm 171 to restrict the rotational movement of the cap insert 170 relative to the cap housing 162. In this example, the ribs extend from an inner surface of the cap body, but could alternatively extend outward from an extra outwardly facing surface arranged within the cap body. Provision of a snap fit can be beneficial due to ease of assembly, but the snap fit is optional and could be replaced by various other structural features configured to achieve the same axial movement restriction, such as a protrusion, a rib or an arm, for example.

The cap 160, and particularly the arm 171 of the cap housing 162, is inside the housing 40 (specifically the proximal end of the housing 40). The needle guard 60 is inside the cap 160 (specifically inside of the cap insert arm 171). The needle guard 60 comprises a protrusion 68 extending away from the axis in the radial direction and extending into the cap insert cut-out 172.

Figure 65:
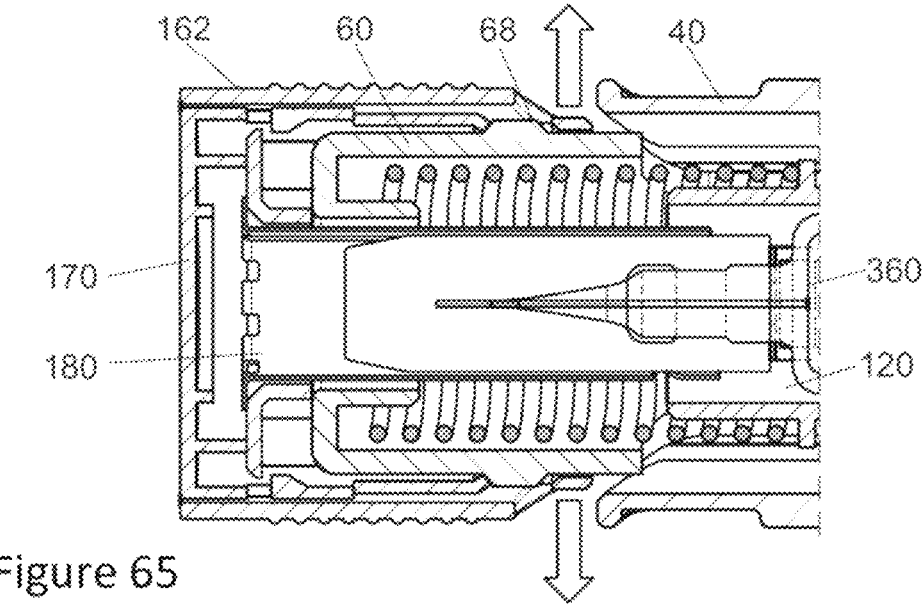
FIG. 65 shows a cross-section view of part of the autoinjector of FIG. 53 during cap removal.

During use, the cap is first pulled away from the housing, resulting in movement of the medicament delivery device from the position shown in FIG. 64 to the position shown in FIG. 65. The cap and the needle guard are moved in the proximal direction relative to the housing (movement of the needle guard can be due to the cap pulling the needle guard and/or due to the needle spring pushing the needle guard in the proximal direction once the cap is no longer restricting proximal movement of the needle guard, for example). The result of this is that the cap insert arm 171, which was initially restricted from moving in the radial direction by the presence of the housing 40, is now free to move in the radial direction, thereby allowing the cap insert arm 171 (and thereby the rest of the cap) to continue moving in the proximal direction relative to both the housing 40 and the needle guard 60, thereby moving the protrusion 68 of the needle guard 60 out of the cap insert cut-out 172.

Figure 66:
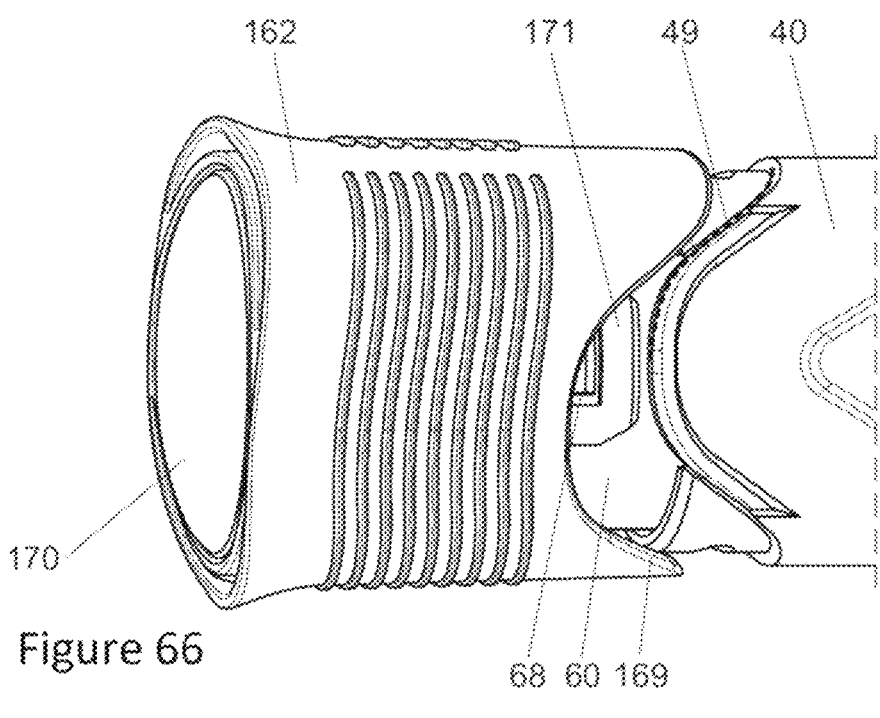
FIG. 66 shows a perspective view of part of the autoinjector of FIG. 53 during cap removal by twisting.
Figure 67:
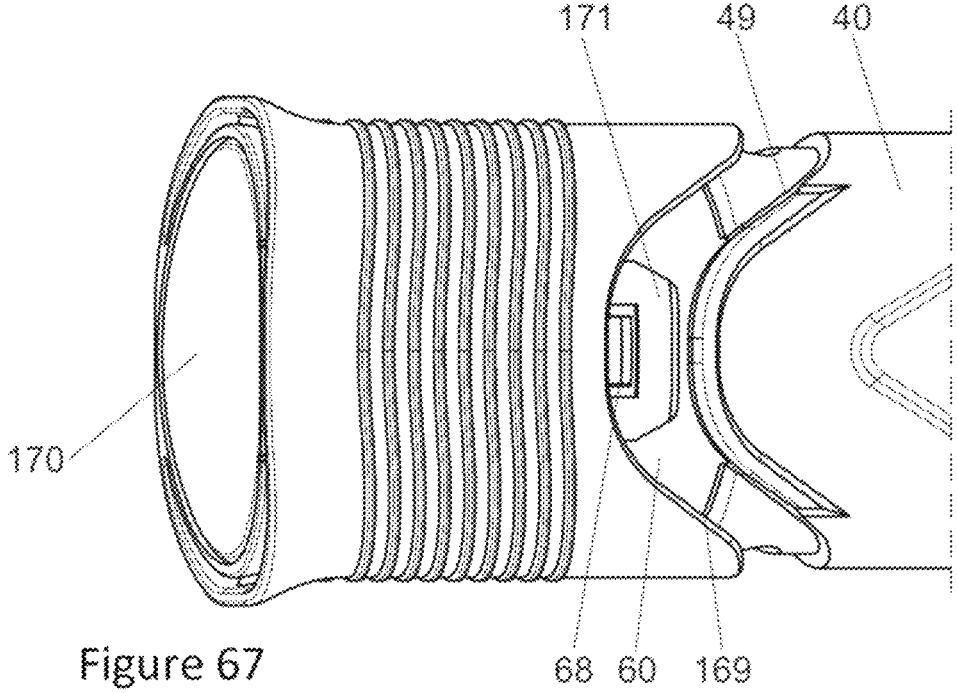
FIG. 67 shows a perspective view of part of the autoinjector of FIG. 53 during cap removal.

In this particular example, the cap is designed so that continued pulling of the cap in the axial direction removes the cap from the autoinjector (medicament delivery device) (FIG. 67). A rotation of the cap relative to the housing can additionally or alternatively be carried out to remove the cap (see FIG. 66). As can be seen in FIG. 66 in particular, a proximally facing surface 49 of the housing extends in the circumferential direction 24 around the housing, and faces a corresponding distal facing surface 169 of the cap 160 (specifically of the cap housing 162 in this example). Both the proximally facing surface 49 of the housing 40 and the distal facing surface 169 of the cap housing 162 extend in the axial direction, with the axial position varying around the circumference—in this case in a sinusoidal pattern, although other shapes are also possible. Having the axial position vary like this in the circumferential direction is optional, but can be beneficial as it can mean that initiation of cap removal by twisting the cap relative to the housing will naturally result in movement of the cap relative to the housing in the axial direction as well.

The cap and lock mechanism described above and with reference to FIGS. 63 to 69 are an example of a cap and a corresponding lock mechanism more generally, and this particular design can also be modified in various ways in addition to the options already mentioned above. A selection of other example modifications will now be described. For example, the cap described above comprises three parts, but a cap consisting of another number of parts or even a single integral part could be used instead. The cut-out does not have to be in an arm, though this may help with flexibility and make it easier for the protrusion to be removed from the cut-out during cap removal. In the example above, the protrusion is provided on the needle guard and a cut-out is provided on the cap, but this could also be reversed with the cut-out in the needle shield rather than on the cap. The functionality of rotation of the cap housing 162 relative to the cap insert 170 is optional; when this functionality is provided, it can be beneficial for both the cap housing 162 and the cap insert 170 to be tubular to allow rotational movement relative to one another. Instead of the housing being further from the axis than the needle guard and the arm of the cap, the housing could alternatively be closer to the axis than the needle guard and the arm of the cap, with the mechanism effectively inverted in the radial direction 26.

Figure 70:
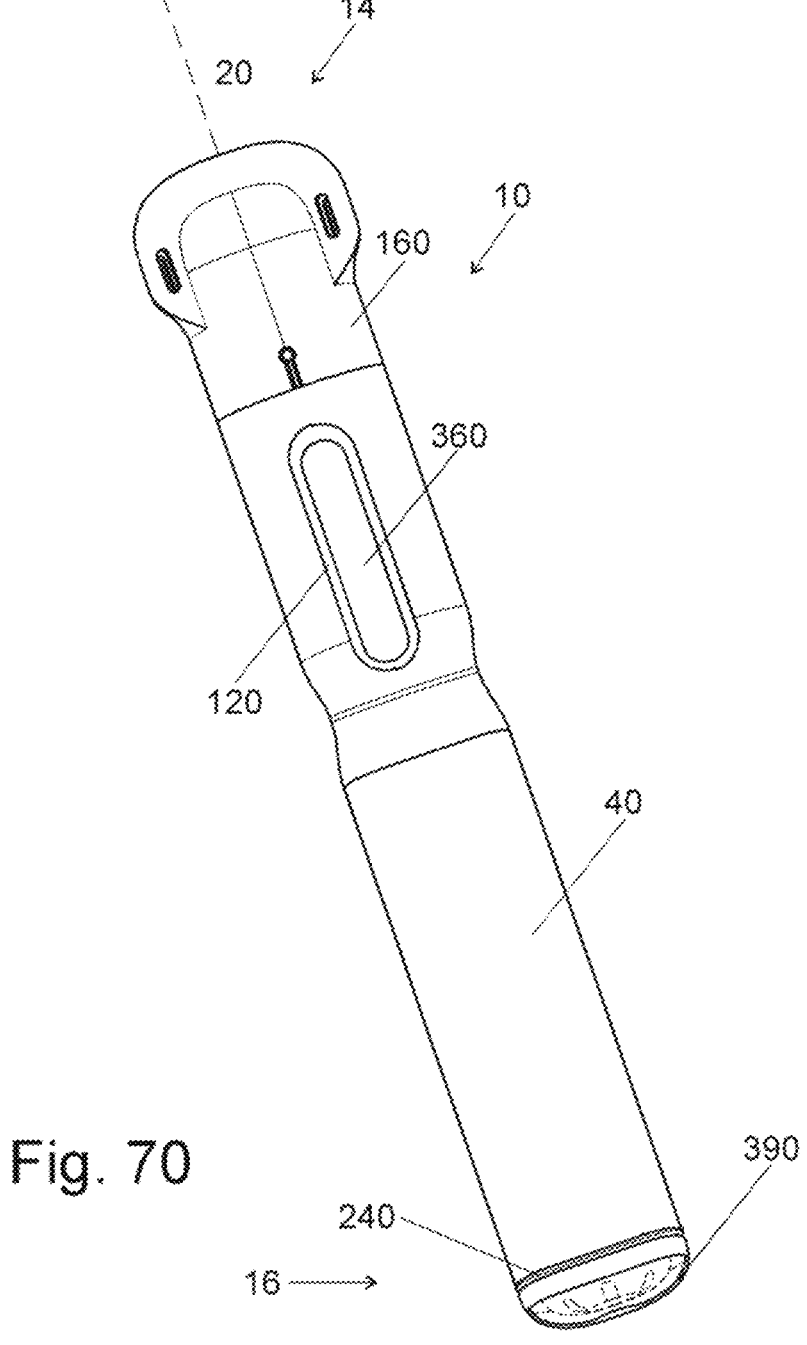
FIG. 70 shows a perspective view of another example autoinjector.

FIG. 70 shows another autoinjector 10 with a similar assembly to those described above. In FIG. 70, a housing 40, a cap 160, and an optional spinner cap 390 can be seen, along with small portions of a syringe holder 120 and a primary package 360. One visible difference compared to the previous designs is the design of the cap 160, which will be described in more detail below.

Figure 71:
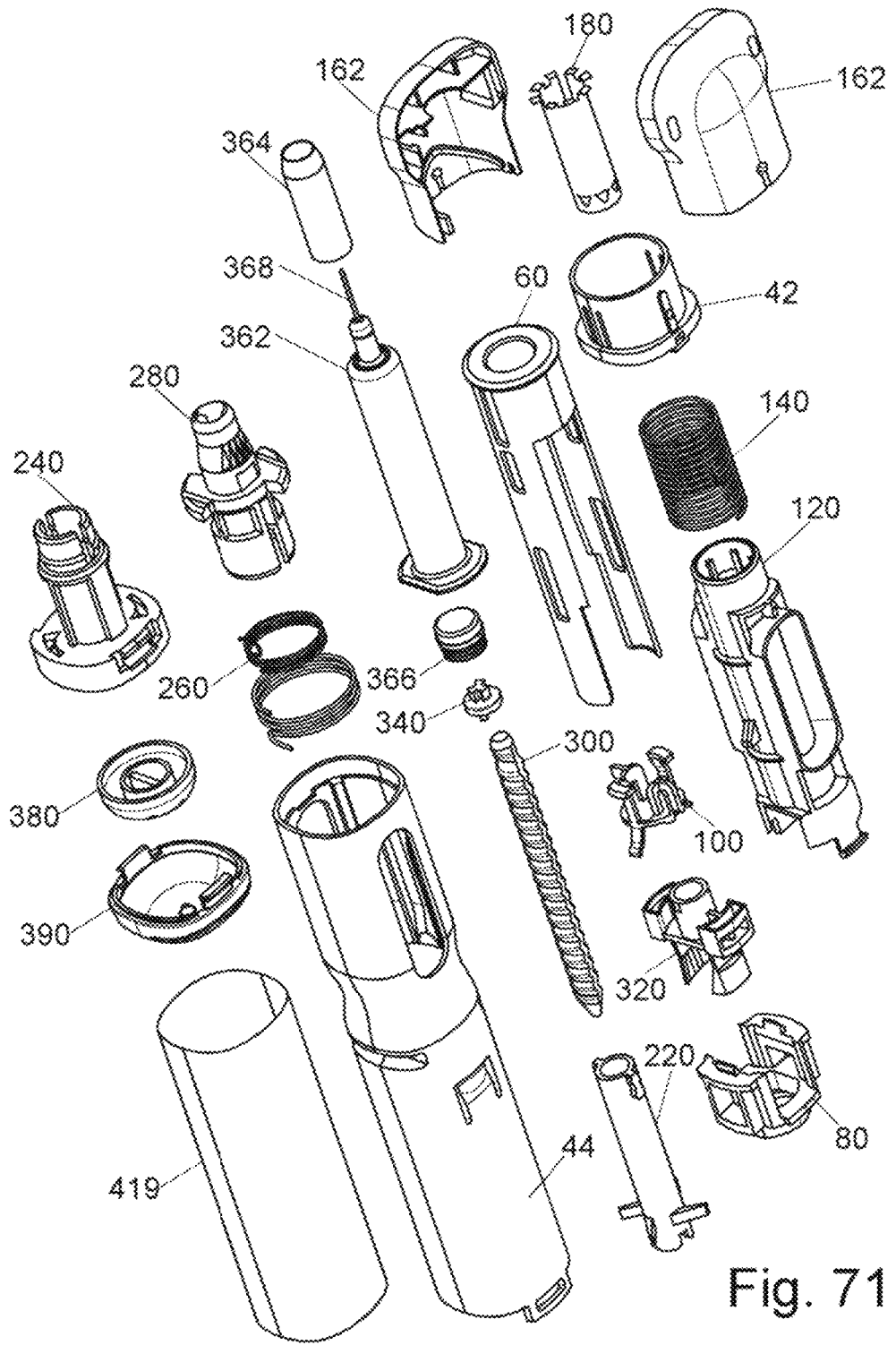
FIG. 71 shows an exploded perspective view of the autoinjector of FIG. 70.

FIG. 71 shows the parts of the autoinjector 10 of FIG. 70 disassembled, namely the housing (split into a proximal housing 42 and a distal housing 44), a needle guard 60, a lock activation sleeve 80, a needle guard lock 100, the syringe holder 120, a needle guard spring 140, the cap (comprising two cap housings 162), an optional spinner 380 and the spinner cap 390, a powerpack lock 220, the powerpack housing 240, a torsion spring 260 (in FIG. 71, the torsion spring is again not shown fully, and just the two ends are shown—one end untensioned and the other end tensioned—to show a typical difference in diameter between the tensioned and untensioned state), a driver 280, a plunger rod 300, a driver nut 320, a thrust bearing 340, and the primary package (in this example comprising a syringe 362 with a needle 368, a rigid needle shield 364 and a stopper 366). An optional label 419 is again also shown.

Figures 72, 73:
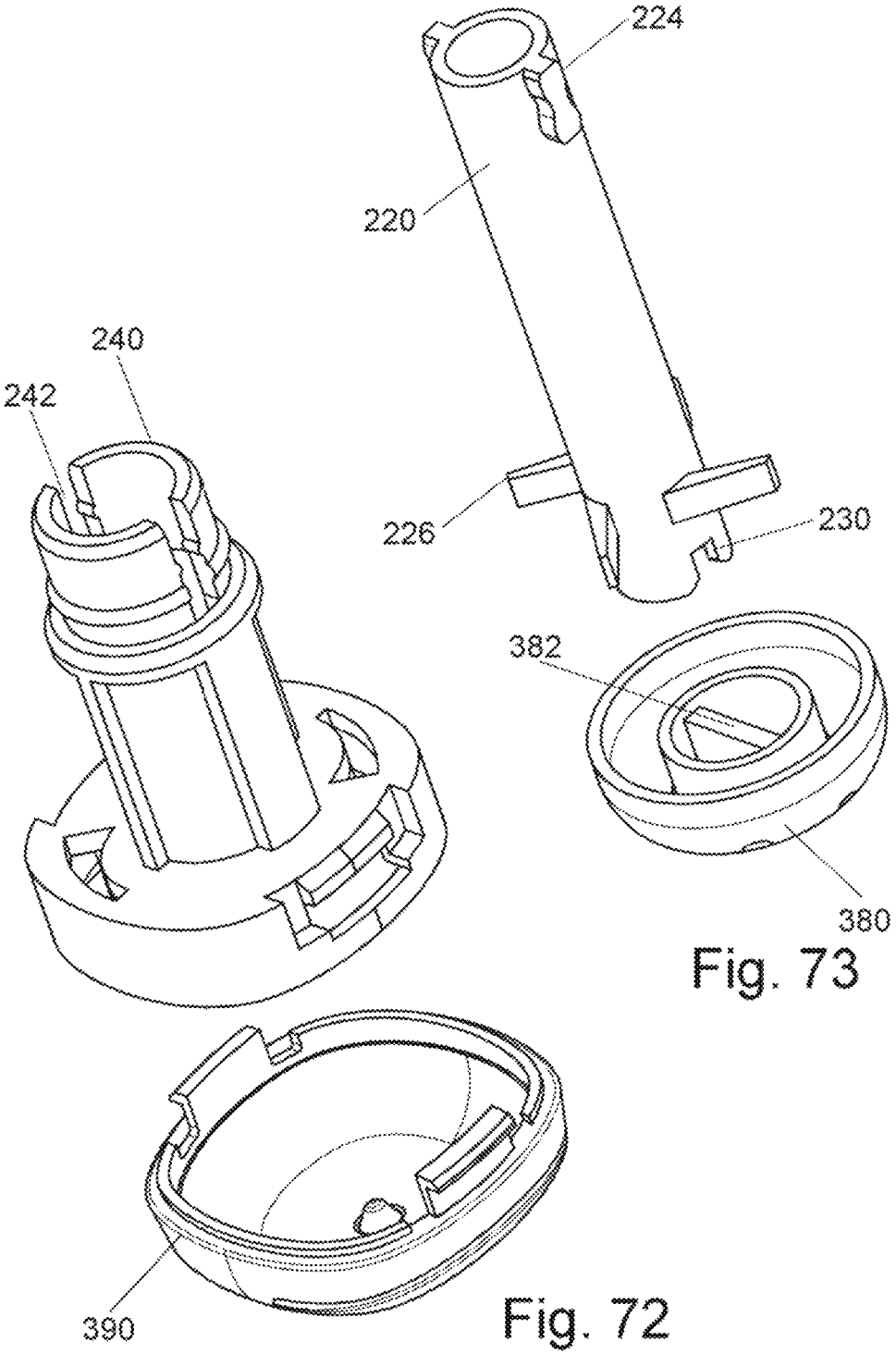
FIG. 72 shows a perspective view of the powerpack housing and the spinner cap of FIG. 71.
FIG. 73 shows a perspective view of the powerpack lock and the spinner of FIG. 71.

The parts are generally interchangeable between the devices described herein. Nevertheless, some of the components are somewhat different in shape to those described elsewhere herein. Some of the components are shown in more detail in FIGS. 72 to 81. FIG. 72 shows further detail of the powerpack housing 240 and the corresponding spinner cap 390, which can be joined together by a snap fit. FIG. 73 shows further detail of the powerpack lock 220 and the corresponding spinner 380, and shows one example of how the powerpack lock 220 and the spinner 380 could be attached together, namely by means of a spinner rib 382 of the spinner 380 engaged to a pair of distal notches 230 (the second notch is not visible) of the powerpack lock 220. The resulting rotation of the spinner 380 during medicament delivery can provide a visual indication that medicament delivery is underway. FIGS. 74 to 76 show details of how the distal end of the autoinjector fits together, focusing on the powerpack lock 220, the powerpack housing 240, the spinner 380, and the spinner cap 390. In FIG. 76, the relative position of the protrusions 226 of the powerpack lock 220 and the corresponding ribs 246 of the powerpack housing 240 can be seen. During drug delivery, rotation of the powerpack lock 220 relative to the powerpack housing 240 results in interaction between the protrusions 226 and the ribs 246, which can produce an audible indication that medicament delivery is in progress. To allow the protrusions 226 and the ribs 246 to pass one another, one or both of the protrusions 226 and the ribs 246 can be flexible. A tactile indication due to device vibration may also be produced, particularly if irregularly spaced ribs 246 and/or protrusions 226 are provided rather than the regular spacing shown in the illustrated example. This audible indication can be provided in addition to or alternatively to other audible, visual or tactile indications (for example in addition to or alternatively to a visual solution such as the spinner-based solution also shown in this particular embodiment). To enhance the visual effect of the spinner, patterns can be provided on the spinner (e.g. by printing, by adding a sticker or stickers, or by engraving) to make the rotation of the spinner more visible. The spinner could be an integral part of the powerpack lock rather than being a separate component. Alternatively or in addition to the feedback signals mentioned above, the plunger rod 300 could include a whistle hole. The whistle hole can generate an audio signal (typically a continuous audible signal) during medicament delivery. A whistle hole could also be provided in other plunger rods described herein.

Figures 77, 78, 79:
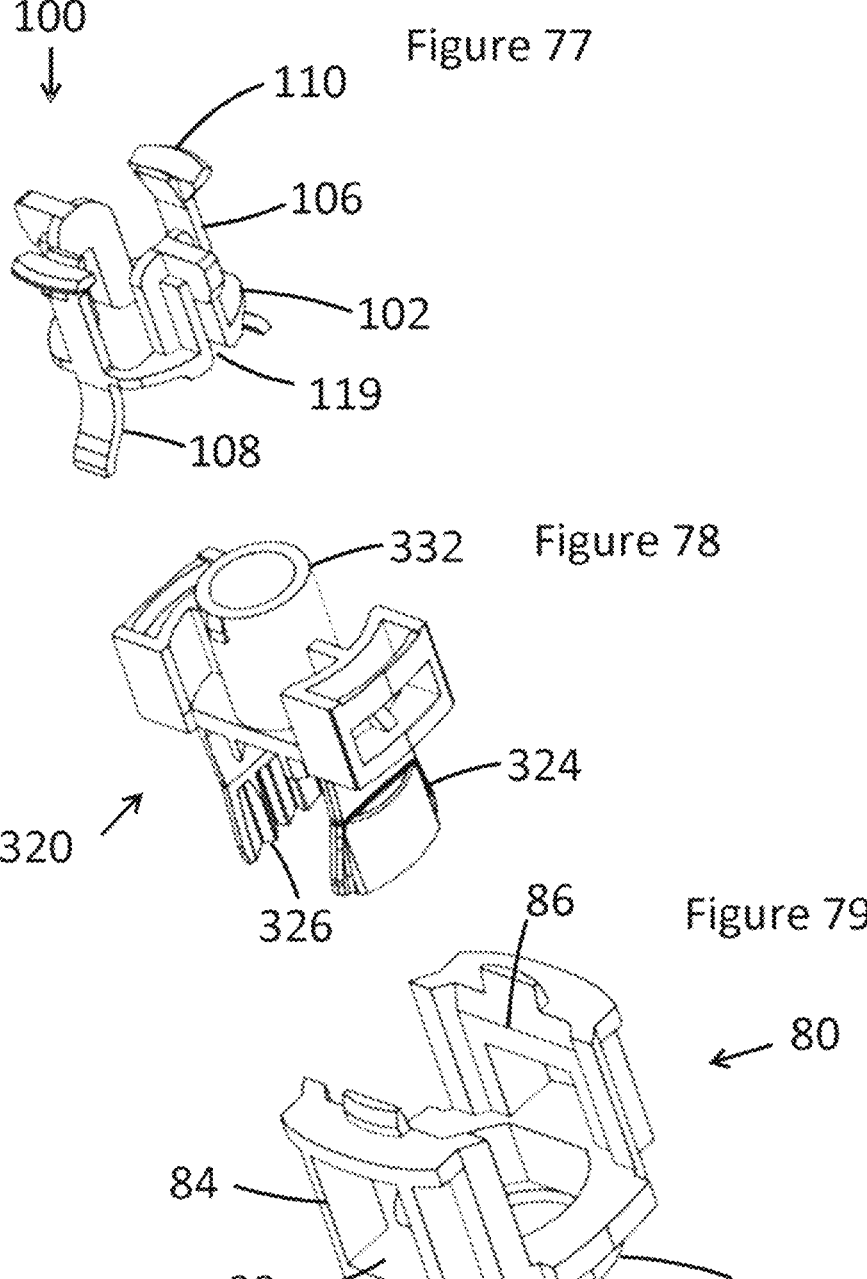
FIG. 77 shows a perspective view of the needle guard lock of FIG. 71.
FIG. 78 shows a perspective view of the driver nut of FIG. 71.
FIG. 79 shows a perspective view of the lock activation sleeve of FIG. 71.

FIGS. 77, 78 and 79 show further detail of the needle guard lock 100, the driver nut 320 and the lock activation sleeve 80 respectively.

Figure 80:
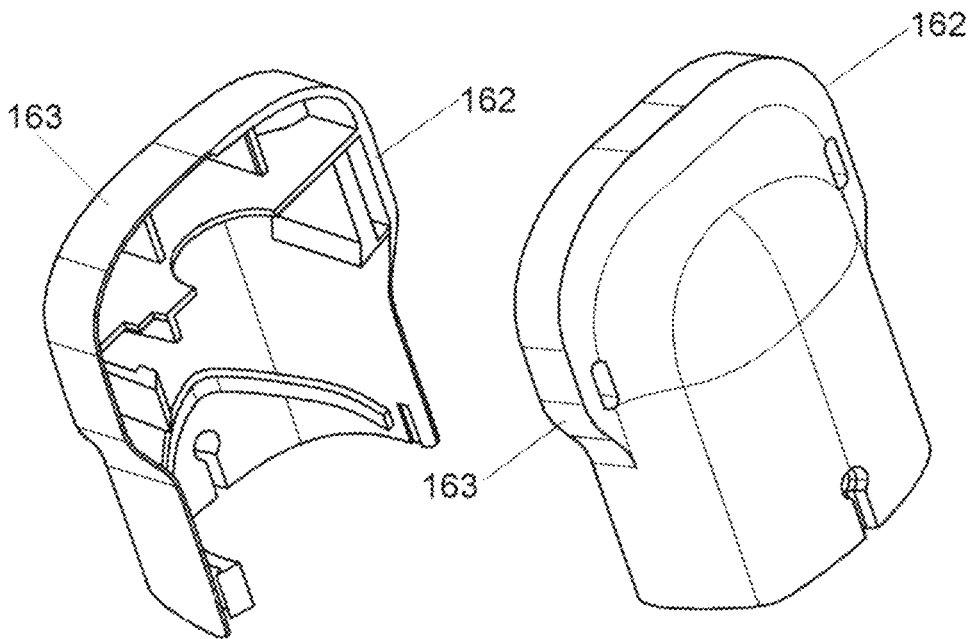
FIG. 80 shows a perspective view of the cap housing of FIG. 71.
Figure 81:
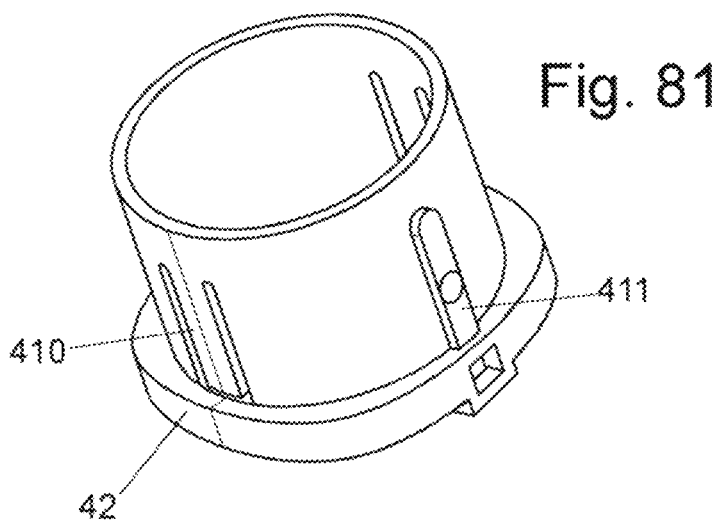
FIG. 81 shows a perspective view of the proximal housing of FIG. 71.
Figures 82, 83:
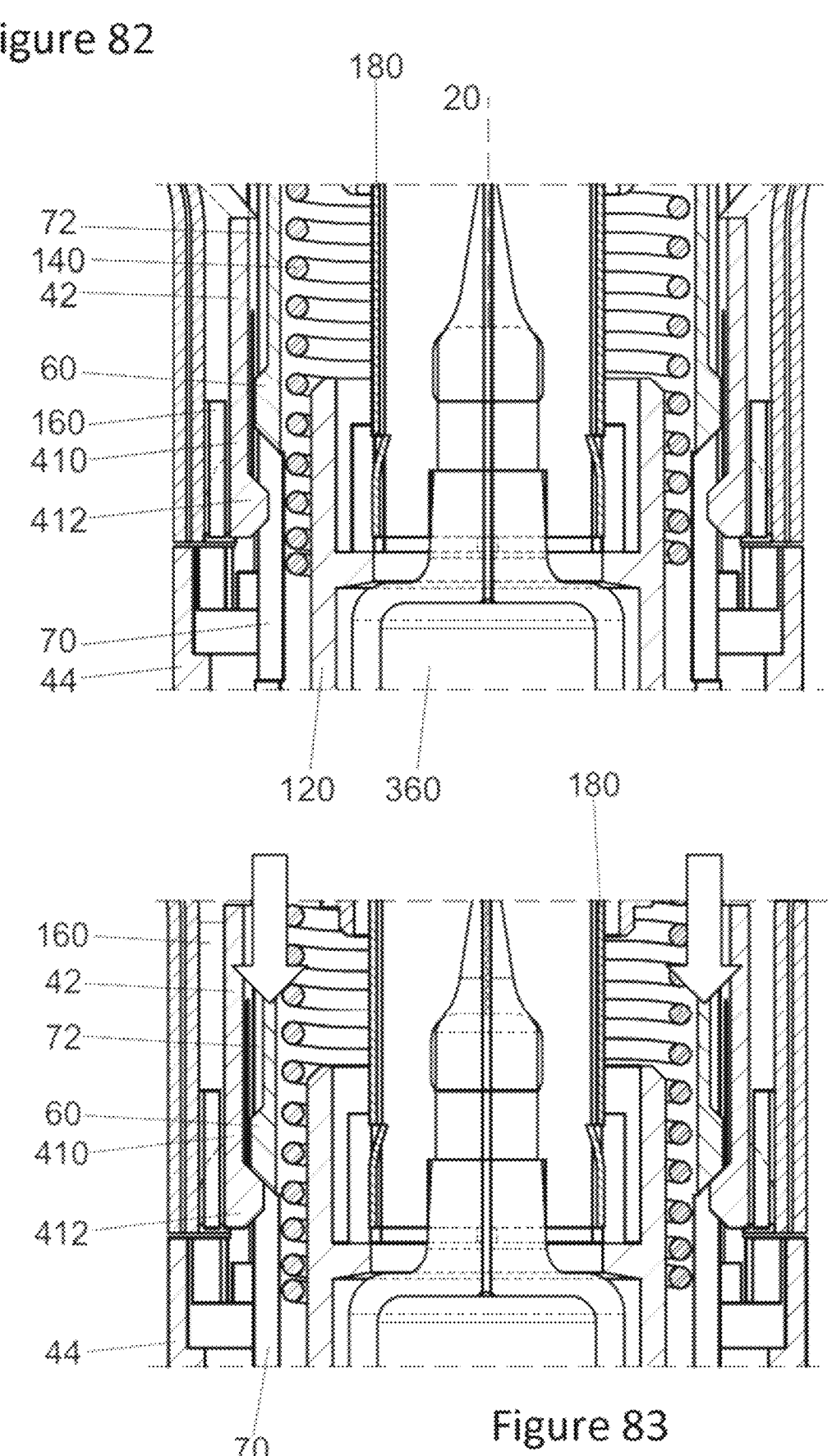
FIG. 82 shows a cross-section view of part of the autoinjector of FIG. 70 prior to use.
FIG. 83 shows a cross-section view of part of the autoinjector of FIG. 70 when the needle guard moves in the distal direction relative to the housing prior to removal of the cap.
Figure 84:
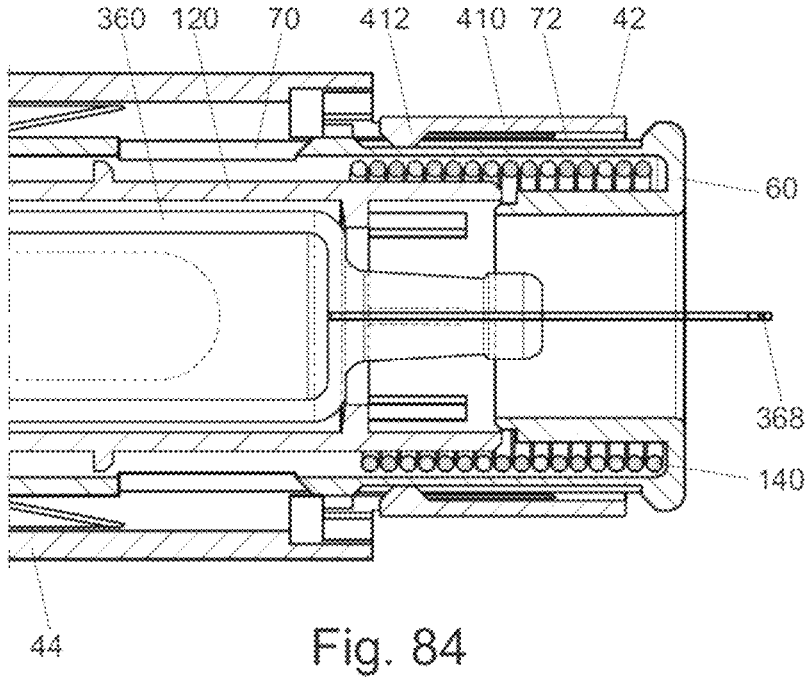
FIG. 84 shows a cross-section view of part of the autoinjector of FIG. 70 after the cap has been removed and after the needle guard has been moved in the distal direction relative to the housing.
Figure 85:
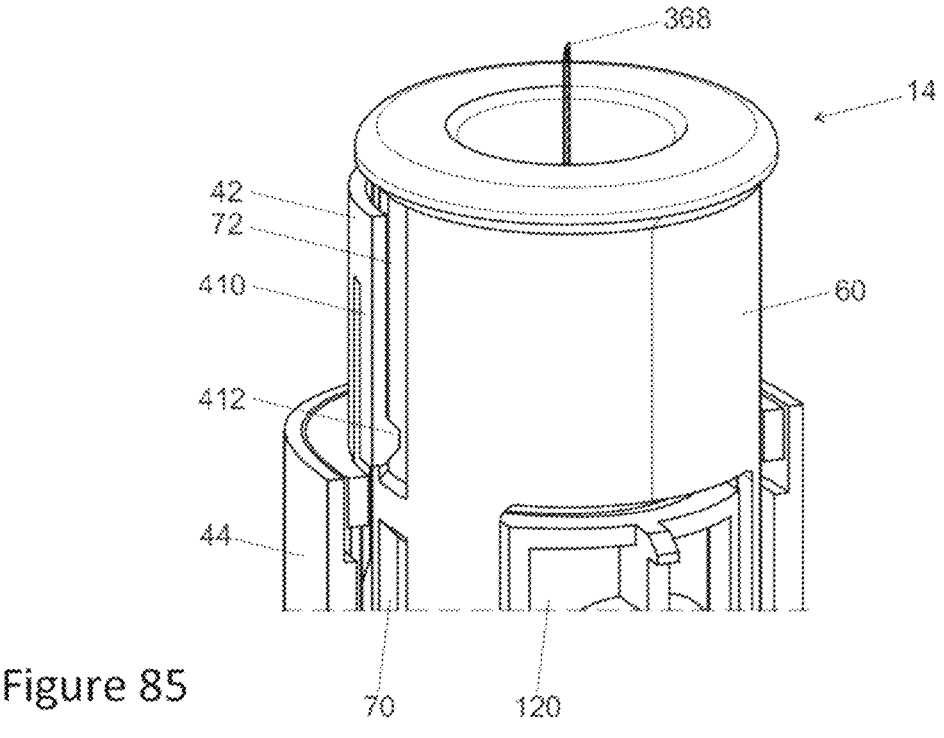
FIG. 85 shows a perspective view of the components in FIG. 84.

FIGS. 80 to 85 show the cap and the adjacent parts of the medicament delivery device for context. The focus here is on the lock mechanism provided by a combination of the cap 160, the needle guard 60 and the housing 40 (more specifically the proximal housing 42 in this particular case). In this case, the cap comprises two cap housings 162 as shown in FIG. 80, although the lock mechanism would also function if the cap were a single integral piece. Optionally, the cap housings 162 each comprise a flange 163, which extends out from the tubular shape of the cap and can provide something to help grip the cap during cap removal. The cap housings 162 can be attached to one another by a snap fit, although other attachment mechanisms such as glue are also possible. The rigid needle shield remover 180 is arranged between the cap housings 162. FIG. 81 shows the proximal housing 42, including an arm 410 and an optional cap guide 411 (in this case a rib extending in the axial direction); the cap guide can help align the cap relative to the proximal housing and/or help fix the cap relative to the proximal housing in the circumferential direction. FIGS. 82 and 83 show the part of the autoinjector containing the lock mechanism. The cap 160, the needle guard 60 and the housing 40 (particularly the proximal housing 42) are shown. For context, the primary package 360, the optional needle guard spring 140, and the syringe holder 120 are also visible, along with the distal housing 44.

The proximal housing 42 comprises an arm 410. The arm comprises a protrusion 412; the protrusion 412 extends towards the axis 20 in the radial direction. In this example, the arm extends in the axial direction 22, although it could also extend in another direction such as the circumferential direction 24. In this example, the arm is attached to the rest of the proximal housing at the proximal end of the arm, although the distal end of the arm could alternatively be attached to the proximal housing. The protrusion 412 extends into a cut-out (or alternatively a recess) 70 of the needle guard 60. The needle guard 60 also comprises an optional recess (or alternatively a cut-out) 72; this recess is arranged closer to the proximal end of the needle guard 60 than the cut-out 70, and can reduce the friction of the protrusion 412 of the arm 410 of the proximal housing against the needle guard 60 during removal of the cap from the autoinjector and during subsequent use of the device.

On the opposite side of the arm 410 of the proximal housing 42 to the protrusion 412, the arm is adjacent to a surface of the cap (in this case part of a cap housing 162) which stops (or at least limits) the movement of the arm in the radial direction whilst the cap is attached to the autoinjector. As can be seen in FIG. 83, this restricts the movement of the needle guard 60 in the distal direction, as the protrusion 412 of the arm 410 of the proximal housing cannot move out of the way of the needle guard 60. This can stop premature autoinjector activation, for example if the autoinjector is dropped, as the movement of the needle guard 60 can be restricted so that it cannot move far enough in the distal direction to activate the device. Alternatively, the arm could be angled inwards (or biased inwards) so that the arm is in the way of the needle guard 60 rather than the protrusion, with the protrusion on the side of the arm facing away from the axis rather than on the side of the arm facing towards the axis. The protrusion could alternatively be provided by a wedge-shaped end to the arm, with the flexible end of the arm being wider in the radial direction than the attached end of the arm.

Once the cap has been removed from the autoinjector (either by twisting or pulling relative to the autoinjector), the needle guard 60 can move to its full extent in the distal direction (relative to the housing 42, 44), as the arm 410 of the proximal housing 42 is able to move in the radial direction to allow the needle guard 60 to move past the protrusion 412 in the distal direction. As the needle guard 60 moves in the distal direction, the protrusion 412 of the arm 410 of the proximal housing leaves the cut-out 70 of the needle guard 60 and subsequently enters the recess 72 of the needle guard 60. The resulting position of the needle guard 60 relative to the proximal housing 42 can be seen in FIGS. 84 and 85.

The cap and lock mechanism described above and with reference to FIGS. 80 to 85 are an example of a cap and a corresponding lock mechanism more generally, and this particular design can also be modified in various ways in addition to the options already mentioned above (with the example below in FIGS. 111 to 120 being just one alternative). A number of alternatives are possible along the lines outlined for the designs described above, particularly with reference to the cap and lock mechanism designs. For example, instead of the needle guard 60 being closest to the axis as shown in FIG. 82, with the cap 160 furthest from the axis and the housing (arm 410 of the proximal housing 42 in this case) in between the needle guard and the cap, the lock mechanism can effectively be reversed, with the cap (or at least a portion of the cap) closest to the axis, the needle guard furthest from the axis, and the proximal housing (such as an arm) in between. The cap described above comprises three parts, but a cap consisting of another number of parts or even a single integral part could be used instead.

Figures 86, 87:
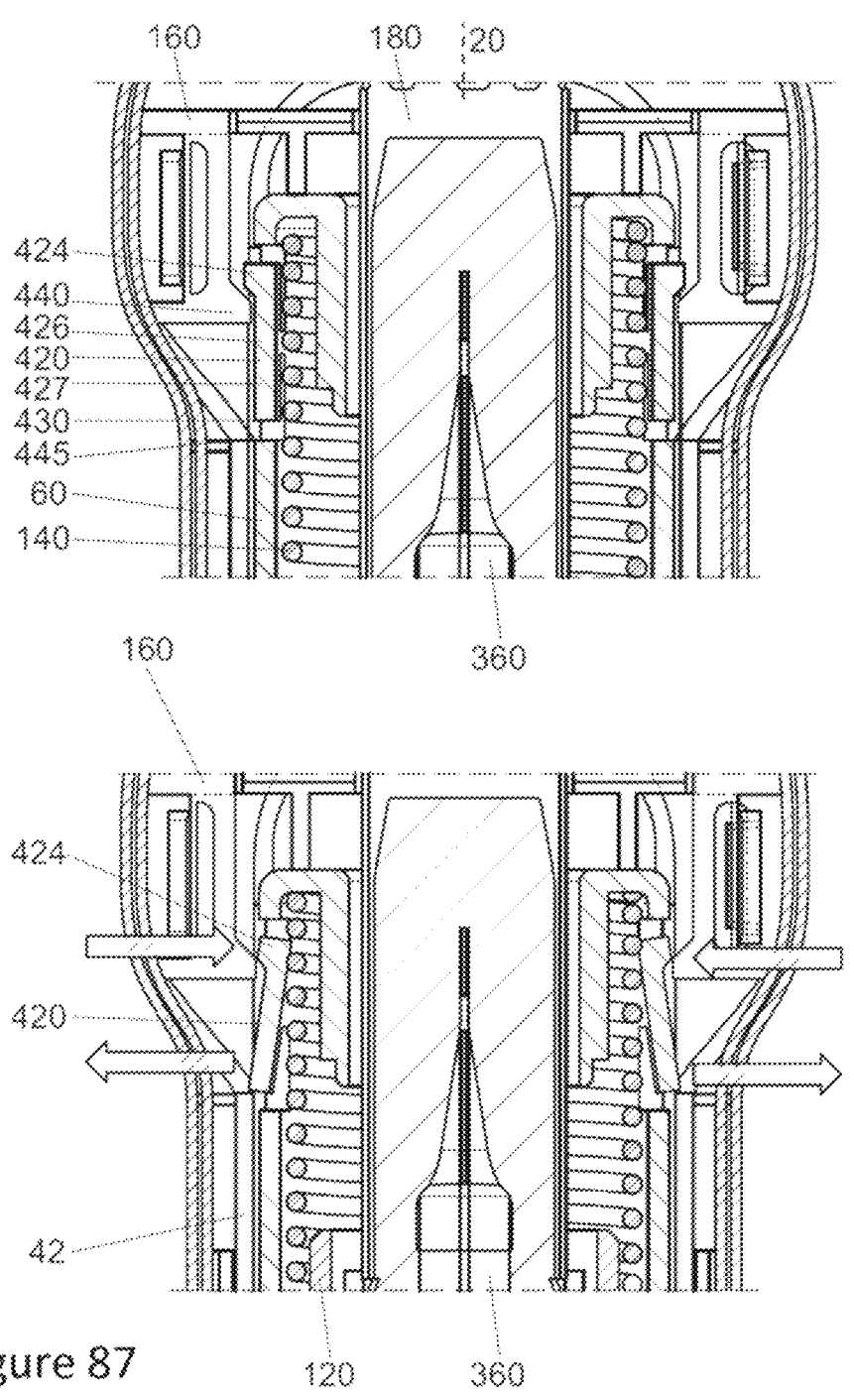
FIG. 86 shows a cross-section view of part of another example autoinjector.
FIG. 87 shows a cross-section view of the autoinjector of FIG. 86 when the needle guard moves in the distal direction relative to the housing prior to removal of the cap.

A third alternative lock mechanism will now be described with reference to FIGS. 86 to 88. The general design of the autoinjector here could be based on one of the autoinjectors described herein, so will not be described in detail. The general design of the cap in particular could also be based on the designs of other caps described herein and will also not be described again in detail—the cap shape shown in FIGS. 86 and 87 is similar to that shown in FIG. 80, although other shapes could also be used.

Once again, the focus here is on the lock mechanism provided by a combination of the cap 160, the needle guard 60 and the housing 40 (more specifically the proximal housing 42 in this particular case). For context, the primary package 360, the optional needle guard spring 140, and the syringe holder 120 are also visible (see FIG. 87 in particular).

In this alternative lock mechanism, the needle guard 60 comprises a double-ended arm 420 (which could alternatively be called a rocker or a seesaw). The double-ended arm 420 of the needle guard 60 extends from a proximal part 426 to a distal part 427. As can be seen in FIG. 88, the double-ended arm 420 is attached to the rest of the needle guard 60 by a rocker bar 422, around which the double-ended arm 420 can pivot. A protrusion 424 extends away from the axis from the proximal end of the double-ended arm 420 (although the protrusion 424 could alternatively extend towards the axis in a lock mechanism design where the portion of the cap that provides the lock mechanism is closer to the axis than the portion of the needle guard that provides the lock mechanism-effectively inverting the lock mechanism, in the same way as already described in more detail for other lock mechanisms above).

The cap comprises a protrusion 440 (for example attached to a cap housing 162). The protrusion 440 extends towards the axis. The protrusion 440 is further from the proximal end of the autoinjector than the protrusion 424 is from the proximal end of the autoinjector. The protrusion 424 comprises an angled surface that faces at an angle to the radial direction 26 and to the axial direction 22, with the surface facing away from the proximal end and away from the axis. The protrusion 440 preferably comprises a surface that faces the angled surface of the protrusion 424. The resulting angled surfaces on the protrusions 424, 440 are not essential, but can reduce the friction resulting from contact of the protrusion 424 with the protrusion 440.

The distal end of the double-ended arm 420 comprises a distally facing surface 430. The housing (in this case the proximal housing 42) comprises a corresponding proximally facing surface 445 of the proximal housing 42. The proximally facing surface 445 of the proximal housing 42 is further from the proximal end of the autoinjector than the distally facing surface 430 of the distal part 427 of the double-ended arm is from the proximal end of the autoinjector. The proximally facing surface 445 of the proximal housing 42 is further from the axis than the distally facing surface 430 of the distal part 427 of the double-ended arm is from the axis.

When the cap is still on the autoinjector, as shown in FIGS. 86 and 87, the lock mechanism restricts the distal movement of the needle guard 60 relative to the housing. If the needle guard 60 moves in the distal direction relative to the housing (as shown in FIG. 87), the protrusion 424 of the double-ended arm 420 of the needle guard is pushed against the protrusion 440 of the cap 160. As a result, the protrusion 424 is pushed towards the axis, which pivots the double-ended arm 420 about the rocker bar 422, resulting in the proximal part 426 of the double-ended arm moving towards the axis and the distal part 427 of the double-ended arm moving away from the axis. As a result, the distally facing surface 430 of the distal part of the double-ended arm is moved away from the axis, aligning it with the proximally facing surface 445 of the proximal housing 42, as shown in FIG. 88. The alignment of the distally facing surface 430 of the distal part of the double-ended arm and the proximally facing surface 445 of the proximal housing 42 stops the needle guard 60 from moving further in the distal direction relative to the housing.

When the cap is removed from the autoinjector, the double-ended arm 420 pivots to allow the protrusion 440 of the cap 160 to pass the protrusion 424 of the double-ended arm. Once the protrusion 440 has passed the protrusion 424, the double-ended arm 420 of the needle guard 60 pivots back into place, allowing the needle guard 60 to move in the distal direction relative to the proximal housing 42 without the distally facing surface 430 of the distal part of the double-ended arm being moved away from the axis, with the result that the distally facing surface 430 can move into the proximal housing 42 without engaging the proximally facing surface 445 of the proximal housing 42.

FIGS. 89 and 90 show another alternative cap design which could be used with medicament delivery devices, for example with the autoinjectors described herein. FIG. 89 shows the cap 160 in an autoinjector, the autoinjector comprising a housing 40 with an optional window 46, a needle guard 60 and the cap 160. The cap 160 is inside the needle guard 60. FIG. 90 shows the cap 160, which comprises a cap housing 162, a pull strap 176 and an arm 177

(two arms in this example); the arm 177 comprises an optional protrusion 179. The pull strap can be provided to allow a user to remove the cap; another type of cap removal portion such as a handle could alternatively be provided. The arm 177 extends from the cap housing 162. As shown in FIG. 89, the arm (in this case the protrusion 179 of the arm 177) extends into a cut-out in the needle guard 60, holding the cap in place in the needle guard 60. The arm 177 is flexible, allowing the protrusion to move towards the axis and past the needle guard 60 during removal of the cap from the needle guard. After the cap has been removed, the arm 177 will flex back out again, making it difficult for the cap to be put back on the device as the arm extends away from the axis too far to fit back into the needle guard. This can be advantageous, as it can stop a cap from being replaced on an activated or used device. Two arms are shown in this example; just one arm could be provided. Three or more arms could also be provided; this could be beneficial as it could make it even harder to put the cap back on (for example, more arms could make it harder to push all the arms back towards the axis whilst simultaneously pushing the cap back into the needle guard).

Figures 91, 92, 93:
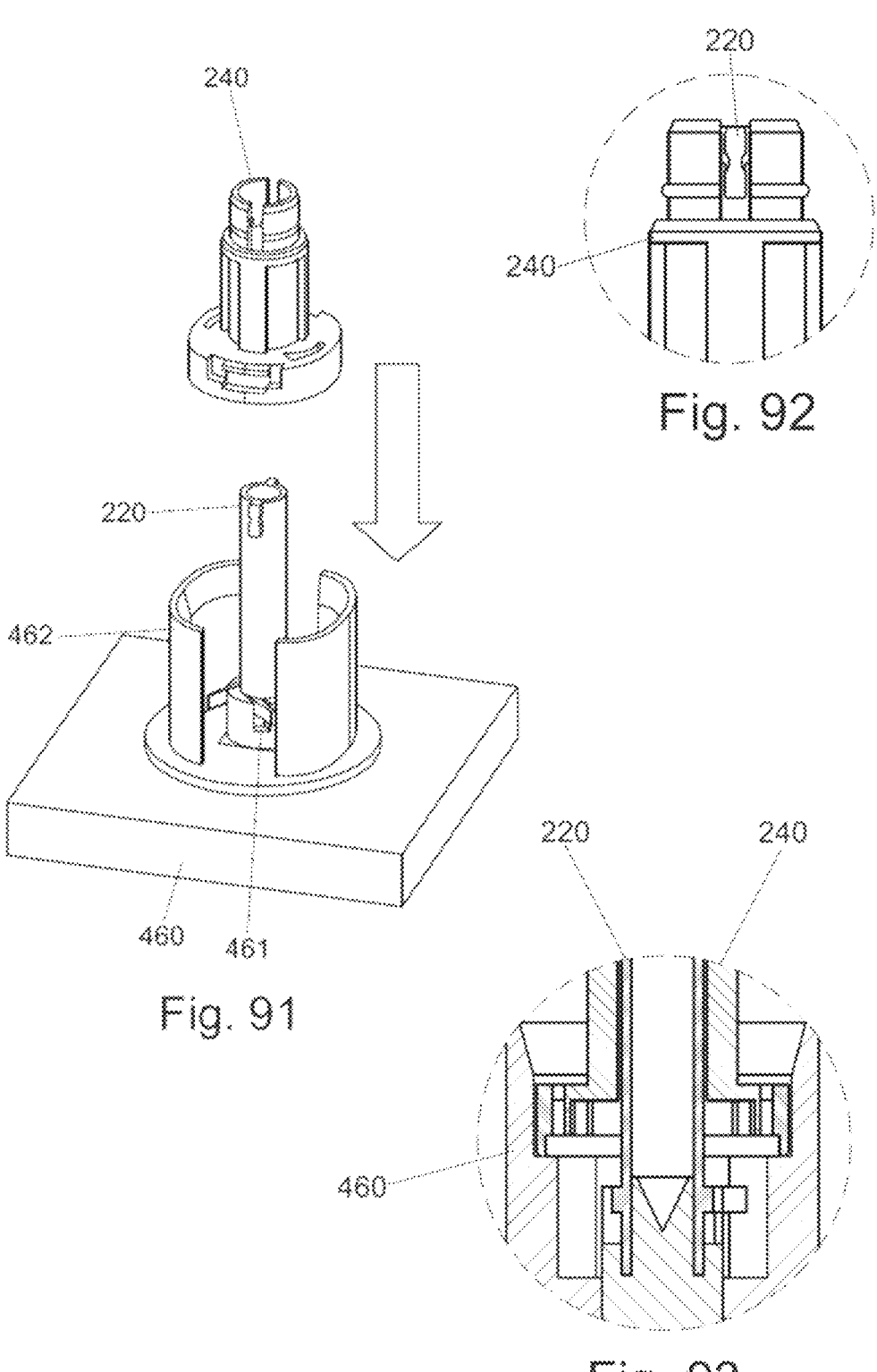
FIG. 91 shows a perspective view of a distal end tool, a powerpack lock and a powerpack housing during device assembly.
FIG. 92 shows a side view of part of the powerpack lock and the powerpack housing during device assembly.
FIG. 93 shows a cross-section side view of part of the distal end tool, the powerpack lock and the powerpack housing during device assembly.
Figures 94, 95, 96, 97, 98:
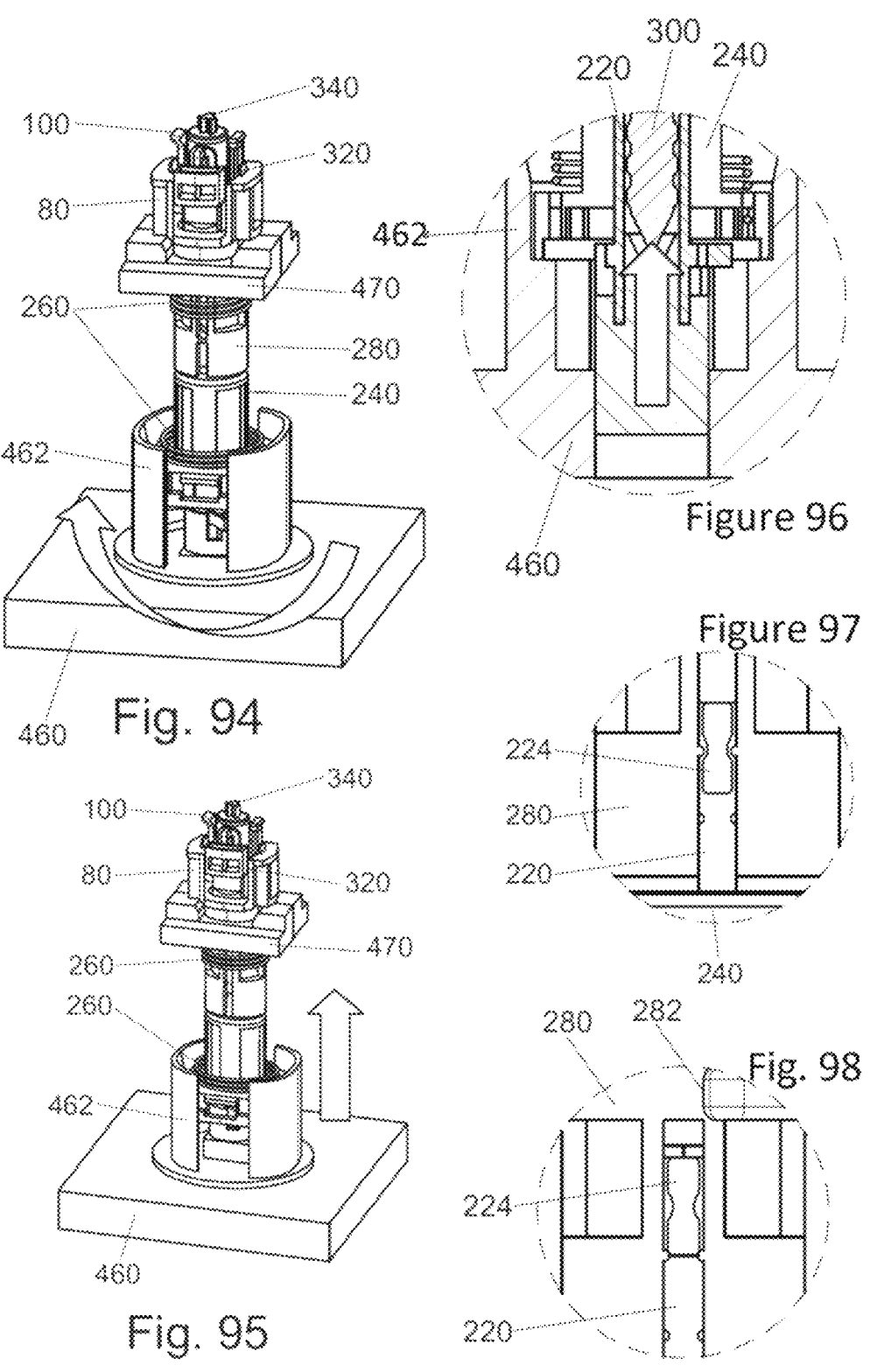
FIGS. 94 and 95 show a perspective view of the distal end tool, a proximal end tool and part of the autoinjector during device assembly.
FIGS. 96, 97 and 98 show cross-section side views of parts of the autoinjector and assembly tools during device assembly.

In the description above referring to FIGS. 15 to 19, assembly of the powerpack was discussed. FIGS. 91 to 98 similarly show powerpack assembly, and a full explanation of the functionality as described above will not be repeated-FIGS. 91 to 98 show slightly differently shaped components, but the process is broadly the same, with the powerpack moving from a first position (winding up position) to a second position (powerpack lock position) to a third position (powerpack unlocked position). In addition to the autoinjector components, FIGS. 91, 94 and 95 show tooling parts that could be used to assist assembly. As a general introduction to the concept—it has been appreciated that, whilst torsion springs typically provide a cost-effective rotational energy source, they also result in the challenge that the diameter of the spring reduces when the spring is wound up.

As can be seen in FIGS. 94 and 95 in particular, the tool used to assist assembly (spring winding tool) comprises two parts that can rotate relative to one another, namely a distal end tool 460 and a proximal end tool 470. The distal end tool 460 is configured to receive and rotationally lock the powerpack lock 220 so that the powerpack lock 220 cannot rotate relative to the distal end tool 460. In this example, this is achieved by the provision of grooves 461 that receive the protrusions 226 of the powerpack lock 220, as shown in FIG. 91. Optionally, the distal end tool 460 comprises a support portion 462 (in this case a tubular portion) to help support the powerpack housing 240—this can also rotationally lock the powerpack housing 240 relative to the distal end tool 460 as well if desired for extra stability. The proximal end tool 470 is configured to receive and rotationally lock a component that is rotationally locked to the proximal end of the torsion spring 260—this could be various components, for example a component from the activation sub-assembly 56. In the example shown (see e.g. FIG. 94), the proximal end tool 470 is configured to receive and rotationally lock to the lock activation sleeve 80. The particular shapes of the distal end tool 460 and the proximal end tool 470 could vary widely depending on the shape of the relevant autoinjector components and on the shape of other tools being used to assist autoinjector assembly.

The method of use of the spring winding tool (comprising the distal end tool 460 and proximal end tool 470) will now be described. As shown in FIG. 91, the powerpack lock 220 is first inserted into the distal end tool 460, followed by attachment of the powerpack housing 240 to the powerpack lock 220. At this point, the powerpack lock 220 and the powerpack housing 240 are attached to one another by the protrusion 224 of the powerpack lock 220 and the corresponding recesses in the powerpack housing 240 as described above with reference to FIG. 16 and as shown in FIG. 92. The position of the distal end tool 460 relative to the powerpack lock 220 and the powerpack housing 240 is shown in FIG. 93.

Next, a torsion spring 260, a driver 280, an activation sub-assembly (in this particular example comprising a lock activation sleeve 80, a needle guard lock 100, a driver nut 320 and a thrust bearing 340, along with a plunger rod (not shown), and the proximal end tool 470 are added to the powerpack housing 240, as shown in FIG. 94. The proximal end tool 470 can then be rotated relative to the distal end tool 460 to wind the torsion spring 260—at this point, the driver is free to rotate relative to the powerpack lock. The rotation step can optionally be carried out in two steps, with the first step being a limited rotation (for example rotating the distal end tool 460 relative to the proximal end tool 470 by a quarter turn or a half turn (i.e. 90 or 180 degrees) to engage the proximal end protrusion 262 of the spring 260 with the circumferentially facing ledge 282, which allows for a check of whether the spring and driver are engaged correctly, followed by rotation of the distal end tool 460 relative to the proximal end tool 470 to wind the torsion spring 260 to the desired amount). It is noted that FIGS. 94 and 95 again show only parts of the torsion spring 260, with a short section of unwound spring and a short section of wound spring shown for context (the wound spring has a smaller diameter than the unwound spring).

Once the torsion spring 260 is wound up, the powerpack lock 220 is moved into the second position as shown in FIGS. 95 to 97 (FIG. 97 is equivalent to FIG. 19 in the description above). This can be achieved by moving the distal end tool 460 towards the proximal end tool 470. This locks the powerpack by rotationally locking the powerpack lock and driver as described above, so that the torque from the spring cannot be released, due to the driver and the powerpack housing being rotationally locked to one another via the powerpack lock. The resulting sub-assembly can then be removed from the tool and inserted into the housing 40, which rotationally locks the activation sub-assembly and the powerpack housing relative to the housing. At this point, the powerpack lock 220 can be moved to the third position, as shown in FIG. 98.

In general, this type of solution, where the spring is wound up before assembly is complete, can be beneficial as it can allow for a smaller diameter enclosure for the spring than would be otherwise necessary-winding up the spring first reduces the size of the spring. The tool described above can allow the spring to be wound up externally and subsequently transferred into the housing. This can allow the inner diameter of the housing (or at least the inner diameter of an entry point into the housing) to be smaller than the diameter of the unwound spring.

Figure 99:
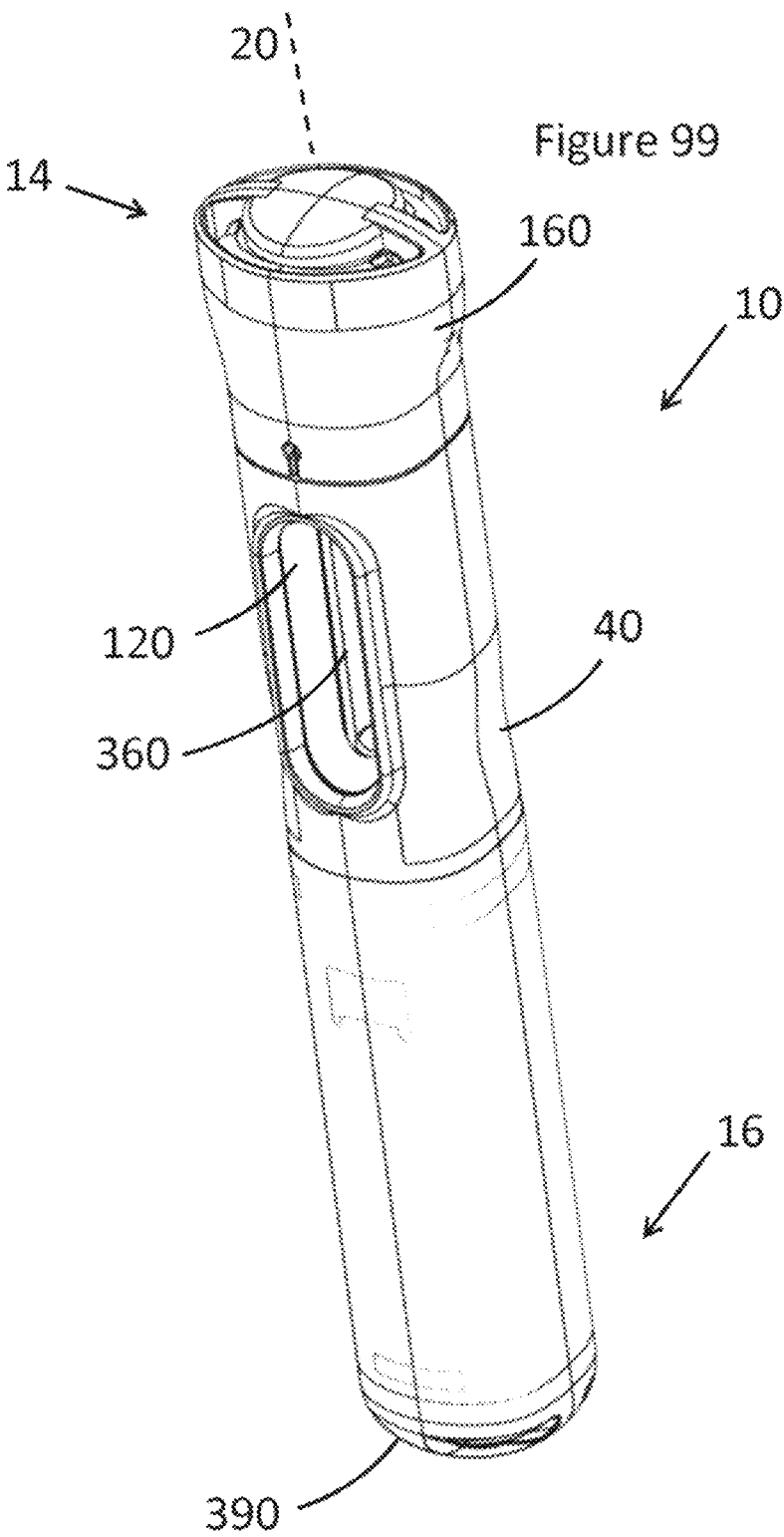
FIG. 99 shows a perspective view of another example autoinjector.

FIG. 99 shows another autoinjector 10 with a similar assembly to those described above. In FIG. 99, a housing 40, a cap 160, and an optional spinner cap 390 can be seen, along with small portions of a syringe holder 120 and a primary package 360. One visible difference compared to the previous designs is the design of the cap 160, which will be described in more detail below.

Figure 100:
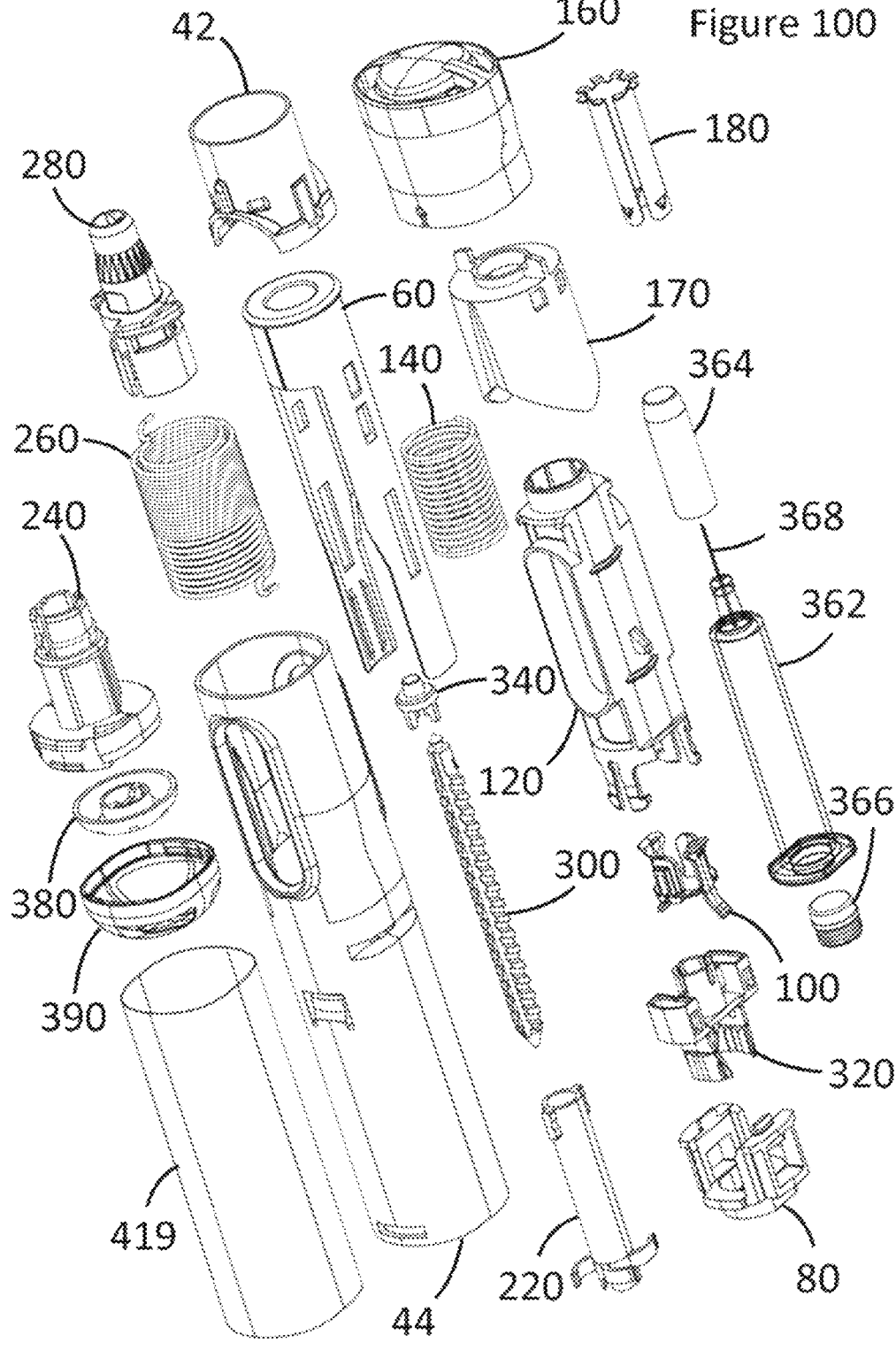
FIG. 100 shows an exploded perspective view of the autoinjector of FIG. 99.

FIG. 100 shows the parts of the autoinjector 10 of FIG. 99 disassembled, namely housing (split into a proximal housing 42 and a distal housing 44), a needle guard 60, a lock activation sleeve 80, a needle guard lock 100, the syringe holder 120, a needle guard spring 140, a cap housing 162, a cap insert 170, an optional spinner 380 and the spinner cap 390, a powerpack lock 220, a powerpack housing 240, a torsion spring 260 (in FIG. 100, the torsion spring is shown fully, in both the tensioned and untensioned state, to show the difference in diameter between the tensioned and untensioned states), a driver 280, a plunger rod 300, a driver nut 320, a thrust bearing 340, and the primary package (in this example comprising a syringe 362 with a needle 368, a rigid needle shield 364 and a stopper 366). An optional label 419 is again also shown.

Figures 101, 102, 103, 104:
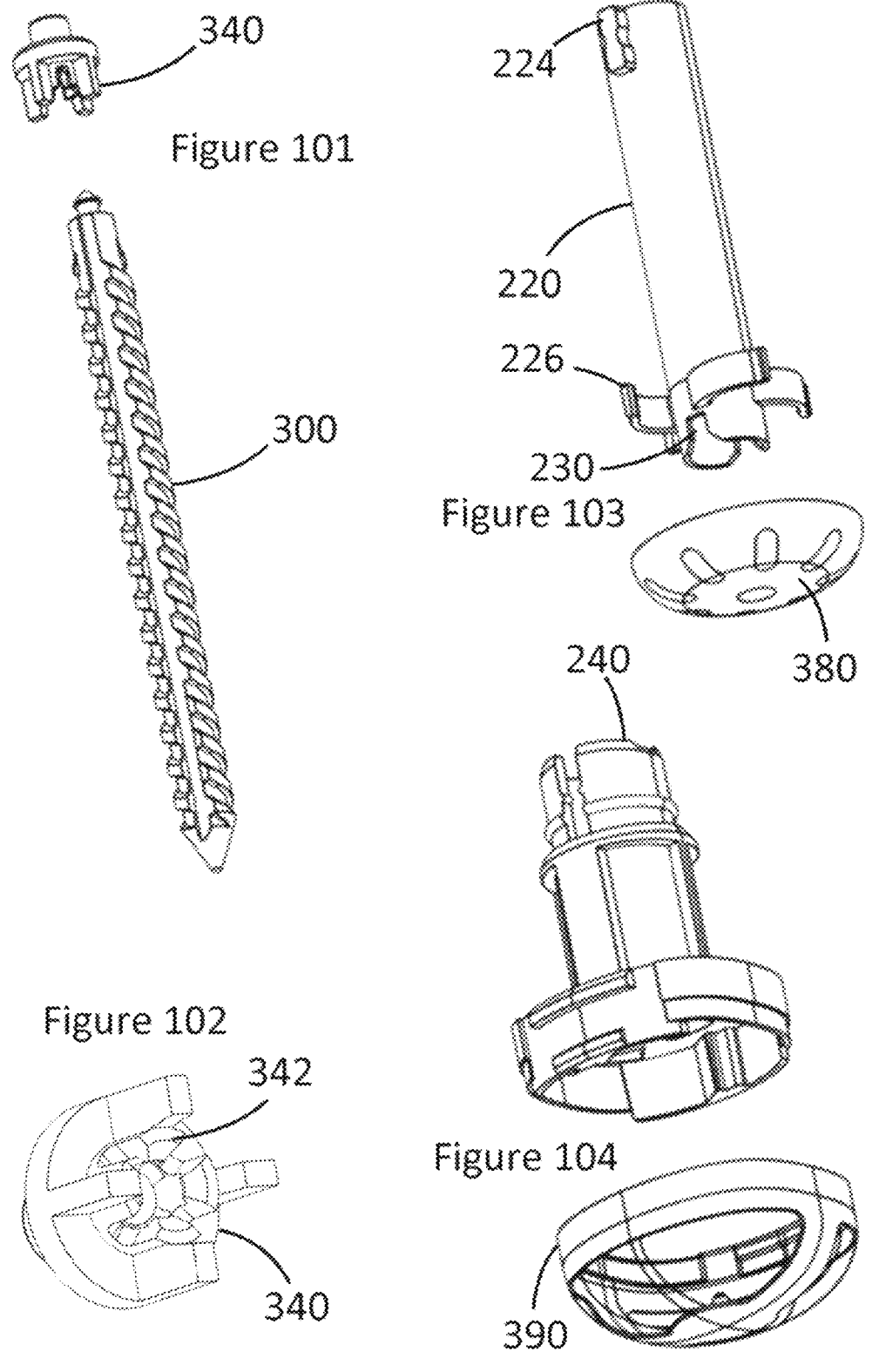
FIG. 101 shows a perspective view of the plunger rod and the thrust bearing of FIG. 100.
FIG. 102 shows another perspective view of the thrust bearing of FIG. 100.
FIG. 103 shows a perspective view of the powerpack lock and the driver of FIG. 100.
FIG. 104 shows a perspective view of the powerpack housing and the spinner cap of FIG. 100.
Figures 105, 106A, 106B, 107, 108:
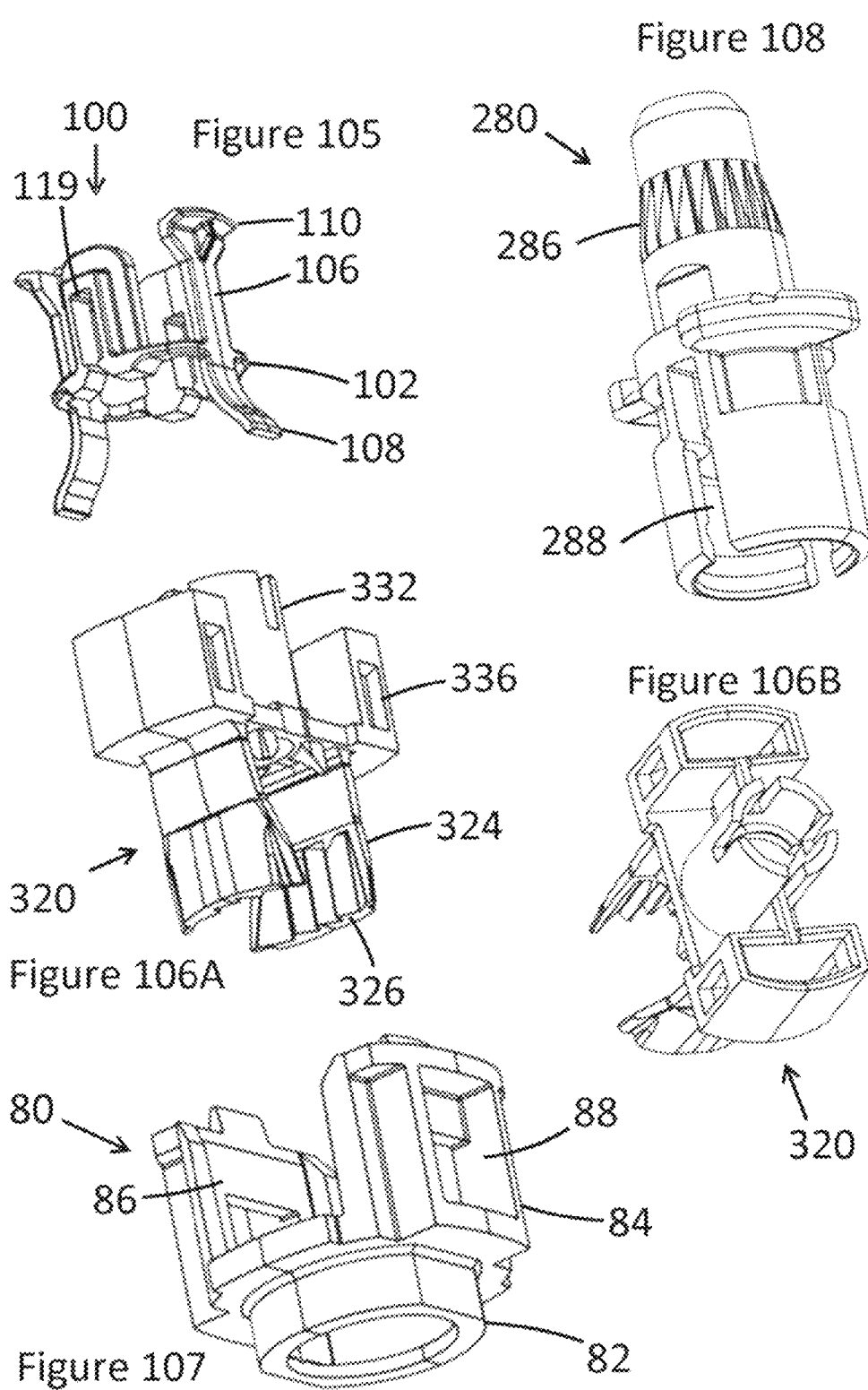
FIG. 105 shows a perspective view of the needle guard lock of FIG. 100.
FIGS. 106A and 106B show different perspective views of the driver nut of FIG. 100.
FIG. 107 shows a perspective view of the lock activation sleeve of FIG. 100.
FIG. 108 shows a perspective view of the driver of FIG. 100.
Figures 109, 110:
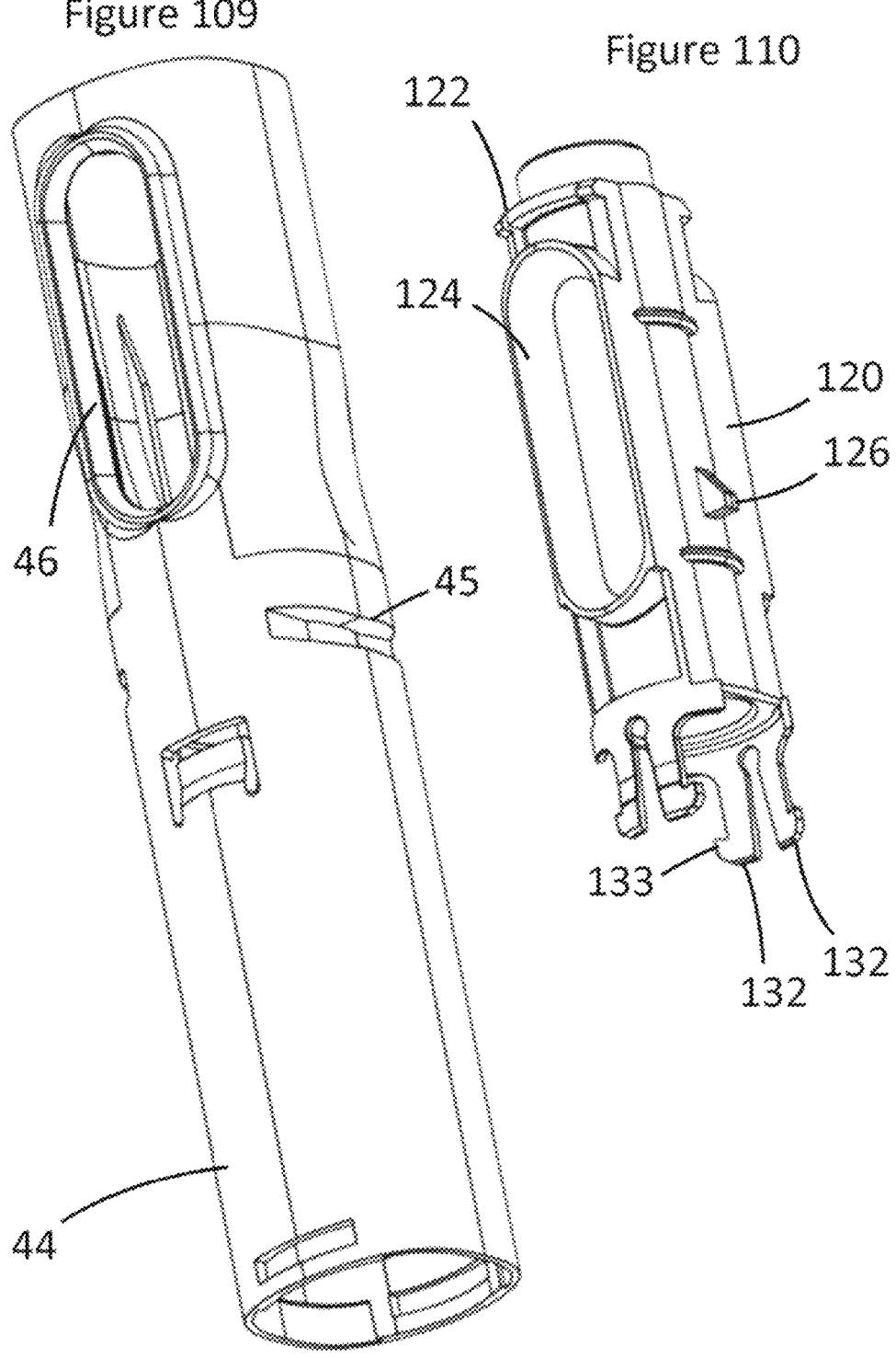
FIG. 109 shows a perspective view of the distal housing of FIG. 100.
FIG. 110 shows a perspective view of the syringe holder 120 of FIG. 100.

The parts are generally interchangeable between the devices described herein. Nevertheless, some of the components are somewhat different in shape to those described elsewhere herein. Some of the components are shown in more detail in FIGS. 101 to 115. FIG. 101 shows the plunger rod 300 and the thrust bearing 340, and FIG. 102 shows further detail of the thrust bearing 340, which has four snap fit arms 342 in this particular example, although other numbers of snap fit arms 342 could be provided, both in this example and the other thrust bearing examples described herein. FIG. 103 shows further detail of the powerpack lock 220 and the corresponding spinner 380. Further protrusions 226 can be seen (in this example four further protrusions), which in this example are curved in a plane perpendicular to the longitudinal axis, in contrast to the protrusions 226 shown in FIG. 73, for example, which are straight (and tapered in the particular example in FIG. 73 as well, though this is optional) in a plane perpendicular to the longitudinal axis. FIG. 104 shows further detail of the powerpack housing 240 and the corresponding spinner cap 390, which can be joined together by a snap fit. FIGS. 105, 106 and 107 show further detail of the needle guard lock 100, the driver nut 320 (with FIGS. 106A and 106B showing different angles) and the lock activation sleeve 80 respectively. FIG. 108 shows the driver 280. FIG. 109 shows the distal housing 44, which is part of the housing 40, and FIG. 110 shows the syringe holder 120; various features of the housing 40 and the syringe holder 120 are as described in other examples herein, and will not be repeated. A notable difference, however, lies in the optional attachment (a snap fit in these examples) between the syringe holder 120 and the driver nut 320, which was provided by a hook 128 of the syringe holder 120 (the hook extending in the radial direction (specifically away from the axis in the radial direction, though this could be reversed) and the hook 334 of the driver nut 320 in the example in FIG. 34. An alternative example is shown in FIG. 110 and FIG. 106 (FIG. 106B in particular), in which the snap fit snaps together by flexing in the circumferential direction rather than the radial direction, although these attachments are interchangeable in the examples described herein. In particular, two pairs of snap-fit arms 132 are provided on the syringe holder 120. Each pair of snap-fit arms comprises two arms 132, each of which comprises a protrusion 133 extending in the circumferential direction. The two protrusions 133 in a pair of snap-fit arms extend away from each other, as can be seen in FIG. 110, for example. The driver nut 320 comprises corresponding snap-fit holes 336 (or alternatively recesses) configured to receive the protrusions 133 to provide the snap-fit.

Figures 111, 112:
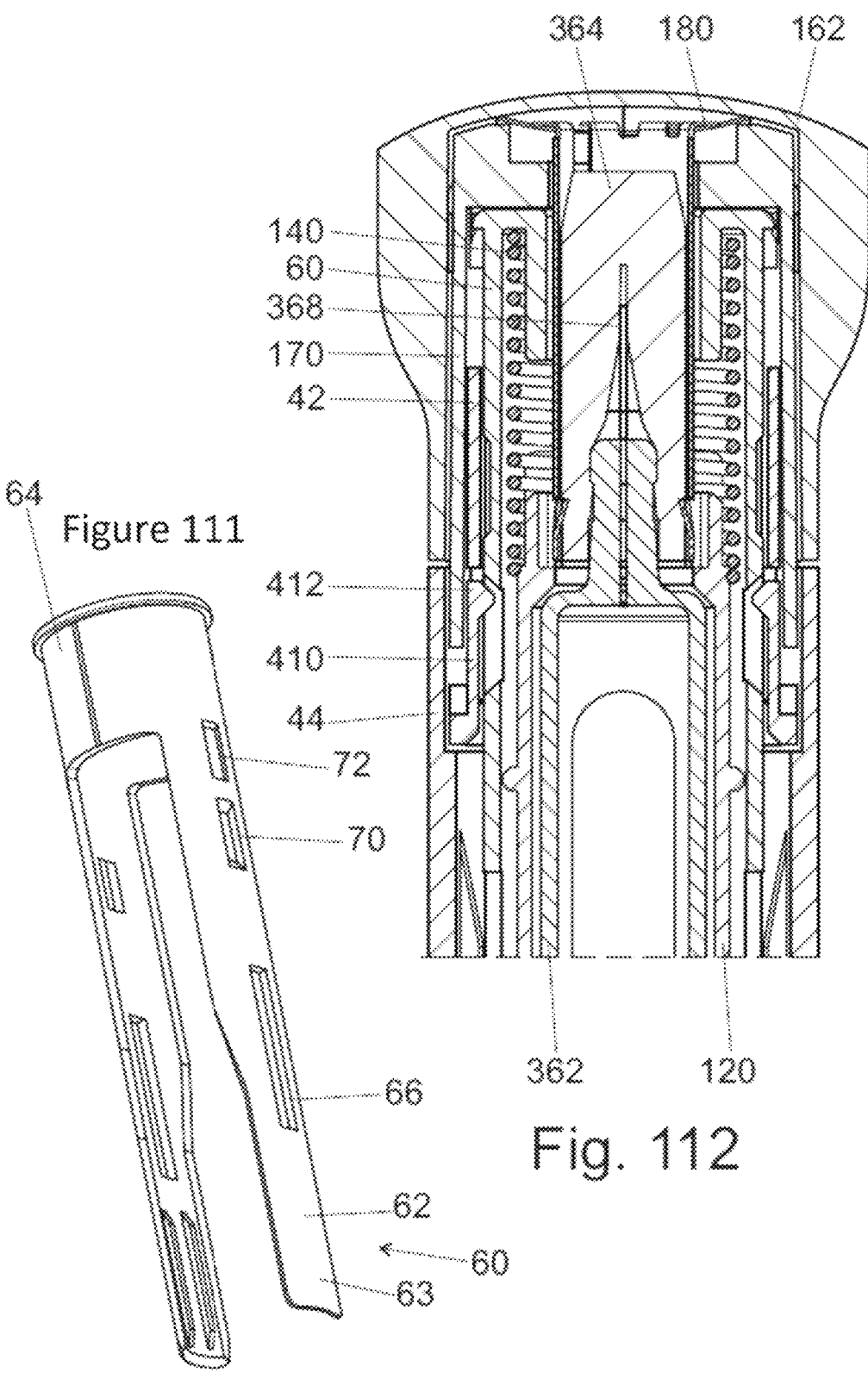
FIG. 111 shows a perspective view of the needle guard of FIG. 100.
FIG. 112 shows a cross-section view of part of the autoinjector of FIG. 99.
Figures 116, 117:
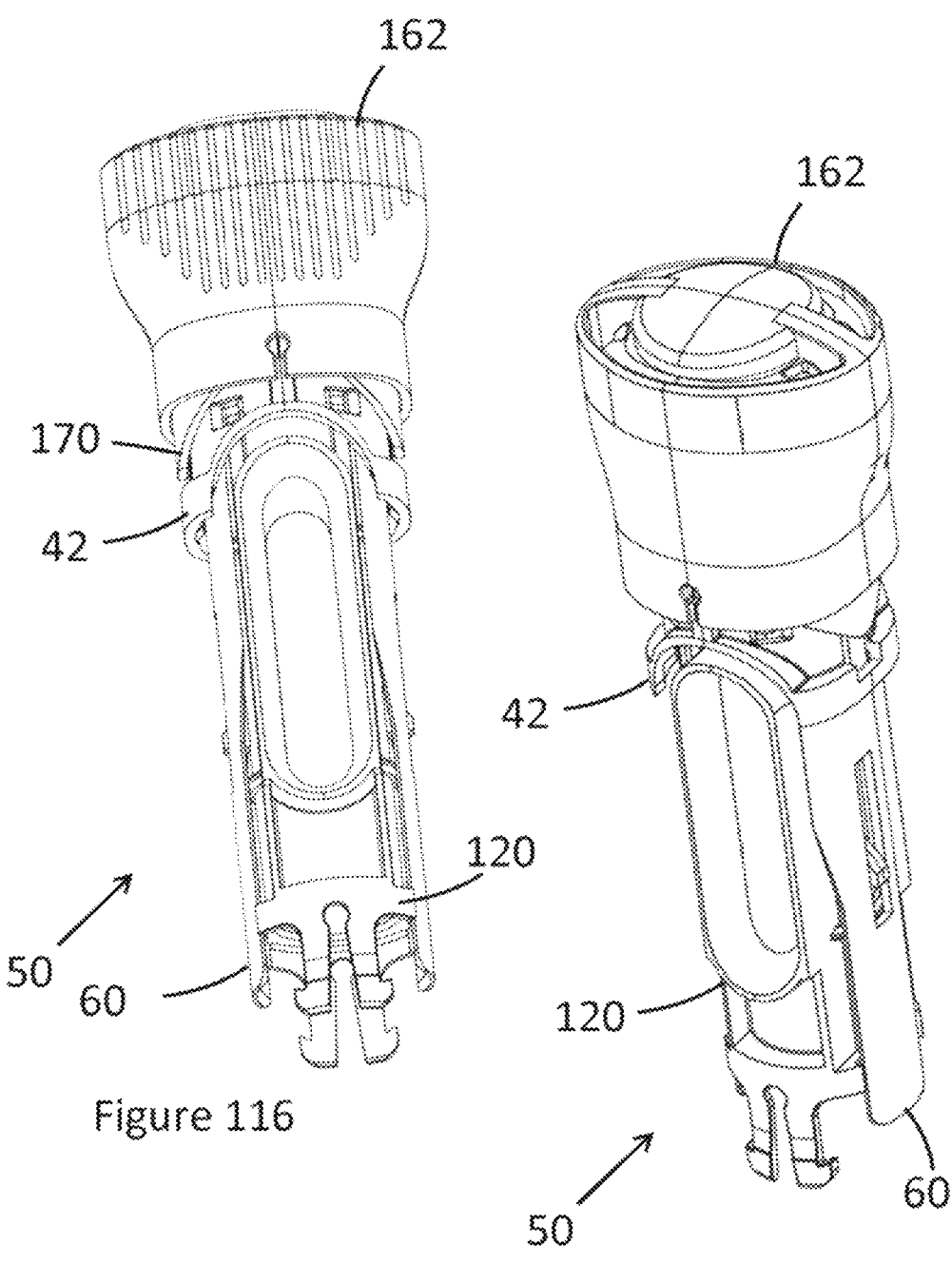
FIGS. 116 and 117 show different perspective views of the front sub-assembly of the autoinjector of FIG. 99.

FIGS. 111 to 120 will now be used to describe a front sub-assembly 50 of the example autoinjector in more detail. In this example, the front sub-assembly 50 comprises a syringe holder 120, a needle guard spring 140, a needle guard 60, a proximal housing 42 and also the three parts of the cap 160, namely a cap housing 162, a rigid needle shield remover 180 and a cap insert 170. FIGS. 111, 113, 114 and 115 show the needle guard 60, cap housing 162, cap insert 170 and proximal housing 42 respectively, and FIGS. 112, 116 and 117 show how the components fit together—in FIG. 112, the front sub-assembly 50 is shown in context alongside other parts of the example autoinjector, though the front sub-assembly could also be used with other autoinjectors. FIGS. 118, 119 and 120 show how the components fit together after the cap has been removed and the needle shield pushed in the distal direction.

Similarly to the example shown in FIGS. 80 to 85, a lock mechanism is provided by a combination of the cap 160, the needle guard 60 and the housing 40 (more specifically the proximal housing 42 in this particular case). Due to the functional similarity, a description of the components and functioning of the front sub-assembly of FIGS. 111 to 120 will not be repeated, and reference should be made to the explanation of the example in FIGS. 80 to 85.

One difference over the example in FIGS. 80 to 85 is that the arm 410 is attached to the rest of the proximal housing 42 at the distal end of the arm, although the proximal end of the arm could alternatively be attached to the proximal housing.

Another difference over the example in FIGS. 80 to 85 is that the proximal end of the distal housing 44 is closer to the proximal end of the front sub-assembly than the proximal end of the arm 410 (see FIGS. 118 to 120 for example). This can allow the arm 410 to be protected inside the distal housing 44 in a completed device; this can avoid user manipulation of the arm 410, which could otherwise result in interference by a user in the functioning of a completed device.

Another difference over the example in FIGS. 80 to 85 is the provision of surfaces that allow rotation of the cap 160 relative to the housing 40 to be translated into axial movement of the cap relative to the housing (a similar functionality is provided by the examples in FIGS. 10 and 67, for example). In this example, the cap insert 170 comprises a distal end surface 173 (rather than using the distal facing surface 169 of the cap housing 162, though the designs could be switched) which can interact with a corresponding proximally facing surface 49 of the housing 40 (the proximally facing surface 49 is provided by a rib on the proximal housing 42 in this particular example). The alternatives described with reference to the other examples herein (for example in FIGS. 10 and 67) could also be implemented for this example.

The cap housing 162 and the cap insert 170 are rotationally fixed (or at least limited in their rotation) relative to one another, in this example by a protrusion 175 of the cap insert 170 (in this example, the protrusion 175 extends from a proximal face of the cap insert) engaging with a slot 165 of the cap housing 162. Protrusions 159 of the cap housing 162 and cut-outs 178 (or recesses) of the cap insert 170 are also provided to attach the cap housing 162 to the cap insert 170 (with the rigid needle shield remover 180 arranged between the cap insert 170 and the cap housing 162 as explained previously), although the cut-outs could be on the cap housing instead with the protrusions on the cap insert. The protrusions 159 and the cut-outs 178 can also help limit or stop rotational movement of the cap housing relative to the cap insert.

FIGS. 121 to 128 will now be used to describe another approach to providing feedback that could be implemented instead of or additionally to the other feedback options provided herein. As such, this feedback mechanism could be implemented in a number of the devices described herein, such as the device in FIG. 100. More generally, feedback mechanisms of this type could also be used in medicament delivery devices where two components rotate relative to each other.

Figures 121, 122:
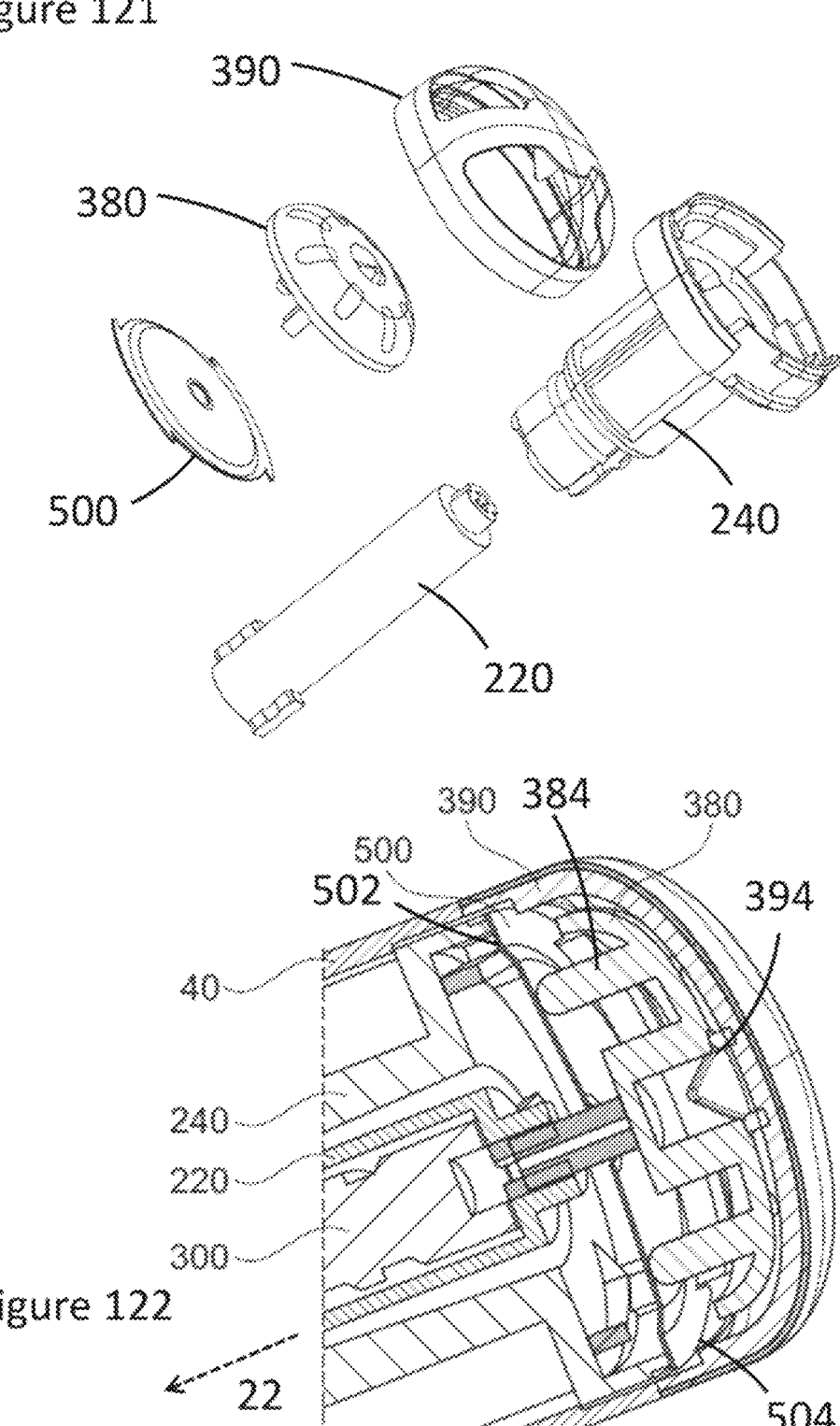
FIG. 121 shows an exploded perspective view of a feedback mechanism sub-assembly.
FIG. 122 shows a cross-section perspective view of part of a medicament delivery device that includes the feedback mechanism sub-assembly of FIG. 121.
Figures 123, 124, 125, 126A, 126B:
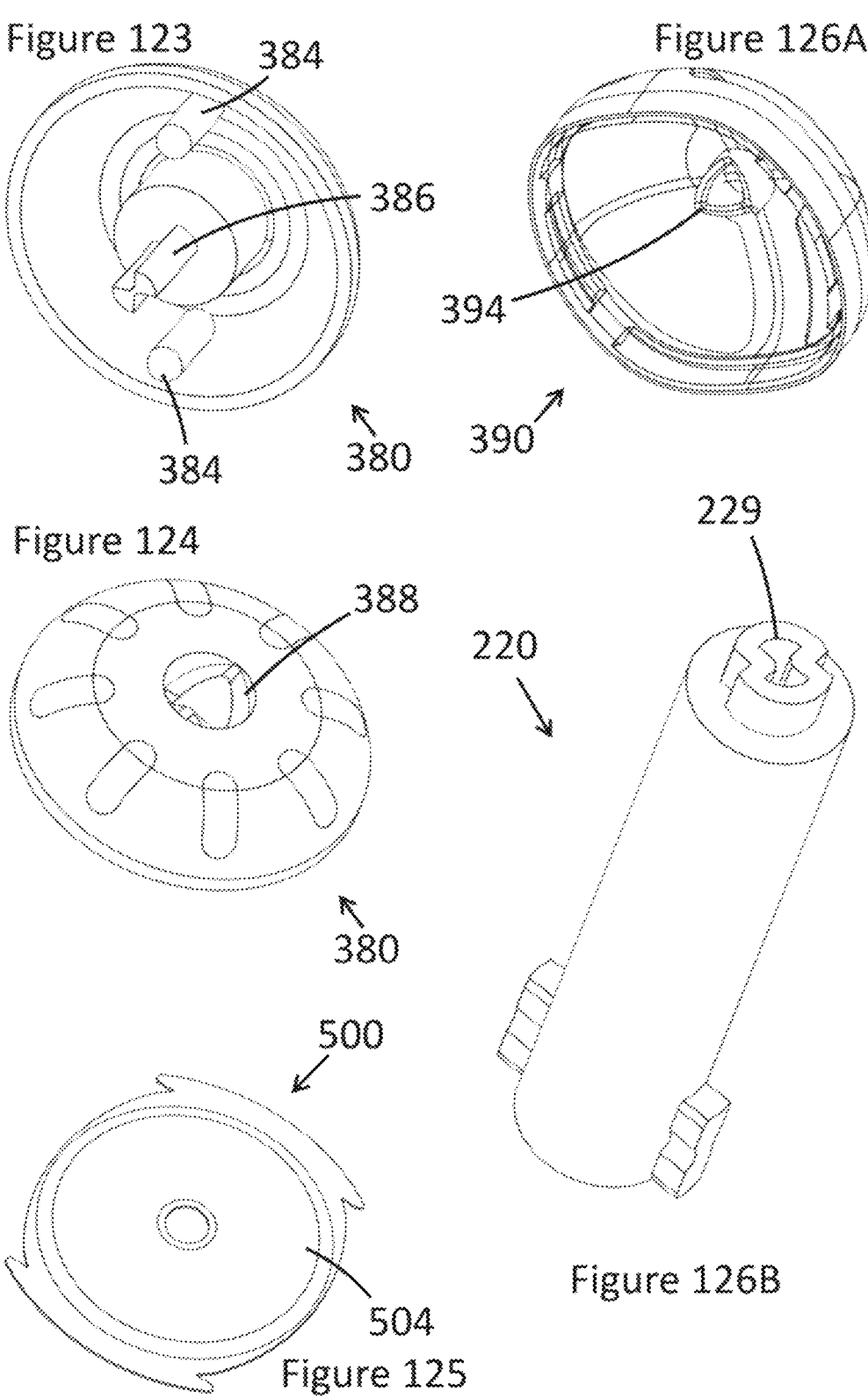
FIGS. 123 and 124 show perspective views of the spinner of FIG. 121.
FIG. 125 shows a perspective view of the clicker of FIG. 121.
FIG. 126A shows a perspective view of the spinner cap of FIG. 121.
FIG. 126B shows a perspective view of the powerpack lock of FIG. 121.

The feedback mechanism sub-assembly as shown in FIG. 121 comprises a powerpack lock 220, a powerpack housing 240, a spinner 380, a spinner cap 390 and a clicker 500. FIG. 122 shows how the components of the feedback mechanism sub-assembly fit together, with a housing 40 and a plunger rod 300 also shown for reference.

At the distal end of the device, the spinner cap 390 extends around the spinner 380 as can be seen in FIG. 122. The spinner 380 and the spinner cap 390 interact via a combination of a follower structure 388 and a guide structure 394 (which could be considered to be a cam follower and a cam), which will be described in more detail below.

The spinner 380 is arranged between the spinner cap 390 and the clicker 500. The spinner 380 comprises a pair of protrusions 384 which interact with the clicker 500; this will also be described in more detail below.

The clicker 500 is arranged between the powerpack housing 240 and the spinner 380. A proximally facing surface 502 of the clicker 500 abuts a distally facing surface of the powerpack housing 240, and a distally facing surface 504 of the clicker 500 abuts a proximally facing surface of the spinner 380 (which is the proximal end of the protrusion 384 in this example).

The spinner 380 is attached to a part of a medicament delivery device which rotates relative to the spinner cap 390, which in this case is the powerpack lock 220.

A housing 40, which would typically be immovably attached to the powerpack housing 240 and the spinner cap 390, is also shown for context. The powerpack housing 240 and the spinner cap 390 can be considered to be a part of the housing.

Figures 127, 128:
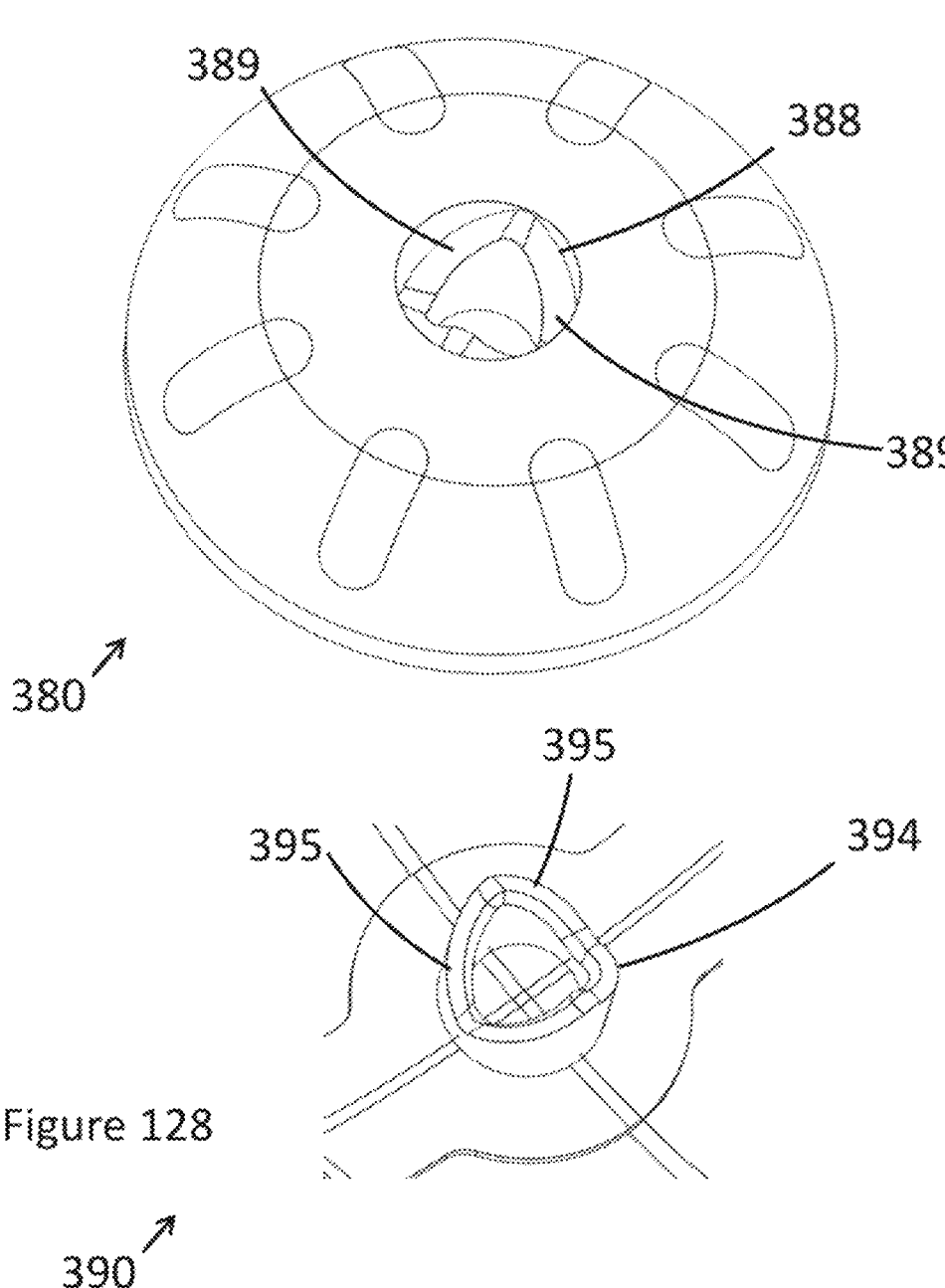

The connection between the spinner cap and the spinner will now be described in more detail with reference to FIGS. 127 and 128. In general, the idea is that the spinner cap (or more generally a housing) comprises a guide structure 394 and the spinner comprises a follower structure 388. This can transfer a rotational motion into a linear motion. As a result, when the spinner rotates relative to the housing (as described in more detail below), the interaction between the cam and the cam follower results in linear motion of the spinner relative to the housing. Numerous guide structure and follower structures could be used to achieve this, but the particular shape shown in the Figures will initially be described in more detail as an example. As can be seen in FIG. 127, the follower structure 388 of the spinner 380 comprises four sloped surfaces 389. Each of the sloped surfaces extends 90 degrees around the axis. Each of the sloped surfaces is sloped relative to a plane perpendicular to the axis. As a result, each sloped surface extends from a proximal end to a distal end. The proximal end of each sloped surface is adjacent to a proximal end of an adjacent sloped surface. The distal end of each sloped surface is adjacent to a distal end of an adjacent sloped surface. This results in the follower structure providing a surface that extends 360 degrees around the axis.

The guide structure 394 mirrors the follower structure in its design, with four sloped surfaces 395 in the same arrangement as in the guide structure. That is, each of the sloped surfaces extends 90 degrees around the axis. Each of the sloped surfaces is sloped relative to a plane perpendicular to the axis. As a result, each sloped surface extends from a proximal end to a distal end. The proximal end of each sloped surface is adjacent to a proximal end of an adjacent sloped surface. The distal end of each sloped surface is adjacent to a distal end of an adjacent sloped surface. This results in the follower structure providing a surface that extends 360 degrees around the axis.

It is optional that the follower structure and guide structure mirror one another in their design. For example, with the follower structure as shown in FIG. 127, part or all of the guide structure could simply be a protrusion extending in the axial direction, with the distal end of the protrusion abutting the surface of the follower structure. Alternatively, the guide structure could be as shown in FIG. 128, with part or all of the follower structure of FIG. 127 replaced with a protrusion.

Another alternative would be to provide a single sloped surface 389 rather than four sloped surfaces. If the guide structure 394 were replaced with a protrusion as described above, the single sloped surface could extend 90 degrees around the axis as shown in FIG. 127, or could alternatively extend less or further around the axis, for example 180, 270 or 360 degrees. In this example, when the protrusion passes the distal-most end of the sloped surface 389, the spinner would be abruptly pushed back in the distal direction relative to the spinner cap by the clicker. This abrupt movement could be beneficial as it could provide a louder click. This abrupt movement could also provide tactile feedback due to the sudden movement of parts relative to each other.

The interaction between the spinner 380 and the clicker 500 will now be described. The two protrusions 384 (e.g. FIG. 123) abut a distally facing surface 504 of the clicker. The clicker is a plate, and the plate is slightly deformed so that, when the spinner is in a distal position, the distally facing surface 504 of the clicker is convex (i.e. the centre of the distally facing surface 504 is further from the proximal end of the device than the edges of the distally facing surface 504). As a result, the proximally facing surface 502 is concave. When the spinner moves in the proximal direction, the powerpack lock 220 limits movement in the proximal direction of the of the outer edge (i.e. the edge furthest from the centre) of the clicker, whereas the rest of the clicker is pushed in the proximal direction by the protrusions of the spinner pushing in the proximal direction. As a result, the clicker is deformed and switches from a first shape to a second shape, with the distally facing surface 504 switching from a convex shape to a concave shape (and therefore the proximally facing surface 502 switching from a concave shape to a convex shape).

During use of a device containing the feedback mechanism sub-assembly as shown in FIG. 121, activation of the device would result in the rotation of the powerpack lock 220 relative to the housing 40 (typically at the same time as medicament delivery from the device). As the spinner 380 is rotationally locked to the powerpack lock 220, and the housing 40 is immovably attached to the powerpack housing 240 and the spinner cap 390, the spinner 380 rotates relative to the spinner cap 390. As a result, the follower structure of the spinner rotates relative to the guide structure of the spinner cap. Due to the respective shapes of the follower structure and the guide structure, this rotation pushes the spinner along the longitudinal axis relative to the spinner cap (i.e. in the axial direction 22, so in the proximal direction towards the proximal end of the device). In the particular design shown in the Figures, 90 degrees of rotation would result in movement of the spinner from its distal-most position to its proximal-most position. As the spinner moves in the proximal direction, the clicker is deformed, as the spinner pushes part of the clicker in the proximal direction, but another part of the clicker cannot move in the proximal direction because the powerpack housing 240 blocks this movement. This results in a distortion of the clicker (i.e. a build-up of potential energy in the clicker). The clicker may release a clicking sound as it is distorted from its initial more relaxed (or relaxed) state to its distorted state.

Another 90 degrees of rotation would move the spinner back from its proximal-most position to its distal-most position. This movement is driven by the release of the potential energy build-up in the clicker, which pushes the spinner back in the distal direction once the interaction between the follower structure and the guide structure allows this. The clicker may release a clicking sound as it relaxes back from its distorted state.

In the example depicted herein, the guide structure and follower structure design results in the spinner moving from its proximal-most position to its distal-most position and back again every 180 degrees, so twice per full 360-degree rotation of the spinner. However, with other guide structure and follower structure designs, the spinner could move from its proximal-most position to its distal-most position and back a different number of times per 360-degree rotation, for example once or three or more times. This could be used to vary the frequency and/or the pattern of clicks by the clicker. The angle of the sloped surfaces 389, 395 could be constant relative to the axis along the length of the sloped surfaces, or could vary (e.g. in a sinusoidal pattern).

The feedback sub-assembly shown in FIG. 121 can provide repeated clicks (continuous clicking) (e.g. more than 5 clicks, more than 10 clicks or more than 20 clicks) during medicament delivery from a device, thereby providing an audible indication to a user that an injection is underway. Feedback sub-assemblies of this type could also be used for a single click (e.g. end click indicating end of medicament delivery, start click indicating start of medicament delivery, and/or priming click indicating that priming is complete). Although the example given here would typically use multiple rotations of the spinner relative to the housing to provide repeated clicks, this type of feedback sub-assembly could also work from a single 360-degree rotation of a component relative to another component, or also from a partial rotation of one component relative to another component, particularly when one or more single clicks is required rather than continuous clicking during medicament delivery. Feedback sub-assemblies of this type could be used alone or combined with other visual, audible and/or tactile feedback mechanisms.

In this particular design, it is the powerpack lock 220 that rotates relative to the housing and is attached to the spinner, thereby providing the rotation required for the spinner to rotate relative to the housing. A rotational lock 229 on the powerpack lock 220 and a rotational lock 386 on the spinner 380 rotationally lock the powerpack lock 220 and the spinner 380 together; a particular shape for the lock is shown but could be varied.

The spinner 380 is attached to the powerpack lock 220 in the example shown in FIG. 121. In general, the spinner 380 could be rotationally attached to any component that rotates relative to another component—for example a plunger rod relative to a housing in medicament delivery devices where the plunger rod rotates relative to a housing of the medicament delivery device. The spinner could also be an integral part of a component (e.g. an integral part of the powerpack lock 220 or of a plunger rod) rather than a separate component.

In the example shown in FIG. 121, the spinner has two protrusions 384, but could alternatively have one, three or more. The two protrusions 384 are opposite each other relative to the longitudinal axis; this is optional, though symmetry may be preferable, for example to keep forces balanced within a device, and providing more protrusions (2 or more) may produce a louder click. The protrusions could be on the surface of the clicker 500 rather than on the spinner; with a proximally facing surface of the spinner interacting with the protrusions of the clicker. In another alternative, one or more protrusions on the clicker (e.g. protrusions extending in the distal direction from the distally facing surface 504 of the clicker) and protrusions 384 on the spinner 380 are both provided. As the spinner 380 rotates, the protrusion of the spinner interacts with the protrusion of the clicker, thereby pushing the clicker (in the proximal direction) and creating a click (the protrusions could optionally have ramped ends to reduce the friction caused by the protrusions interacting with one another). In this alternative, guide structures such as those shown in FIGS. 127 and 128 would not be required, as the spinner would not need to move in the proximal direction to cause the clicker to create a click.

In the example shown in FIG. 121, the spinner cap 390 is described as a separate part. However, the spinner cap can be considered to be a part of the housing 40. Similarly, the powerpack housing 240 can be considered to be a part of the housing 40. More generally, therefore, the combination of the housing 40, the powerpack housing 240 and the spinner cap 390 can be considered to simply be a housing (and could instead be a single integral part or a total of two or more separate parts). As such, the spinner cap can be described simply as a housing or as a housing part.

The clicker 500 could be plastic or metal, for example. The clicker is a disc in the depicted example (with an optional relatively small hole 506 in the middle), but could alternatively be another shape, such as a ring, a rectangle or a square. The hole 506 is optional, as mentioned above. This allows the spinner (and/or the powerpack lock 220) to extend through the clicker. This is needed in the particular design depicted in the Figures because the clicker is between the powerpack lock 220 and the spinner 380, but might not be needed with different clicker shapes. If the positions of the spinner and clicker were reversed this hole 506 might also no longer be needed.

Figure 129:
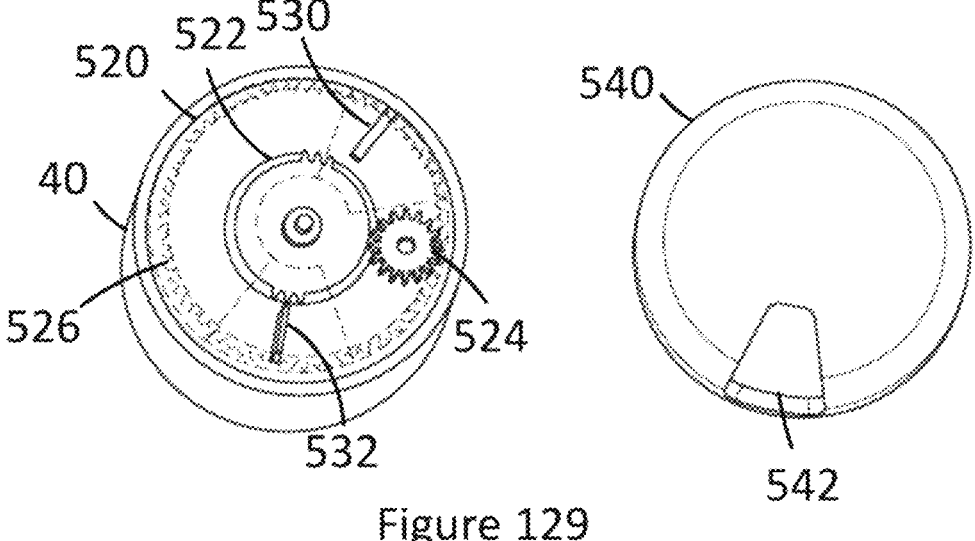
Figure 130:
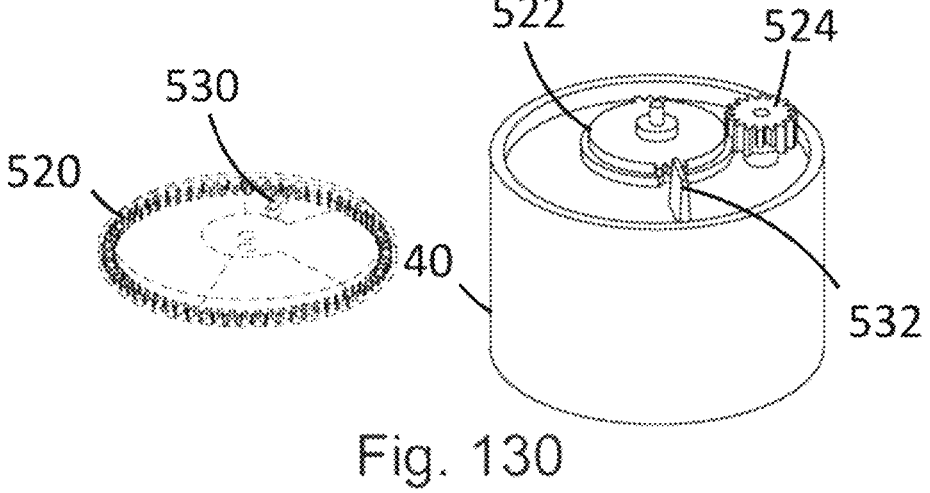

Another feedback mechanism, which could be used in combination with the solutions described herein (e.g. in FIG. 74 or FIG. 121) or with other devices where one component rotates relative to another, is shown in FIGS. 129 and 130. In this mechanism, a geared mechanism is provided that translates the number of rotations (in this case rotations of the powerpack lock 220) required to complete the injection, e.g. 1800 degrees, into a reduced amount of rotation, e.g. a less than 360-degree rotation of a disc (display wheel) 520 that features visual graphics to communicate the status of injection. The view of the display wheel can be partially blocked by a cover 540 (or an opaque portion of a cover) to only reveal a portion of the display wheel to the user (for example some text or a colour) through a gap 542. An optional label elsewhere on a device comprising this feedback mechanism could identify that the colour green showing in the gap denotes that the device is ready to use, for example. Once the injection is started and the powerpack begins rotating the geared mechanism rotates the display wheel to no longer show green but yellow instead, for example. The label on the device could identify that the yellow colour denotes that the injection is in progress. As the powerpack reaches the end of injection, the display wheel will have rotated enough to show the final end of injection status red colour. The label on the device could identify that the red graphic denotes that the injection is completed, and/or that the user should wait a number of seconds before removing the device, and/or that the device is now used/not ready for use. The gearing means that the display wheel does not continuously move but moves in steps after a certain rotation—in this case every 180-degree rotation—of the rotational component (e.g. powerpack lock or plunger rod). This can create a clear definition between changing of text and/or colour graphics. The mechanism features a driving gear 522 directly linked to the rotational power source (not shown), a reduction gear 524 that is driven by the driving gear every 180 degrees in this example, and the display wheel which features internal facing teeth 526 and is driven by the reduction gear, as shown in FIGS. 129 and 130.

Alternatively, the gearing does not create stepped movement but instead continuous rotation of the display wheel. This would require the interfacing gearing to instead not have any teeth missing. Alternatively, the disc could provide audible feedback instead of (or as well as) visual feedback. The visual feedback could be provided in various ways, including text, colours, and/or graphical imagery to communicate, for example, that the device is unused, that the device is ready for use, that an injection is ongoing, that an injection is completed, and/or that a device is used. The number of rotations required from the start to end of injection could be tailored to the need of the device through adjusting the ratio between gears.

In addition to any other audible clicks that might be provided, a distinct click, for example an end click, could be provided via a rigid rib (or a rigid protrusion) on the proximal side of the display wheel which during the final stepped rotation (e.g. moving from yellow to red) comes into contact with and flexes a flexible arm that produces a clicking sound once released by the rotating display wheel rib (or protrusion). The position of the flexible arm and rigid rib could be swapped. This approach could alternatively or additionally be used for other clicks, such as a start click.

Several different example autoinjectors have been described herein. There are various differences between the described autoinjectors, but generally the different features of the different autoinjectors are interchangeable, especially at the level of functional sub-assemblies such as the powerpack, the needle guard lock assembly or the lock mechanism.

One or more of the cap, housing, and needle shield are typically (though not necessarily) tubular, as this can help these parts provide other functions besides the function of a lock mechanism.

Typically, the lock mechanisms described above are for use in autoinjectors (or medicament delivery devices more generally) in which the autoinjector is activated (at least in part) by distal movement of the needle guard, as these lock mechanisms can then be used to stop premature activation (activation before the cap is removed, for example when the autoinjector is dropped). However, such lock mechanisms could also be useful in devices activated in other ways. Another benefit of such lock mechanisms is that the lock mechanism restricts movement of parts relative to one another, which could also be useful in securing devices to minimise the chance of damage during transport, for example.

In this application, examples have been described with an emphasis on autoinjectors with needles. However, the concepts described herein could also be implemented in pen injectors or medicament delivery devices more generally. For example, needle guard lock assemblies as described herein could be used in autoinjectors with needles, autoinjectors with jet injectors, or in pen injectors. An autoinjector is generally defined as an injection device in which at least one part of the process, for example medicament injection, needle insertion or needle guard retraction, is carried out by the autoinjector and therefore does not need to be carried out by the user.

Relative positions of features in this application are generally described with reference to an axis (central axis) 20, along with a corresponding axial direction (longitudinal direction) 22, circumferential direction 24 and radial direction 26. The devices in general (and also the individual components) can be described as extending from a proximal end 14 to a distal end 16. These terms are depicted in FIG. 29, for example. When not specified, movement of individual parts is typically described relative to a housing such as the housing 40. The individual parts as described herein are typically single integral parts, though they can alternatively be made of two or more separate parts (e.g. the housing as shown in FIG. 29).

In general, the housing (outer housing) 40 can be provided as a single piece (e.g. FIG. 10) or two or more pieces (e.g. the proximal housing 42 and the distal housing 44 in FIG. 29); these variations in housing design are also interchangeable between the described examples. The housings shown are tubular, and more specifically are cylindrical, but other shapes are also possible without compromising device functionality (for example, the housing shown in FIG. 99 is a rounded square is cross-section perpendicular to the axis, rather than having a circular cross-section). Non-cylindrical designs can also help reduce the rollability of devices when placed on a surface. Although the housing would typically be the outermost component, it could also support the device as an internal component. A window 46 is optionally provided in the housing, for example for medicament inspection prior to device use. The housing optionally comprises a neck 39 (FIG. 53 for example; FIGS. 70 and 99 also illustrate less accentuated necks); the neck is typically a ring around the housing that has a smaller external diameter than the rest of the housing (or at least a smaller external diameter than the housing immediately proximal and distal to the ring), and can help make it easier to grip the housing.

In this application, the focus is on describing needle guard lock assemblies where the proximal part of the arm of the needle lock is biased away from the axis to interact with a slit or recess. The mechanism could also be reversed, with the slit closer to the axis than the proximal part of the arm of the needle lock and the proximal part of the arm biased towards the axis to interact with a slit or recess. In such a case, the slit or recess could still be in an outer housing as described herein (especially in examples where a syringe holder or a powerpack housing is an integral part of the outer housing), or alternatively the housing comprising the slit could be part of another component that is fixed to an outer housing, such as a syringe holder.

Many of the features described herein are shown duplicated, typically with two of each feature 180 degrees apart in the circumferential direction 24 around the axis 20 (i.e. with two-fold rotational symmetry). However, this symmetry is not essential, and in general only one of each feature need be provided to be effective functionally (for example one arm, one protrusion, one slit, one recess). Nevertheless, there can be a benefit in terms of ease of manufacturing, ease of assembly, reliability and/or device stability during use by having two, three or more of any particular feature, preferably spread out equally around the axis.

The slit 45 in the housing extends through the housing in the radial direction. Alternatively, the slit could be replaced by a recess that only extends part of the way through the housing in the radial direction.

In general, the devices described herein can be split up into various sub-assemblies. At the highest level, an autoinjector can be split into a front sub-assembly, a primary package and a rear sub-assembly. The front sub-assembly typically comprises a cap, a housing, a needle guard and a syringe holder. The primary package typically comprises a needle shield (for example a rigid needle shield and/or a flexible needle shield), a syringe comprising a needle, a medicament in the syringe, and a stopper. The rear sub-assembly can typically be more varied in its composition, but typically includes a powerpack of some kind and optionally also various other features. One example of a powerpack assembly is shown in FIG. 18, comprising a driver, a powerpack lock, a torsion spring and a powerpack housing. A device can also be split up into various interacting sub-assemblies, including a medicament delivery member lock assembly such as the needle guard lock assembly 58, which comprises the needle guard 60 from the front sub-assembly, along with the lock activation sleeve 80, the needle guard lock 100 and the housing 40 (or part of the housing such as the distal housing 44) from the rear sub-assembly, which together make up the components required for locking the needle guard after use. Another sub-assembly is the activation sub-assembly (FIG. 20 for example), comprising the lock activation sleeve, the needle guard lock, the plunger rod and the driver nut. Other sub-assemblies are also possible, and the sub-assemblies and components described herein are not limited to use within the particular devices described herein—for example, the powerpack sub-assemblies described herein could be used in devices that do not include an activation sub-assembly as described herein, and the lock mechanisms described herein could be used in devices that do not include a powerpack sub-assembly. Indeed, in general the individual sub-assemblies described herein could be included in completely different devices, and can be used in devices that are different from the particular examples described herein. Typically, the various sub-assemblies and components in the different examples described herein are interchangeable—for example, the needle guard lock assemblies shown in FIGS. 1 and 5 could be used in the autoinjectors shown in FIGS. 10 and 29, and the spinner shown in FIG. 40 could be implemented in any of the described autoinjectors.

Providing a needle guard (needle cover) 60, or a medicament delivery device guard more generally, is required in the context of providing the needle guard lock assemblies described herein, but is optional more generally. The description focusses on examples in devices with needles; however, a needle could also be substituted for another medicament delivery member such as a jet injector. As such, any mention of a needle herein can be generalised to a medicament delivery member. By extension, any mention of a needle guard herein can be generalised to a medicament delivery member guard.

A needle guard typically comprises a proximal tubular portion (e.g. guard portion 64) and one or more arms (e.g. needle guard arm 62) extending in the distal direction from the tubular portion, with the tubular portion forming the needle guard and the one or more arms interacting with other parts of the device as needed—for example with the lock activation sleeve 80. Optionally, the one or more arms comprise a slit 66. Additionally or alternatively, the slit 66 extends into the guard portion 64 (see e.g. FIG. 13). Instead of a slit 66, a recess could instead be provided.

The lock activation sleeve 80 can be different shapes depending on the device and the functionality desired. In the examples described above, the lock activation sleeve 80 comprises a tubular section 82, arms 84 with pads 86 and cut-outs 88 for the distal part 108 of the arm of the needle guard lock 100. As can be seen in FIG. 21, the cut-outs 88 extend in both the arms 84 and the tubular section 82, though they could alternatively extend only in the arms or only in the tubular section. Recesses could be provided instead of cut-outs. In general, the arms are also optional and the pads 86 could be on the tubular section 82; the functional reason for the arms 84 of the lock activation sleeve is that it allows the arms 324 of the driver nut 320 to extend outwards radially (see e.g. FIG. 47) without the tubular section 82 of the lock activation sleeve getting in the way. The lock activation sleeve is typically arranged in the housing at the distal end of the needle guard lock, with most or all of the lock activation sleeve further from the proximal end than the needle guard prior to device use.

The pads 86 shown in the examples herein comprise a protrusion extending towards the axis from the arms 84. The protrusions extend further in the axial direction than the radial direction, and are shaped to correspond with the arm 104 of the needle guard lock, for example by including angled sections at the proximal and distal ends of the pad (see e.g. FIG. 25) with the proximal end of the pad angled towards the proximal end and the distal end of the pad angled towards the distal end. The shape of the pads 86 can vary considerably and still provide a functional lock activation sleeve. The primary requirement is that the pad pushes the distal part 108 of the arm 104 towards the axis when the lock activation sleeve is moved in the distal direction, and as such, the pad could simply be protrusion on the arm 84 of the lock activation sleeve or even a flat surface of the arm 84 of the lock activation sleeve.

The needle guard lock 100 comprises a base such as a tubular section 102 and at least one arm. The function of the base is typically to support the arm and to hold the needle guard lock in place relative to another part, such as the housing 40, the distal housing 44 and/or a syringe holder, for example. The base would typically be rigid, although in some cases the base could also be flexible and flex along with the arm. In the examples described herein, a pivot 105 extends between the base of the lock activation sleeve and the lock activation sleeve arms. This pivot is optional, and the arms could be attached directly to the tubular section, particularly when the tubular section is also flexible. The arms can take various shapes as well. In general, protrusions 110 on the arms are optional. A rib 107 extending in the radial and axial directions to support the arm can also be provided, as shown in FIG. 24 for example. An optional slit 119 (see FIG. 24) can also be provided to rotationally lock the lock activation sleeve relative to the driver nut 320. Functionally, the needle guard lock arms are intended to pivot so that the distal part 108 of the arm is moved towards the axis when the device is used, biasing the proximal part 106 of the arm away from the axis. Preferably, the distal end of the distal part 108 is further from the axis 20 than the proximal end of the distal part 108, to help the activation sleeve engage with the distal part 108. An optional protrusion 110 can help the proximal part 106 of the arm engage with the housing as described above.

The needle guard lock can be a separate component as shown in the examples herein, or could alternatively be an integral part of another component such as a housing or a syringe holder.

As shown the example in FIG. 24, the needle guard lock 100 can have other features—in FIG. 24, a concertina section 112 that is configured to vary in length in the axial direction is included. The concertina section can reduce in length in the axial direction during assembly so as to allow parts to fit snugly together without rattling. The concertina has a support portion (in this case a support ring 117) and two arms 118, with the arms extending from the tubular section 102 of the needle guard lock to the support ring 117, and with the arms extending in both the longitudinal and circumferential directions, thereby allowing the arms to bend and take up less space in the axial direction when the needle guard lock is compressed in the axial direction. The support ring 117 is optional (without a support portion, the end of the arms 118 distal from the base of the needle guard lock can be considered to be the support portion, since the end of the arms 118 would then abut the adjacent component), but can be beneficial to better engage the adjacent component (a syringe in the examples herein). Instead of two arms, one, three or more arms could be provided. The shape of the arms could also be changed, for example to a zigzag shape. The support portion typically abuts a syringe in an assembled medicament delivery device, though it could abut another component such as a syringe holder or a housing.

Provision of a syringe holder 120 is generally optional, and the syringe could alternatively be held by other components such as the housing or a clip. The syringe holders described herein include various optional features, including a proximally facing ledge 122, a window 124, a protrusion 126, and a hook 128. A proximally facing arm 129 may also optionally be provided, along with a radially outwardly facing protrusion 130 on the arm 129 and a radially inwardly facing protrusion 131 on the arm 129. The radially outwardly facing protrusion 130 extends through the slit 66 of the needle guard arm (see FIG. 14). The arm 129 can flex outwards to allow a needle shield (for example a rigid needle shield 364) of a syringe to pass the radially inwardly facing protrusion 131 subsequently during assembly. Later on, though, once a device is fully assembled, the radially outwardly facing protrusion 130 abuts a housing such as the housing 40 (in the radial direction), stopping the radially outwardly facing protrusion 130 (and by extension the arm 129 and the radially inwardly facing protrusion 131) from moving away from the axis in the radial direction, meaning that the syringe (for example a shoulder 363 of the syringe 362) can be supported by the radially inwardly facing protrusion 131 during injection. The syringe holder is typically tubular. The proximally facing ledge 122 could extend part of the way around the syringe holder in the circumferential direction, or all the way round, or could be several separate portions, or could be replaced by one or more protrusions.

The needle guard spring 140 is optional, and the needle guard could also be re-extended after use by hand. The needle guard spring is typically arranged between the needle guard and the syringe holder, but could be arranged between other parts, e.g. the needle guard and a housing.

The cap 160 is also generally optional, and can comprise one or more parts. The cap typically comprises a rigid needle shield remover. A cap that is removed by pulling in the axial direction is shown in the examples herein. Other types of cap, for example screw caps or caps that are removed by twisting, could be provided instead.

Various alternatives are possible for the end cap 200. The end cap could be integral to the housing and is therefore an optional component. The spinner cap 390 is a type of end cap and could be used instead of the end cap 200 or vice versa.

The powerpack housing 240 is another optional component, and its functions could be provided by other components such as the housing. Various modifications to the powerpack housing are possible—for example, the spring holder 400 (see FIG. 30 in particular) is another example of a powerpack housing.

In the examples given herein, torsion springs are used, and the described examples are particularly designed with torsion springs in mind as they are designed in a way that allows for winding up of the spring during manufacture and also in a way that allows the components to withstand the stress put on them by the twisted spring. Alternatively, though, many of the features described herein, including aggregations of parts such as the front sub-assembly, the activation sub-assembly and/or the needle guard lock assembly could also be used in other medicament delivery devices, for example in autoinjectors with compression springs or electrically-powered powerpacks. The structure by which the torsion spring is attached, for example the proximal end protrusion (hook) 262 and the distal end protrusion 264, can also be modified depending on the shape of the components the torsion spring is attached to.

The driver 280 can also be modified in various ways depending on the shape of the surrounding components, as is apparent by comparing the drivers in FIGS. 17 and 30. For example, the shape and extent of the teeth 286 may vary depending on the shape and extent of the corresponding driver nut teeth 326. Alternatively, rather than multiple teeth on both sides, one or more teeth may be provided on the driver or the driver nut, with corresponding recesses or holes provided on the other of the driver and the driver nut. In another alternative to teeth, corresponding flattened sections could be provided on the driver and the driver nut, similar to the interaction between the plunger rod and the driver as shown in FIG. 37.

The plunger rods 300 described herein include two flattened sides 304, but as with the duplicated features herein in general, only one is needed. Broadly speaking, the plunger rod doesn't have to have a flattened side at all, but just needs to be non-circular in cross section where it engages the driver so that it can be rotated by the driver. The screw thread is typically on a portion of the plunger that does not engage the driver, with the screw thread typically engaged by the driver nut 320. The snap fit ledge 306 is optional and is one example of how the plunger rod could engage a thrust bearing when a thrust bearing is provided; alternatively, the proximal end of the plunger rod could be shaped to instead directly engage a stopper.

Considerable variation in the shape of the driver nut 320 is also possible, as is already apparent from the differences in driver nut shape in the examples described herein. The driver nut is also optional in some examples, particularly those using a compression spring rather than a torsion spring. As with various other components, some features are also interchangeable between the examples described herein—for example, the optional driver nut protrusion 328 in e.g. FIG. 26 could also be included in the driver nut of FIG. 35.

The thrust bearing 340 is optional, as the plunger rod can directly engage the stopper, but can be beneficial to spread the load on the stopper and to only transmit the axial (and not the rotational) force from the plunger rod to the stopper. Typically, the thrust bearing engages with the inside of the stopper (e.g. cavity 369 of the stopper)) and/or the distal end of the stopper (e.g. outer rim 367 of the stopper) (see e.g. FIG. 42). The thrust bearing shape can be modified depending on the shape of the stopper and the plunger rod in particular.

Provision of a spinner 380 is optional, and could be provided on the examples in FIGS. 10 and 53 as well. The spinner could be attached to any part of the device that rotates during injection, such as the plunger rod and/or the driver. Generally speaking, a spinner could be used on any autoinjector or medicament delivery device that has a part (such as a plunger rod or a driver) that rotates during drug injection, and is not limited to the autoinjectors described herein. Additionally or alternatively to a spinner, audible or tactile feedback (or other visual feedback) can be provided, either as feedback indicating the start of injection, the end of injection and/or indicating that the injection is in progress. So that the spinner is visible, a window 392 (or two or more windows) can be provided in an end cap such as in the spinner cap 390. Each window could be a cut-out or a see-through portion in the spinner cap 390 (or in an end cap more generally). The shape of the example window shown in FIG. 40 is generally shaped like a sector of a circle, but other shapes are also possible. Instead of providing a window, the entire spinner cap or end cap could be made of a transparent material.

Another additional or alternative example of feedback indicating that the injection is in progress could be interaction between the powerpack lock and the powerpack housing to provide a sound during the injection; this is a benefit of the powerpack lock being part of the device rather than simply a tool used to lock the powerpack during intermediate steps in the manufacturing process. Another example of feedback indicating that the injection is in progress could be interaction between the driver nut and the driver, for example between the teeth of the driver nut and the teeth of the driver. Whilst the driver is free to rotate once the teeth of the driver nut are free to extend away from the axis (see e.g. FIG. 35), the teeth of the driver nut optionally remain biased towards the driver (rather than being biased to stay away from the driver), which would mean that the teeth of the driver nut and the teeth of the driver would be free to move past each other but would continue to interact as the driver rotates, providing a clicking sound as the injection proceeds.

Various modifications to the embodiments described are possible and will occur to those skilled in the art without departing from the present disclosure which is defined by the following claims.

Some aspects of the present disclosure are summarised in the following clauses.

1. A medicament delivery member guard lock assembly (58) for a medicament delivery device (10), the medicament delivery member guard lock assembly (58) comprising:
    a housing (40) extending along an axis (20) in an axial direction (22) from a proximal end (14) to a distal end (16), the housing (40) comprising a recess or a slit (45);
    a medicament delivery member guard (60) slidably arranged in the housing (40), the medicament delivery member guard (60) extending from a proximal end (14) to a distal end (16);
    a lock activation sleeve (80) slidably arranged in the housing (40) at the distal end (16) of the medicament delivery member guard (60); and
    a medicament delivery member guard lock (100) arranged in the housing (40) adjacent to the lock activation sleeve (80), wherein the medicament delivery member guard lock (100) comprises a base (102) and a flexible arm (104) pivotally attached to the base (102), wherein the flexible arm (104) comprises a proximal part (106) and a distal part (108), wherein the flexible arm (104) is attached to the base (102) between the proximal part (106) and the distal part (108), and wherein the proximal part (106) of the flexible arm (104) is arranged adjacent to the recess or slit (45) in the housing (40).

2. The medicament delivery member guard lock assembly of clause 1, wherein the medicament delivery member guard comprises a distally facing surface and the lock activation sleeve comprises a corresponding proximally facing surface with which the distally facing surface of the medicament delivery member guard engages so as to push the lock activation sleeve in the distal direction when the medicament delivery member guard is pushed in the distal direction, wherein the lock activation sleeve comprises a radially facing surface relative to the axis, with which radially facing surface the distal part of the flexible arm of the medicament delivery member guard lock is pushed in the radial direction to bias the flexible arm of the medicament delivery member guard lock against the medicament delivery member guard when the lock activation sleeve is pushed in the distal direction, and wherein, when the medicament delivery member guard is subsequently moved back in the proximal direction, the proximal part of the flexible arm of the medicament delivery member guard lock moves towards or into the recess or slit in the housing.

3. The medicament delivery member guard lock assembly of clause 1 or 2, wherein the medicament delivery member guard is configured to push the lock activation sleeve in the distal direction when the medicament delivery member guard is pushed in the distal direction, wherein the lock activation sleeve is configured to push the distal part of the flexible arm of the medicament delivery member guard lock in the radial direction relative to the axis to bias the flexible arm when the lock activation sleeve is pushed in the distal direction, and wherein, when the medicament delivery member guard is subsequently moved back in the proximal direction, the proximal part of the flexible arm of the medicament delivery member guard lock moves towards or into the recess or slit in the housing.

4. The medicament delivery member guard lock assembly of any previous clause, wherein the proximal part of the flexible arm of the medicament delivery member guard lock comprises a protrusion extending in the radial direction.

5. The medicament delivery member guard lock assembly of any previous clause, wherein at least part of the flexible arm of the medicament delivery member guard lock is further from the axis than the base.

6. The medicament delivery member guard lock assembly of any previous clause, wherein the medicament delivery member guard lock comprises a concertina section, the concertina section having a variable length in the axial direction, and the concertina section extending in the axial direction from the proximal end of the medicament delivery member guard lock.

7. The medicament delivery member guard lock assembly of clause 6, wherein the concertina section comprises a support portion spaced apart from the base of the medicament delivery member guard lock and at least one arm, the arm extending from the base of the medicament delivery member guard lock to the support portion.

8. The medicament delivery member guard lock assembly of any previous clause, wherein the distal end 113 of the distal part 108 of the flexible arm is further from the axis 20 than the proximal end 109 of the distal part 108 of the flexible arm.

9. The medicament delivery member guard lock assembly of any previous clause, wherein the medicament delivery member guard comprises a proximal portion and a distal portion, wherein the proximal portion is tubular and the distal portion comprises an arm.

10. The medicament delivery member guard lock assembly of clause 9, wherein the arm of the medicament delivery member guard comprises a recess or slit extending in the axial direction.

11. The medicament delivery member guard lock assembly of any of clauses 2 to 10, wherein the radially facing surface of the lock activation sleeve faces towards the axis 20.

12. The medicament delivery member guard lock assembly of any of clauses 2 to 10, wherein the distally facing surface of the medicament delivery member guard and the proximally facing surface of the lock activation sleeve are spaced apart in the axial direction.

13. A medicament delivery device comprising the medicament delivery member guard lock assembly of any previous clause.

14. A lock mechanism for a medicament delivery device, the lock mechanism extending from a proximal end to a distal end in an axial direction relative to a longitudinal axis, the lock mechanism comprising a housing, a medicament delivery member guard and a cap, wherein one of the medicament delivery member guard and the cap comprises a protrusion extending in a radial direction relative to the longitudinal axis, wherein the other of the medicament delivery member guard and the cap comprises a recess or cut-out, wherein the protrusion is in the recess or cut-out, wherein the medicament delivery member guard is moveable in the direction of a longitudinal axis relative to the housing from a locked position to an unlocked position, wherein in the locked position, movement of the protrusion relative to the recess or cut-out is restricted by a wall of the housing, and in the unlocked position, the movement of the protrusion relative to the recess or cut-out is no longer restricted by the wall of the housing, thereby allowing the protrusion to be moved out of the recess or cut-out and the cap to be removed from the medicament delivery member guard.

15. The lock mechanism of clause 14, wherein at least one of the cap and the medicament delivery member guard comprises a flexible portion.

16. The lock mechanism of clause 15, wherein the flexible portion is a flexible arm of the cap.

17. The lock mechanism of clause 16, wherein the recess or cut-out is in the flexible arm.

18. The lock mechanism of any one of clauses 14 to 17, wherein the cap comprises a cap housing and a cap insert, and the cap insert is rotatable relative to the cap body.

19. The lock mechanism of clause 18, wherein the cap insert is attached to the cap body by a snap fit that restricts movement of the cap insert relative to the cap body in the axial direction.

20. The lock mechanism of clause 18 or 19, wherein the rotational movement of the cap insert relative to the cap body is limited by a rib extending from the cap body.

21. The lock mechanism of any of clauses 14 to 20, wherein the cap comprises a distally facing surface abutting a proximally facing surface of the housing, and wherein the distally facing surface of the cap and the proximally facing surface of the housing each describe a sinusoidal pattern in a circumferential direction relative to the longitudinal axis.

22. The lock mechanism of any of clauses 14 to 21, wherein the wall of the housing faces in the radial direction.

23. The lock mechanism of any previous clause, wherein the cap comprises a medicament delivery member guard remover.

24. A medicament delivery device comprising a lock mechanism as described in any of clauses 1 to 23.

25. The medicament delivery device of clause 24, wherein the medicament delivery device is an autoinjector.

26. The medicament delivery device of clause 24 or 25, wherein the medicament delivery device comprises a powerpack inside the housing and a primary package inside the housing.

27. The medicament delivery device of any of clauses 24 to 26, wherein the medicament delivery device comprises a housing, and wherein the protrusion and/or the flexible arm is inside the housing.

28. The medicament delivery device of clause 27, wherein a proximal end of the protrusion and/or a proximal end of the flexible arm is distal to the proximal end of the housing.

29. A feedback mechanism sub-assembly for a medicament delivery device, the feedback mechanism sub-assembly comprising a housing, a clicker and a spinner,
  wherein the spinner is arranged between the housing and the clicker,
  wherein the housing comprises a guide structure that engages a corresponding follower structure of the spinner so that, when the spinner is rotated relative to the housing, engagement of the follower structure by the guide structure results in linear motion of the spinner relative to the housing,
  wherein a proximally facing surface of the clicker abuts a distally facing surface of the housing and a distally facing surface of the clicker abuts a proximally facing surface of the spinner, so that the clicker can be deformed from a first shape to a second shape during linear motion of the spinner relative to the housing when the spinner rotates relative to the housing.

30. The feedback mechanism sub-assembly of clause 29, wherein the distally facing surface of the clicker is convex when the clicker is in the first shape and wherein the distally facing surface of the clicker is concave when the clicker is in the second shape.

31. The feedback mechanism sub-assembly of clause 29 or 30, wherein the clicker is in a relaxed state in the first shape and a tensioned state in the second shape.

32. The feedback mechanism sub-assembly of any of clauses 29 to 31, wherein the proximally facing surface of the spinner is a proximal end of a protrusion of the spinner.

33. The feedback mechanism sub-assembly of any of clauses 29 to 32, wherein the distally facing surface of the clicker is a distal end of a protrusion of the clicker.

34. The feedback mechanism sub-assembly of any of clauses 29 to 33, wherein the proximally facing surface of the spinner is closer to an axis than the distally facing surface of the housing.

35. The feedback mechanism sub-assembly of any of clauses 29 to 34, wherein the clicker has a hole through the centre in an axial direction.

36. The feedback mechanism sub-assembly of any of clauses 29 to 35, wherein the clicker is a plate.

37. The feedback mechanism sub-assembly of any of clauses 29 to 36, wherein the housing comprises a spinner cap.

38. The feedback mechanism sub-assembly of any of clauses 29 to 37, wherein the feedback mechanism sub-assembly extends along an axis in an axial direction, and the motion of the spinner relative to the housing is in the axial direction.

39. The feedback mechanism sub-assembly of any of clauses 29 to 38, wherein the proximally facing surface of the clicker that abuts the housing is further away from a longitudinal axis than the distally facing surface of the clicker that abuts the spinner.

40. The feedback mechanism sub-assembly of any of clauses 29 to 39, wherein the proximally facing surface of the spinner is on a protrusion of the spinner.

41. The feedback mechanism sub-assembly of any of clauses 29 to 40, wherein at least one of the guide structure and the follower structure comprises a sloped surface extending around an axis and in the axial direction.

42. The feedback mechanism sub-assembly of any of clauses 29 to 41, wherein at least one of the guide structure and the follower structure comprises a protrusion extending in the axial direction.

43. A medicament delivery device comprising the feedback mechanism sub-assembly of any of clauses 29 to 42.

44. A lock mechanism for a medicament delivery device, the lock mechanism extending from a proximal end to a distal end in an axial direction relative to a longitudinal axis, the lock mechanism comprising a housing (40, 42, 44), a medicament delivery member guard (60) and a cap (160),
  wherein one of the medicament delivery member guard (60) and the housing (40, 42, 44) comprises a flexible arm (410), the flexible arm (410) comprising a protrusion (412) extending in a radial direction relative to the longitudinal axis,
  wherein the other of the medicament delivery member guard (60) and the housing (40, 42, 44) comprises a recess or cut-out (70),
  wherein part of the flexible arm (410) is in the recess or cut-out (70),
  wherein the flexible arm (410) is between the cap (160) and the other of the medicament delivery member guard (60) and the housing (40, 42, 44), and
  wherein the cap (160) is adjacent to the flexible arm (410) in a radial direction relative to the longitudinal axis.

45. The lock mechanism of clause 44, wherein the housing extends around the medicament delivery member guard, and wherein the housing comprises the flexible arm and the medicament delivery member guard comprises the recess or cut-out.

46. The lock mechanism of clause 44 or 45, wherein the proximal end of the cut-out or recess is spaced apart in the longitudinal direction from the protrusion.

47. The lock mechanism of any of clauses 44 to 46, wherein the recess or cut-out is a first recess or cut-out, and the other of the medicament delivery member guard and the housing comprises a second recess or cut-out that is closer to the proximal end than the first recess or cut-out, and wherein the second recess or cut-out is aligned with the first recess or cut-out in the direction of the longitudinal axis.

48. The lock mechanism of any of clauses 44 to 47, wherein the cap, the housing and the medicament delivery member guard are arranged so that prior to removal of the cap, the housing is blocked from moving in the radial direction and the medicament delivery member guard is thereby blocked from moving in the distal direction, and so that after removal of the cap, the housing can move in the radial direction and the medicament delivery member guard can therefore push the housing in the radial direction to move past the housing in the distal direction.

49. The lock mechanism of any of clauses 44 to 48, wherein the part of the arm that is in the recess or cut-out is the protrusion.

50. A lock mechanism for a medicament delivery device, the lock mechanism extending from a proximal end to a distal end in an axial direction relative to a longitudinal axis, the lock mechanism comprising a housing (40), a medicament delivery member guard (60) and a cap (160, 162, 170),
    wherein one of the medicament delivery member guard (60) and the cap (160, 162, 170) comprises a protrusion (68) extending in a radial direction relative to the longitudinal axis,
    wherein the other of the medicament delivery member guard (60) and the cap (160, 162, 170) comprises a recess or cut-out (172),
    wherein the protrusion (68) is in the recess or cut-out (172),
    wherein the medicament delivery member guard (60) is moveable in the direction of a longitudinal axis relative to the housing (40) from a locked position to an unlocked position, wherein in the locked position, movement of the protrusion (68) relative to the recess or cut-out (172) is restricted by a wall of the housing (40), and in the unlocked position, the movement of the protrusion (68) relative to the recess or cut-out (172) is no longer restricted by the wall of the housing (40), thereby allowing the protrusion (68) to be moved out of the recess or cut-out (172) and the cap (160, 162, 170) to be removed from the medicament delivery member guard (60).

51. The lock mechanism of clause 50, wherein at least one of the cap and the medicament delivery member guard comprises a flexible portion.

52. The lock mechanism of clause 51, wherein the flexible portion is a flexible arm of the cap.

53. The lock mechanism of clause 52, wherein the recess or cut-out is in the flexible arm.

54. The lock mechanism of any one of clauses 50 to 53, wherein the cap comprises a cap housing and a cap insert, and the cap insert is rotatable relative to the cap body.

55. The lock mechanism of any of clauses 50 to 54, wherein the cap comprises a distally facing surface abutting a proximally facing surface of the housing, and wherein the distally facing surface of the cap and the proximally facing surface of the housing each describe a sinusoidal pattern in a circumferential direction relative to the longitudinal axis.

56. A medicament delivery device comprising a lock mechanism as described in any of clauses 44 to 55.

57. The medicament delivery device of clause 56, wherein the medicament delivery device comprises a housing, and wherein the protrusion and/or the flexible arm is inside the housing.

58. The medicament delivery device of clause 57, wherein a proximal end of the protrusion and/or a proximal end of the flexible arm is distal to the proximal end of the housing.

The invention claimed is:
1. A medicament delivery member guard lock assembly for a medicament delivery device, the medicament delivery member guard lock assembly comprising:
    a housing extending along an axis in an axial direction from a proximal end to a distal end, the housing comprising a recess or a slit;

52 a medicament delivery member guard slidably arranged in the housing, the medicament delivery member guard extending from a proximal end to a distal end;
    a lock activation sleeve slidably arranged in the housing at the distal end of the medicament delivery member guard; and
    a medicament delivery member guard lock arranged in the housing adjacent to the lock activation sleeve,
    wherein the medicament delivery member guard lock comprises a base and a flexible arm pivotally attached to the base, wherein the flexible arm comprises a proximal part and a distal part, wherein the flexible arm is attached to the base between the proximal part and the distal part, and wherein the proximal part of the flexible arm is arranged adjacent to the recess or slit in the housing.

2. The medicament delivery member guard lock assembly of claim 1, wherein the medicament delivery member guard comprises a distally facing surface and the lock activation sleeve comprises a corresponding proximally facing surface with which the distally facing surface of the medicament delivery member guard engages so as to push the lock activation sleeve in the distal direction when the medicament delivery member guard is pushed in the distal direction,
    wherein the lock activation sleeve comprises a radially facing surface relative to the axis, with which radially facing surface the distal part of the flexible arm of the medicament delivery member guard lock is pushed in the radial direction to bias the flexible arm of the medicament delivery member guard lock against the medicament delivery member guard when the lock activation sleeve is pushed in the distal direction, and
    wherein, when the medicament delivery member guard is subsequently moved back in the proximal direction, the proximal part of the flexible arm of the medicament delivery member guard lock moves towards or into the recess or slit in the housing.

3. The medicament delivery member guard lock assembly of claim 2, wherein the radially facing surface of the lock activation sleeve faces towards the axis 20.

4. The medicament delivery member guard lock assembly of claim 2, wherein the distally facing surface of the medicament delivery member guard and the proximally facing surface of the lock activation sleeve are spaced apart in the axial direction.

5. The medicament delivery member guard lock assembly of claim 1, wherein the medicament delivery member guard is configured to push the lock activation sleeve in the distal direction when the medicament delivery member guard is pushed in the distal direction,
    wherein the lock activation sleeve is configured to push the distal part of the flexible arm of the medicament delivery member guard lock in the radial direction relative to the axis to bias the flexible arm when the lock activation sleeve is pushed in the distal direction, and
    wherein, when the medicament delivery member guard is subsequently moved back in the proximal direction, the proximal part of the flexible arm of the medicament delivery member guard lock moves towards or into the recess or slit in the housing.

6. The medicament delivery member guard lock assembly of claim 1, wherein the proximal part of the flexible arm of the medicament delivery member guard lock comprises a protrusion extending in the radial direction.

7. The medicament delivery member guard lock assembly of claim 1, wherein at least part of the flexible arm of the medicament delivery member guard lock is further from the axis than the base.

8. The medicament delivery member guard lock assembly of claim 1, wherein the medicament delivery member guard lock comprises a concertina section, the concertina section having a variable length in the axial direction, and the concertina section extending in the axial direction from the proximal end of the medicament delivery member guard lock.

9. The medicament delivery member guard lock assembly of claim 8, wherein the concertina section comprises a support portion spaced apart from the base of the medicament delivery member guard lock and at least one arm, the arm extending from the base of the medicament delivery member guard lock to the support portion.

10. The medicament delivery member guard lock assembly of claim 1, wherein the distal end 113 of the distal part 108 of the flexible arm is further from the axis 20 than the proximal end 109 of the distal part 108 of the flexible arm.

11. The medicament delivery member guard lock assembly of claim 1, wherein the medicament delivery member guard comprises a proximal portion and a distal portion, wherein the proximal portion is tubular and the distal portion comprises an arm.

12. The medicament delivery member guard lock assembly of claim 11, wherein the arm of the medicament delivery member guard comprises a recess or slit extending in the axial direction.

13. A medicament delivery device comprising the medicament delivery member guard lock assembly of claim 1.

14. A method of using a medicament delivery member guard lock assembly, the medicament delivery member guard lock assembly comprising a tubular housing with a recess or a slit, the tubular housing extending from a proximal end to a distal end along an axis, a medicament delivery member guard slidably arranged in the tubular housing, a lock activation sleeve slidably arranged in the tubular housing, and a medicament delivery member guard lock arranged in the tubular housing, the medicament delivery member guard lock comprising a base and a flexible arm pivotably attached to the base, wherein the flexible arm is pivotably attached to the base between a proximal part of the flexible arm and a distal part of the flexible arm, the method comprising the steps of:

pushing the medicament delivery member guard in the distal direction relative to the tubular housing and thereby pushing the lock activation sleeve in the distal direction relative to the tubular housing so that the lock activation sleeve pushes the distal part of the flexible arm of the medicament delivery member guard lock towards the axis and biases the proximal part of the flexible arm of the medicament delivery member guard lock away from the axis; and releasing the medicament delivery member guard so that the medicament delivery member guard moves in the proximal direction, thereby allowing the biased proximal part of the medicament delivery member guard lock to move away from the axis and towards the recess or slit in the tubular housing.

15. The method of claim 14, wherein when the biased proximal part of the medicament delivery member guard lock moves away from the axis, a part of the proximal part of the medicament delivery member guard lock moves into the recess or slit in the tubular housing.

16. A medicament delivery member guard lock assembly for a medicament delivery device, the medicament delivery member guard lock assembly comprising:

a housing comprising a recess or a slit;

a medicament delivery member guard slidably arranged in the housing;

a lock activation sleeve slidably arranged in the housing at a distal end of the medicament delivery member guard; and a medicament delivery member guard lock arranged in the housing adjacent to the lock activation sleeve, wherein the medicament delivery member guard lock comprises a base and a flexible arm having a proximal part and a distal part, where the flexible arm is pivotally attached to the base and where the proximal part is arranged adjacent to the recess or slit.

17. The medicament delivery member guard lock assembly of claim 16, where the flexible arm is attached to the base between the proximal part and the distal part.

18. The medicament delivery member guard lock assembly of claim 16, wherein the medicament delivery member guard comprises a distally facing surface and the lock activation sleeve comprises a proximally facing surface, where the distally facing surface engages the proximally facing surface when the medicament delivery member guard is pushed in the distal direction causing the lock activation sleeve to move in the distal direction, where movement of the lock activation sleeve biases the flexible arm against the medicament delivery member guard.

19. The medicament delivery member guard lock assembly of claim 18, wherein the medicament delivery member guard lock comprises a concertina section, the concertina section having a variable length in the axial direction, and the concertina section extending in the axial direction from the proximal end of the medicament delivery member guard lock.

20. The medicament delivery member guard lock assembly of claim 16, wherein the medicament delivery member guard comprises a proximal portion and a distal portion, wherein the proximal portion is tubular and the distal portion comprises an arm having the recess or slit extending in the axial direction.

* * * * *